US011241579B2

(12) United States Patent
Ardell et al.

(10) Patent No.: US 11,241,579 B2
(45) Date of Patent: Feb. 8, 2022

(54) MONITORING AND MODULATION OF PARASYMPATHETIC NERVOUS SYSTEM

(71) Applicant: THE REGENTS OF THE UNIVERSITY OF CALIFORNIA, Oakland, CA (US)

(72) Inventors: Jeffrey L. Ardell, Oakland, CA (US); Kalyanam Shivkumar, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 377 days.

(21) Appl. No.: 16/094,594

(22) PCT Filed: Apr. 21, 2017

(86) PCT No.: PCT/US2017/028871
§ 371 (c)(1),
(2) Date: Oct. 18, 2018

(87) PCT Pub. No.: WO2017/184993
PCT Pub. Date: Oct. 26, 2017

(65) Prior Publication Data
US 2020/0324116 A1 Oct. 15, 2020

Related U.S. Application Data

(60) Provisional application No. 62/326,296, filed on Apr. 22, 2016.

(51) Int. Cl.
  *A61N 1/36* (2006.01)
  *A61N 1/05* (2006.01)
  *A61N 1/365* (2006.01)

(52) U.S. Cl.
  CPC ...... *A61N 1/36114* (2013.01); *A61N 1/36062* (2017.08); *A61N 1/36139* (2013.01); *A61N 1/36171* (2013.01); *A61N 1/0551* (2013.01); *A61N 1/36117* (2013.01); *A61N 1/36507* (2013.01)

(58) Field of Classification Search
  CPC .................. A61N 1/36114; A61N 1/36062
  USPC .......................................... 607/44
  See application file for complete search history.

(56) References Cited

U.S. PATENT DOCUMENTS

| | | | | |
|---|---|---|---|---|
| 2011/0137362 | A1* | 6/2011 | Foreman | A61N 1/36114 607/14 |
| 2014/0324129 | A1* | 10/2014 | Franke | A61N 1/37235 607/62 |

* cited by examiner

*Primary Examiner* — Nadia A Mahmood
(74) *Attorney, Agent, or Firm* — Riverside Law LLP

(57) ABSTRACT

The present invention provides systems and methods for monitoring cardiac autonomic nervous system activity and modulating parasympathetic control of cardiac function.

18 Claims, 33 Drawing Sheets

*Hemodynamic response to preemptive VNS*

| | HR, beats/min | LVSP | LVEDP | LV +dp/dt |
|---|---|---|---|---|
| Baseline | 83.8 ± 4.8 | 122.1 ± 5.1 | 2.2 ± 0.6 | 1,913.9 ± 125.5 |
| VNS | 57.5 ± 3.7* | 120.3 ± 5.6 | 2.8 ± 0.6 | 1,935.4 ± 154.2 |
| Post-VNS | 95.0 ± 4.4# | 127.8 ± 5.5# | 2.2 ± 0.8 | 2,308.8 ± 181.9# |

Data reflect means ± SE for heart rate (HR), left ventricular systolic pressure (LVSP), left ventricular diastolic pressure (LVEDP), and first derivative of left ventricular (LV) pressure (dp/dt) before (baseline), during, and for 1 min following vagus nerve stimulation (VNS). $P < 0.01$ from baseline (*) and VNS (#).

Figure 3

| | Baseline | 90 Days Post-MI | Baseline | 90 Days Post-MI |
|---|---|---|---|---|
| | LVESV, ml | LVESV, ml | LVEF, % | LVEF, % |
| MI, n = 7 | 0.44 ± 0.07 | 0.57 ± 0.12*† | 80.3 ± 1.7 | 74.9 ± 2.7*† |
| VNS-MI, n = 7 | 0.43 ± 0.11 | 0.41 ± 0.13 | 79 ± 4.4 | 81.4 ± 4.4 |

Values expressed as means ± SE, with number of animals shown. Significant effect (*$P < 0.05$) compared with their baseline level using repeated-measures ANOVA and significant effect (†$P < 0.05$) compared with vagus nerve stimulation (VNS)-myocardial infarction (MI). LVESV, left ventricular end systolic volume; LVEF, LV ejection fraction.

Figure 9

|  | Controls, n = 8 | MI, n = 7 | VNS-MI, n = 7 |
|---|---|---|---|
| Age at termination, wk | 28.2 ± 1.1 | 30.5 ± 0.5 | 29.2 ± 1.9 |
| Postoperative recovery, wk |  | 12.8 ± 0.2 | 12.6 ± 0.3 |
| Body weight (wt), g | 1011 ± 56 | 1106 ± 52 | 1001 ± 94 |
| Heart weight, % of body wt | 0.65 ± 0.08 | 0.61 ± 0.23 | 0.66 ± 0.06 |
| Wet lung weight, % of body wt | 0.51 ± 0.05 | 0.48 ± 0.15 | 0.50 ± 0.05 |
| Dry lung weight, % of body wt | 0.09 ± 0.01 | 0.09 ± 0.02 | 0.10 ± 0.01 |

Values are means ± SD. A Shapiro-Wilk test showed normality, and no significant effect ($P < 0.05$) was found among groups using an ANOVA.

Figure 10

| Property | Controls, n = 64 | MI, n = 55 | VNS-MI, n = 55 |
|---|---|---|---|
| Resting membrane potential, mV | −49.6 ± 0.8 | −44.4 ± 0.6* | −49.5 ± 1.0 |
| AHP amplitude, mV | 15.7 ± 0.6 | 16.4 ± 0.5 | 16.5 ± 0.5 |
| AHP half-decay time, ms | 119.5 ± 6.2 | 105.9 ± 7.7 | 106.0 ± 8.2 |

Values expressed as means ± SE, with number of neurons shown. A Shapiro-Wilk test showed normality, and a significant effect (*$P < 0.05$) with ANOVA is shown for resting membrane potential and input resistance, MI vs. controls and VNS-MI. AHP, afterhyperpolarization.

Figure 11

| Chronic PO Treatment | n | LVSP, mmHg | LVEDP, mmHg | LV +dp/dt, mmHg/s | LV −dp/dt, mmHg/s | HR, beats/min |
|---|---|---|---|---|---|---|
| Sham VNS | 12 | 49.3 ± 3.4 | 3.1 ± 1.2 | 1,211 ± 100 | −1,265 ± 126 | 198.0 ± 7.2 |
| LCV VNS | 9 | 63.1 ± 4.6# | 0.9 ± 1.1 | 1,812 ± 206*# | −1,839 ± 164*# | 215.7 ± 8.8# |
| RCV VNS | 8 | 44.2 ± 2.7 | 2.5 ± 0.5 | 1,058 ± 107 | −1,054 ± 133 | 177.1 ± 12.9 |

Values are means ± SE; n, number of animals. PO, pressure overload; VNS, vagus nerve stimulation; LCV and RCV, left and right cervical vagus; LVSP, left ventricular (LV) systolic pressure; LVEDP, LV end-diastolic pressure; LV +dp/dt and LV −dp/dt, rate of change of LV developed pressure; HR, heart rate. #$p \leq 0.05$ vs. RCV; *$p \leq 0.05$ vs. sham VNS.

Figure 17

| | Crotalo (n = 8) | PO (n = 10) | LCV-PO (n = 9) | RCV-PO (n = 10) |
|---|---|---|---|---|
| Age at termination, wk | 26.2 ± 1.1 | 27.3 ± 1.8 | 26.5 ± 2.8 | 25.6 ± 1.9 |
| Postoperative recovery, wk | | 7.3 ± 0.3 | 7.3 ± 0.3 | 7.3 ± 0.3 |
| Body wt, g | 1011 ± 56 | 1030 ± 77 | 969 ± 94 | 946 ± 86 |
| Heart wt, %body wt | 0.63 ± 0.06 | 0.57 ± 0.05 | 0.59 ± 0.08 | 0.60 ± 0.07 |
| Wet lung wt, %body wt | 0.50 ± 0.08 | 0.41 ± 0.07 | 0.46 ± 0.07 | 0.42 ± 0.05 |
| Dry lung wt, %body wt | 0.09 ± 0.01 | 0.08 ± 0.03 | 0.09 ± 0.03 | 0.09 ± 0.01 |

Values are means ± SD; n, number of animals. No significant effects ($P < 0.05$) was found between groups (by ANOVA).

Figure 18

| | Controls (n = 66) | PO (n = 131) | HCV-PO (n = 113) | LCV-PO (n = 79) |
|---|---|---|---|---|
| RMP, mV | −49.64 ± 0.83 | −49.82 ± 0.68 | −56.58 ± 0.80* | −52.23 ± 0.81 |
| Input resistance, MΩ | 73.2 ± 6.0 | 67.9 ± 5.0 | 73.1 ± 6.6 | 68.3 ± 5.2 |
| AHP amplitude, mV | 15.65 ± 0.58 | 17.46 ± 0.48 | 16.56 ± 0.49 | 16.11 ± 0.53 |
| AHP half-decay time, ms | 119.49 ± 6.15 | 99.46 ± 5.77 | 141.4 ± 6.97* | 109.9 ± 8.37 |

Values are means ± SE; n, number of neurons. RMP, resting membrane potential; AHP, afterhyperpolarization. *Significant effect (P < 0.05) vs. other groups (by ANOVA).

Figure 19

|  | LAD (control) | | LAD (post-stim) | |
|---|---|---|---|---|
|  | BL | CAO | BL | CAO |
| HR | 104.19 ± 16.20 | 120.37 ± 13.94 * | 95.76 ± 15.31 | 108.6 ± 14.69 * |
| LVSP | 129.80 ± 6.87 | 125.20 ± 7.28 * | 138.32 ± 8.28 | 129.38 ± 7.9 * |
| LVEDP | 4.52 ± 0.95 | 6.15 ± 1.23 * | 4.43 ± 1.26 | 6.20 ± 1.42 * |
| dp/dt max | 2222.65 ± 190.07 | 2016.57 ± 140.93 * | 2036.92 ± 196.10 | 1740.02 ± 114.39 * |
| dp/dt min | -2293.20 ± 126.42 | -1783.7 ± 174.44 * | -2293.73 ± 182.68 | -1812.59 ± 240.17 * |

\* $p<0.05$ from baseline

Figure 33

MONITORING AND MODULATION OF PARASYMPATHETIC NERVOUS SYSTEM

CROSS-REFERENCE TO RELATED APPLICATIONS

This application is a U.S. national phase application filed under 35 U.S.C. § 371 claiming benefit to International Patent Application No. PCT/US2017/028871, filed Apr. 21, 2017, which claims priority under 35 U.S.C. § 119(e) to U.S. Provisional Patent Application No. 62/326,296 filed Apr. 22, 2016, the contents of which are incorporated by reference herein in their entirety.

STATEMENT REGARDING FEDERALLY SPONSORED RESEARCH OR DEVELOPMENT

This invention was made with Government support under Grant Number U18 EB021799, HL071830, HL098589 awarded by the National Institutes of Health. The government has certain rights in the invention.

BACKGROUND OF THE INVENTION

Atrial fibrillation (AF) affects more than three million people a year in the United States, a prevalence that is projected to reach 5.6-12.1 million by 2050 (Go A S et al., 2001, J Am Med Assoc, 285:2370-2375; Naccarelli G V et al., 2009, Am J Cardiol, 104:1534-1539). Despite such prevalence, the underlying mechanisms of AF are not fully understood. Current treatments consist of pharmacological therapies that have been combined with localized atrial catheter-based or surgical ablation (Chen P S et al., 2014, Circ Res, 114:1500-1515; Shen M J et al., 2014, Circ Res, 114:1004-1021). Ablation procedures are associated with complications such as the left atrial stiffness syndrome (Gibson D N et al., 2011, Heart Rhythm, 8:1364-1371), microembolic episodes (Schwarz N et al., 2010, Heart Rhythm, 7:1761-1767), and a risk of symptomatic or silent cerebral ischemia (Gaita F et al., 2010, Circulation, 122: 1667-1673). Such drawbacks have increased the research focus on defining specific neural and cardiac substrate interactions underlying AF and with such information evolving novel nonpharmacological therapeutic options for its management (Zipes D P., 2015, Nat Rev Cardiol, 12:68-69). Bioelectric neuromodulation therapies for A F represent a novel approach to such management. Among these, vagus nerve stimulation (VNS) (Lin Y et al., 2013, Sci World J, 2013:781084; Shen M J et al., 2011, Circulation, 123:2204-2212; Sheng X et al., 2011, J Am Coll Cardiol, 57:563-571) and spinal cord stimulation (Gibbons D D et al., 2012, Am J Physiol Regul Integr Comp Physiol, 302:R357-R364; Southerland E M et al., 2012, Auton Neurosci, 169:34-42; Wang S et al., 2015, Heart Rhythm, 12:1628-1635) target various aspects of the cardiac neuronal hierarchy to reduce the arrhythmia potential.

The cardiac nervous system includes reflex networks located in the insular cortex, brain stem, spinal cord, intrathoracic sympathetic ganglia, and the intrinsic cardiac nervous system (ICNS) (Ardell J L et al., 2016, J Physiol, 594:3877-3909; Armour J A., 2008, Exp Physiol, 93:165-176; Zucker I H et al., 2012, Heart Fail Clin, 8:87-99). It has been proposed that its ICNS component acts as the final coordinator of regional cardiac indexes, doing so under the influence of intrathoracic, spinal cord, and brain stem reflexes (Armour J A., 2008, Exp Physiol, 93:165-176). Neural activity within the ICNS is influenced by afferent (mechanosensitive, chemosensitive, and ischemia-sensitive) and efferent neuronal inputs (Armour J A., 2008, Exp Physiol, 93:165-176; Armour J A et al., 2004, Cardiac sensory neurons. In: Basic and Clinical Neurocardiology, edited by Armour J A Ardell J L. New York, N.Y.: Oxford Univ Press, 2004, p. 79-117; Zucker I H et al., 1991, Reflex Control of the Circulation. Boca Raton, Fla.: CRC). These afferent and efferent inputs are processed by local circuit neurons (LCNs) in peripheral ganglia to modulate sympathetic and parasympathetic efferent postganglionic projections to all regions of the heart (Ardell J L et al., 2016, J Physiol, 594:3877-3909; Fukuda K et al., 2015, Circ Res, 116:2005-2019; Herring N et al., 2009, Exp Physiol, 94:46-53; McAllen R M et al., 2011, J Physiol, 589:5801-5818). Neuronal imbalances within the ICNS can exert deleterious effects on cardiac function, including arrhythmia induction (Armour J A et al., 1972, Am J Physiol, 223:1068-1075; Armour J A et al., 2005, Auton Neurosci, 118:68-78; Scherlag B J et al., 2011, J Cardiovasc Transl Res, 4:35-41; Shen M J et al., 2012, Nat Rev Cardiol, 9:30-39). To date, which populations of neurons within the ICNS are so involved remains unresolved.

Therefore, there is a need in the art for an improved understanding of the role that specific neurons have in mediating AF, and there is also a need in the art for improved bioelectric cardiac therapies. The present invention addresses these needs.

SUMMARY OF THE INVENTION

In one aspect, the present invention provides a method of modulating cardiac function in a subject, comprising measuring the electrical activity of at least one intrinsic cardiac neuron; and modulating the activity of a nerve or ganglion of the parasympathetic autonomic nervous system. In one embodiment, the method comprises contacting an electrode to the nerve or ganglion of the parasympathetic autonomic nervous system; and applying at least one electrical signal to the nerve or ganglion of the parasympathetic autonomic nervous system.

In one embodiment, the nerve or ganglion of the cardiac nervous system is selected from the group consisting of the vagus nerve, spinal cord, and mediastinal nerve.

In one embodiment, the electrode is contacted to at least one of the group consisting of: cervical vagosympathetic nerve trunk, intrathoracic vagosympathetic nerve trunk, and auricular branch of vagus nerve. In one embodiment, the electrical activity of the nerve or ganglion increased by application of electrical stimulation. In one embodiment, the electrical activity of the nerve or ganglion is decreased by application of kilohertz frequency alternating current (KHFAC) or charge balanced direct current (CBDC).

In one embodiment, the method comprises contacting an electrode to the spinal cord, and applying at least one electrical signal to the spinal cord. In one embodiment, the electrical activity of the spinal cord is increased by application of electrical stimulation. In one embodiment, the electrical activity of the spinal cord is decreased by application of kilohertz frequency alternating current (KHFAC) or charge balanced direct current (CBDC).

In one embodiment, measuring of electrical activity of at least one intrinsic cardiac neuron comprises contacting a recording electrode to at least one selected from the group consisting of: atrial intrinsic cardiac ganglia and ventricular intrinsic cardiac ganglia.

In one embodiment, the method further comprises measuring of electrical activity of at least one neuron of a nodose ganglia.

In one embodiment, the method further comprises measuring cardiac electrical activity by contacting a recording electrode at least one selected from the group consisting of the atrial epicardial surface, atrial endocardial surface, ventricular epicardium, ventricular epicardium, and myocardium of the atrial or ventricular tissue.

In one embodiment, modulating the activity the activity of a nerve or ganglion of the parasympathetic autonomic nervous system is controlled by detection of a signal measured from the at least one intrinsic cardiac neuron.

In one aspect, the present invention provides a closed-loop system for modulating cardiac function comprising one or more recording electrodes for measuring the activity of at least one intrinsic cardiac neuron; and one or more stimulating electrodes for applying an electrical stimulus to a nerve or ganglion of the parasympathetic autonomic nervous system.

In one embodiment, the present invention provides a method for treating or preventing a cardiac disorder in a subject, comprising modulating the activity of at least one local circuit neuron (LCN) of the cardiac nervous system. In one embodiment, the method comprises electrical stimulation of the vagus nerve of the subject In one embodiment, the method further comprises measuring the electrical activity of at least one intrinsic cardiac neuron.

In one aspect, the present invention provides a method of monitoring multi-pole cardioneural function, comprising measuring the electrical activity of at least one intrinsic cardiac neuron; and measuring the cardiac electrical activity of the heart.

In one embodiment, the method comprises contacting at least one electrode to a location selected from the group consisting of: atrial intrinsic cardiac ganglia and ventricular intrinsic cardiac ganglia. In one embodiment, the method comprises contacting at least one electrode to the atrial epicardial surface or the atrial endocardial surface.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 3 depicts results from example experiments, showing the hemodynamic response to preemptive VNS at baseline, VNS, and post-VNS. Data reflect means±SE for heart rate (HR), left ventricular systolic pressure (LVSP), left ventricular diastolic pressure (LVEDP), and first derivative of left ventricular (LV) pressure (dp/dt) before (baseline), during, and for 1 min following vagus nerve stimulation (VNS). $P<0.01$ from baseline (*) and VNS (#).

FIG. 4A: control state where AF was induced by right-sided MNS. FIG. 4B: response when the same MNS site was stimulated 1 min following 3 min of preemptive right-sided VNS. Horizontal solid arrows delimit time of MNS nerve stimulations. Broken vertical lines (FIG. 4A) indicate duration of AF induced by MNS. Note that following RCV (FIG. 4B), MNS failed to induce AF, even when applied for a longer time period (20 seconds). IC activity correspondingly remained unchanged during and following MNS stimulation.

(FIG. 5B) impact of ipsilateral (right-sided) VNS therapy on the atrial arrhythmogenic potential to MNS, classified according to whether it prevented, blunted, or enhanced AF or exerted no effects. $P<0.05$ from baseline (*) and control (sham VNS; #).

(FIG. 6B) impact of contralateral VNS therapy on the atrial arrhythmogenic potential to MNS. Whereas LCV VNS mitigated the AF potential for 40% of MNS sites tested, in contradistinction to RCV VNS it enhanced that potential in ⅓ of MNS sites tested. *$P<0.05$ from baseline.

(FIG. 8A) evolution of effects induced by right-sided VNS therapy on the capacity of MNS to induce AF (% efficacy), as a function of time post therapy. Light gray curve represents the percentage of cases (Kaplan-Meier survival curve) in which AF duration was mitigated (shortened or prevented); dark curve indicates time effects of preemptive RCV in preventing MNS-induced AF. (FIG. 8B) similar data derived with respect to AF potential when left-sided (LCV) therapy was applied preemptively.

FIG. 9 depicts results from example experiments, demonstrating echocardiogram measurements to determine heart function. Values expressed as means±SE, with number of animals shown. Significant effect (*$P<0.05$) compared with their baseline level using repeated-measures ANOVA and significant effect (†$P<0.05$) compared with vagus nerve stimulation (VNS)-myocardial infarction (MI). LVESV, left ventricular end systolic volume; LVEF, LV ejection fraction.

FIG. 10 depicts results from example experiments, demonstrating Analysis of tissue weights in controls, MI, and VNS-MI. Values are means±SD. A Shapiro-Wilk test showed normality, and no significant effect ($P<0.05$) was found among groups using an ANOVA.

FIG. 11 depicts results from example experiments, demonstrating properties of intracardiac neurons of controls, MI, and VNS-MI. Values expressed as means±SE, with number of neurons shown. A Shapiro-Wilk test showed normality, and a significant effect (*$P<0.05$) with ANOVA is shown for resting membrane potential and input resistance, MI vs. controls and VNS-MI. AHP, after hyperpolarization.

FIG. 14A: representative examples of recordings derived from control, MI, and VNS-MI preparations when nerves were stimulated at 10 Hz. FIG. 14B: average data derived from ~20 cells for each condition. An ANOVA analysis indicated significant differences among treatments and was followed by Newman-Keuls post hoc analysis. Points are the means±SE. *$P<0.05$, control and MI vs. VNS-MI neurons.

FIG. 17 depicts results from example experiments, demonstrating cardiac hemodynamics at termination, among-group comparisons. Values are means±SE; n, number of animals. PO, pressure overload; VNS, vagus nerve stimulation; LCV and RCV, left and right cervical vagus; LVSP, left ventricular (LV) systolic pressure; LVEDP, LV end-diastolic pressure; LV +dp/dt and LV −dp/dt, rate of change of LV developed pressure; HR, heart rate. #$P<0.05$ vs. RCV; *$P<0.05$ vs. sham VNS.

FIG. 18 depicts results from example experiments, demonstrating analysis of heart and lung weight in controls and PO, LCV-PO, and RCV-PO animals. Values are means±SD; n, number of animals. No significant effect ($P<0.05$) was found between groups (by ANOVA).

FIG. 19 depicts results from example experiments, demonstrating soma properties of intrinsic cardiac neurons derived from controls and PO, RCV-PO, and LCV-PO animals. Values are means±SE; n, number of neurons. RMP, resting membrane potential; AHP, afterhyperpolarization. *Significant effect (P<0.05) vs. other groups (by ANOVA).

FIG. 20A), LV volume (FIG. 20B), cardiac output (FIG. 20C), heart rate (FIG. 20D), and stroke volume (FIG. 20E). *P<0.05 vs. baseline; #P<0.05 vs. sham VNS.

FIG. 21A: representative Masson's trichrome-stained sections of LV tissue from control and PO hearts. FIG. 21B: histomorphometric quantification of myocyte cross-sectional areas of experimental tissues. PO leads to greater myocyte cross-sectional area (*P<0.05). Hypertrophy was significantly reduced (#P<0.05) in RCV-treated PO tissue compared with sham VNS PO-treated tissue. Con, control.

FIG. 25A: representative Western blots showing pGS and total GS protein levels in control (n=7), PO (n=7), PO with right vagus stimulation (PO-RCV, n=7), and PO with left vagus stimulation (PO-LCV, n=3) heart extracts. Blot stained with Ponceau S (Pon.s) is shown as a protein-loading control. FIG. 25B and FIG. 25C: densitometry analysis of pGS and total GS protein band intensity for all Western blots. *P<0.05, Con vs. all PO; #P<0.05, PO+LCV vs. PO-RCV and PO+sham (by ANOVA followed by Newman-Keuls post hoc analysis). FIG. 25D: ratio of pGS to GS band intensities. *P<0.05, Con vs. all PO (by ANOVA followed by Newman-Keuls post hoc analysis).

FIG. 26A: representative Western blots probed for pAkt and pBAD proteins in control (Con), PO+LCV, PO+RCV, and PO+sham (n=5) heart extracts. Total BAD protein levels are also shown. Ponceau S (Pon.s) staining is shown as a protein-loading control. FIG. 26B and FIG. 26C: densitometry analysis of pBAD and total BAD protein band intensity for all Western blots. *P<0.05, PO+sham vs. Con, PO+LCV, and PO+RCV (by ANOVA followed by Newman-Keuls post hoc analysis). FIG. 26D: ratio of pBAD to BAD. No significant difference was observed. FIG. 26E: densitometry analysis of pAkt protein level (n=4). *P<0.05, Con vs. all PO; #P<0.05, PO+LCV vs. PO+RCV and PO+sham.

FIG. 27A: representative terminal deoxynucleotide transferase-mediated nick-end labeling (TUNEL) in CardioTACS-stained sections of LV tissue from control (FIG. 27A.a) and PO-treated (PO+sham (FIG. 27A.b), PO+RCV (FIG. 27A.c), and PO+LCV (FIG. 27A.d)) hearts. Arrows indicate blue-stained nuclei, indicative of DNA fragmentation, a hallmark of apoptosis. FIG. 27B: quantification of apoptotic cells in experimental groups shown in A. *P<0.05 vs. all PO.

(FIG. 28A and FIG. 28B respectively) Low and high magnification views, respectively, of S100-positive satellite cells surrounding neurons in the canine nodose ganglion. (FIG. 28C and FIG. 28D) Immunostaining for synaptophysin shows a lack of synapses in the nodose ganglion (FIG. 28C) and an abundance of synapses in the stellate ganglion. Scale bar is 50 µm in FIG. 28A, FIG. 28C and FIG. 28D and 25 µm in FIG. 28B.

(FIG. 30A) Percentage of cardiac-related nodose ganglion sensory neurons that responded significantly to touching the right or left ventricles (Touch), inferior vena cava occlusion (IVC), descending aortic occlusion (AO), left anterior descending (LAD) coronary artery occlusion or ventricular epicardial application of veratridine applied to sensory fields identified by epicardial touch. 66% of cardiac related sensory neurons responded to LAD CAO. (FIG. 30B) Interdependent afferent neuronal responses among identified ventricular afferent neurons in response to these various stressors. Thickness of arrows is proportional to the strength of conditional probability so identified. Arrows with the conditional probability of 0.6 and above only are shown in the figure.

(FIG. 32A) Dashed vertical lines represent the onset and termination of 2 Hz VNS in a representative animal. Dashed lines also indicate transition point to higher intensity levels of VNS (2 to 7 mA); maximal activity found at 5 mA with abrupt fall of at intensity levels about that point. (FIG. 32B) Summary (n=13) of changes in nodose activity as VNS intensity is increased from 1-8 mA at 2 Hz. Activity of cardiac sensory neurons increased with progressive VNS intensity up to ~5 mA. At VNS intensities above 5 mA, neural activity decreased, almost being absent when stimulation intensity reached 6-7 mA. (*$p<0.05$ from the baseline: BL).

FIG. 33 depicts results from example experiments, demonstrating hemodynamic responses to transient (1 min) LAD CAO. Data reflects mean±SE for heart rate (HR), left ventricular systolic (LVSP), left ventricular end diastolic pressure (LVEDP), as well as the maximum and minimum first derivatives of LV pressure (dp/dt) prior to (baseline) and during LAD CAO. *$p<0.01$ comparison from baseline (BL).

DETAILED DESCRIPTION

Figure 1:
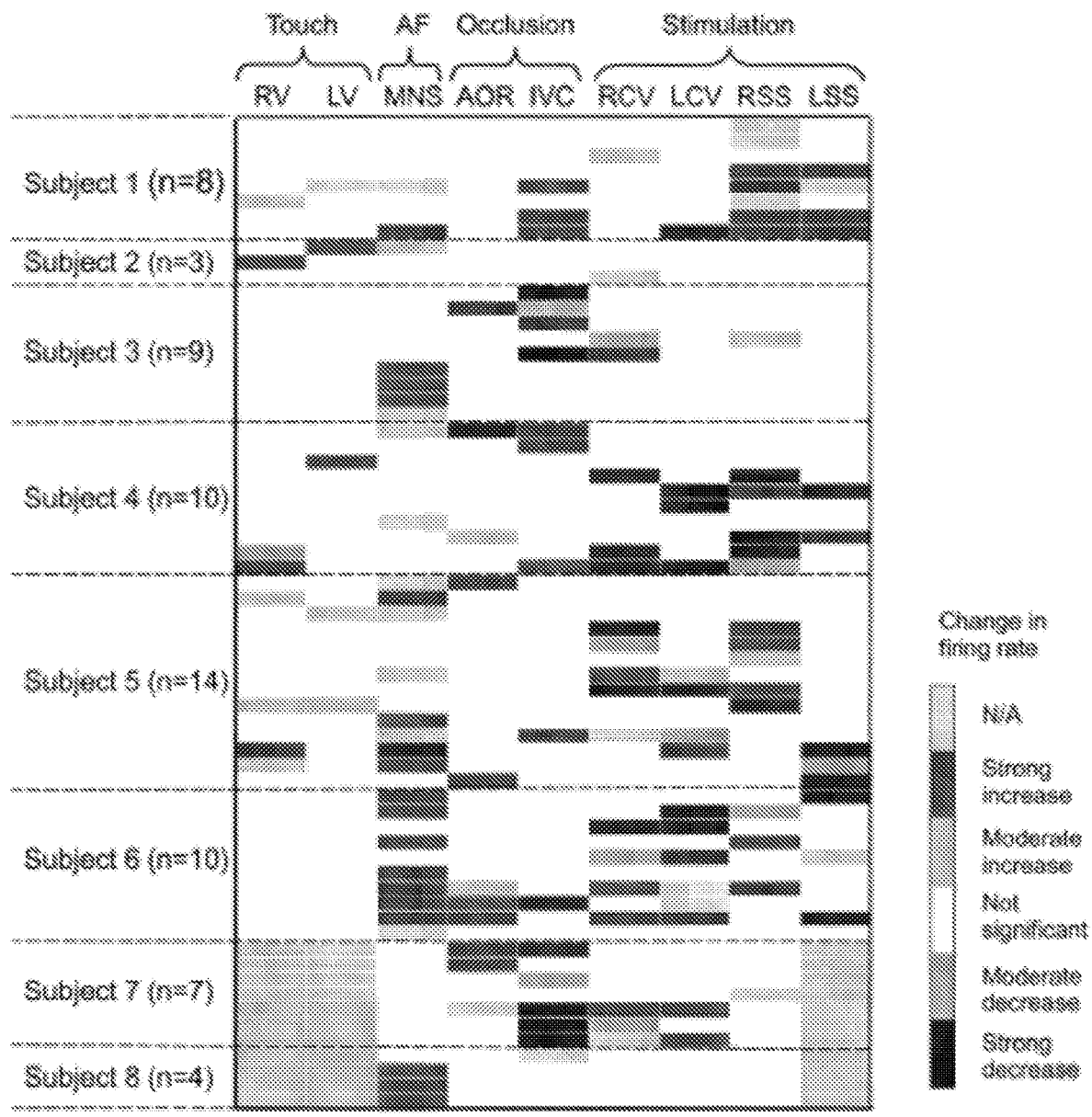
FIG. 1 depicts results from example experiments, showing intrinsic cardiac (IC) neurons classified based on their functional responses to afferent stressor (touch of right (RV) or left (LV) ventricle; occlusion of descending aorta (AOR) or inferior vena cava (IVC)) vs. efferent stressor (right (RCV) or left (LCV) cervical vagus or stellate ganglia (right (RSS); left (LSS)) electrical stimulation) interventions. In response to stressors, IC firing could either increase (green bars) or decrease (red bars), with that individual response being stable over time. Gray bars mean a specific test was not done for that neuron (designated N/A). Afferent-related IC neurons were defined as those that responded differentially to at least one of the following stressors: RV, LV, AOR, or IVC. Efferent-related IC neurons responded to cervical vagal and/or stellate ganglion stimulation. Convergent IC neurons were modulated by both afferent and efferent inputs. Note that 11 IC neurons (~13%) responded solely to the mediastinal nerve stimulation (MNS) stressor. Approximately 27% of spontaneously identified IC neurons were unaffected by any stressors tested; as such, they are defined as unknown and are not shown in this panel.

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present invention provides compositions, devices, systems, and methods for monitoring and modulating cardiac function and dysfunction in a subject. For example, in certain aspects, the present invention provides for monitoring cardiac autonomic function and modulating parasympathetic control of cardiac function. In certain aspects, the present invention provides for a closed-loop neuromodulation system which can monitor cardiac autonomic activity and modulate parasympathetic control of cardiac function based upon detected cardiac autonomic activity or pattern of activity.

In one aspect, the present invention provides a method for monitoring cardiac autonomic function, comprising inserting an electrode(s) into the intrinsic cardiac ganglia and recording extracellular neural activity. For example, in one embodiment, the electrode(s) is/are placed in atrial intrinsic cardiac ganglia. In one embodiment, the electrode(s) is/are placed in ventricular intrinsic cardiac ganglia. In one embodiment, the electrode(s) is/are placed from epicardial access. In one embodiment, the electrode(s) is/are placed from vascular access.

In one aspect, the present invention provides a method for monitoring multi-pole cardioneural function, comprising inserting an electrode(s) onto the surface of the atrium (or into the atrium) and electrode(s) into the intrinsic cardiac ganglia for recording cardiac electrical and autonomic neural activity. In one embodiment, the electrode(s) is/are placed in atrial intrinsic cardiac ganglia. In one embodiment, the electrode(s) is/are placed in ventricular intrinsic cardiac ganglia. In one embodiment, the electrode(s) is/are placed on the atrial epicardial surface. In one embodiment, the electrode(s) is/are placed on the atrial endocardial surface. In one embodiment, the electrode(s) is/are placed within the atrial myocardium. In one embodiment, the electrode(s) is/are placed from epicardial access. In one embodiment, the electrode(s) is/are placed from vascular access.

In one aspect, the present invention provides a method for closed loop modulation of peripheral autonomic ganglia, comprising inserting an electrode(s) on the 10th cranial nerve and stimulating as determined by recorded cardioneural activity. In one embodiment, the stimulating electrode(s) is/are placed on the cervical vagosympathetic nerve trunk. In one embodiment, the stimulating electrode(s) is/are placed on the intrathoracic vagosympathetic nerve trunk. In one embodiment, the stimulating electrode(s) is/are placed on the cervical vagosympathetic nerve trunk. In one embodiment, the stimulating electrodes is/are placed for cutaneous stimulation of the auricular branch of the 10th cranial nerve. In one embodiment, nerve activity is increased by electrical stimulation. In one embodiment, nerve activity is decreased by kilohertz alternating current. In one embodiment, nerve activity is decreased by charge-balance direct current. In one embodiment, the recording electrode(s) is/are placed in atrial intrinsic cardiac ganglia. In one embodiment, the recording electrode(s) is/are placed in ventricular intrinsic cardiac ganglia. In one embodiment, wherein the recording electrode(s) is/are placed on the atrial epicardial surface. In one embodiment, the recording electrode(s) is/are placed on the atrial endocardial surface. In one embodiment, the recording electrode(s) is/are placed within the atrial myocardium. In one embodiment, the recording electrode(s) is/are placed from epicardial access. In one embodiment, the recording electrode(s) is/are placed from vascular access. In one embodiment, the stimulating nerve electrodes are controlled by neural activity recorded from intrinsic cardiac ganglia. In one embodiment, the stimulating electrode(s) is/are controlled by electrical activity recorded from the atrium. In one embodiment, the stimulating electrode(s) is/are controlled by concurrent cardioneural activity from the atrium and intrinsic cardiac ganglia.

In one embodiment, the invention relates to monitoring the activity of the intrinsic cardiac nervous system (ICNS) and modulating the activity of the ICNS. For example, in certain embodiments, modulating the activity of the ICNS can be used to treat or prevent atrial fibrillation (AF), ventricular arrhythmia, ventricular tachycardia, systolic heart failure (reduced ejection heart failure), diastolic heart failure (preserved ejection heart failure), or hypertension in a subject in need thereof. In certain embodiments, modulating the activity of the ICNS can exert anti-adrenergic effects to reduce excessive sympathetic input to the heart.

In certain aspects, the invention relates to modulation of local circuit neurons (LCNs) of the intrinsic cardiac nervous system (ICNS). For example, it is described herein that neutrally induced AF results in the enhanced activity of LCNs and that modulation of LCN activity can attenuate AF. Further, it is demonstrated herein that the antiarrhythmic effects of the modulation of LCN activity has memory, such that the effects persist for an extended period of time. In certain embodiments, the invention provides for treating or preventing AF by modulating the activity of one or more neurons of the ICNS. For example, in one embodiment, the activity of one or more LCNs are modulated. In one embodiment, the activity of one or more afferent LCNs are modulated. In one embodiment, the activity of one or more efferent LCNs are modulated. In one embodiment, the activity of one or more convergent LCNs are modulated.

Modulation of ICNS or LCN activity may be carried out using any method known in the art. For example, in certain embodiments, the invention comprises modulating ICNS or LCN activity by administering a small molecule, drug, or other chemical or biological material that modulates ICNS or LCN activity. In certain embodiments, the invention comprises modulating ICNS or LCN activity by administering an electrical stimulus that modulates ICNS or LCN activity. For example, in certain embodiments, an electrical stimulus is applied to cardiac tissue or extracardiac input. Exemplary extracardiac inputs that can modulate ICNS LCN activity, include, but is not limited to the vagus nerve (10th cranial nerve), stellate ganglia, middle cervical ganglia, or mediastinal ganglia.

In one embodiment, the invention relates to modulating the activity of the one or more peripheral autonomic ganglia. For example, in certain embodiments, modulating the activity of one or more peripheral autonomic ganglia can be used to treat or prevent treat or prevent atrial fibrillation (AF), ventricular arrhythmia, ventricular tachycardia, systolic heart failure (reduced ejection heart failure), diastolic heart failure (preserved ejection heart failure), or hypertension in a subject in need thereof. In certain embodiments, modulating the activity of one or more peripheral autonomic ganglia can exert anti-adrenergic effects to reduce excessive sympathetic input to the heart.

Modulation of peripheral autonomic ganglia activity may be carried out using any method known in the art. For example, in certain embodiments, the invention comprises modulating peripheral autonomic ganglia activity by administering a small molecule, drug, or other chemical or biological material that modulates peripheral autonomic ganglia activity. In certain embodiments, the invention comprises modulating peripheral autonomic ganglia activity by administering an electrical stimulus that modulates peripheral autonomic ganglia activity. For example, in certain embodiments, an electrical stimulus is applied to cardiac tissue or extracardiac input. Exemplary extracardiac inputs that can modulate peripheral autonomic ganglia activity, include, but is not limited to the vagus nerve and paravertebral ganglia.

In one embodiment, the invention relates to monitoring the activity of nodose ganglia and modulating the activity of the nodose ganglia. For example, in certain embodiments, modulating the activity of the nodose ganglia can be used to treat or prevent atrial fibrillation (AF), ventricular arrhythmia, ventricular tachycardia, systolic heart failure (reduced ejection heart failure), diastolic heart failure (preserved ejection heart failure), or hypertension in a subject in need thereof. In certain embodiments, modulating the activity of the nodose ganglia can exert anti-adrenergic effects to reduce excessive sympathetic input to the heart. For example, it is described herein that vagus nerve stimulation results in the enhanced activity of nodose neurons at lower intensity and suppression of nodose neurons at higher intensity, and that nodose processing of afferent information can be modified. Modulation of nodose ganglia activity may be carried out using any method known in the art. For example, in certain embodiments, the invention comprises modulating nodose ganglia activity by administering a small molecule, drug, or other chemical or biological material that modulates nodose ganglia activity. In certain embodiments, the invention comprises modulating nodose ganglia activity by administering an electrical stimulus that modulates nodose ganglia activity. For example, in certain embodiments, an electrical stimulus is applied to cardiac tissue or extracardiac input. Exemplary extracardiac inputs that can modulate nodose ganglia activity, include, but is not limited to the vagus nerve and spinal cord.

In one embodiment, the method comprises providing an electrical stimulus to the vagus nerve, which thereby modulates parasympathetic autonomic activity. In certain embodiments, the method comprises providing an electrical stimulation to the cervical vagosympathetic nerve trunk, intrathoracic vagosympathetic nerve trunk, or the auricular branch of the vagus nerve.

In one embodiment, the method comprises providing an electrical stimulus that increases activity in the vagus nerve. In one embodiment, the method comprises providing an electrical stimulus that inhibits or decreases activity the vagus nerve.

In one embodiment, the method comprises contacting one or more stimulating electrodes to the vagus nerve and applying vagus nerve stimulation (VNS). In certain embodiments, VNS can be applied to modulate parasympathetic autonomic activity, and treat or prevent cardiac dysfunction.

In one embodiment, VNS is applied at about 1 Hz-50 Hz. In one embodiment, VNS is applied at about 5 Hz-30 Hz. In one embodiment, VNS is applied at about 5 Hz-10 Hz. In one embodiment, VNS is applied at about 10 Hz-20 Hz.

In one embodiment, VNS is applied with a pulse width of about 0.1-1000 µs. In one embodiment, VNS is applied with a pulse width of about 1-500 µs. In one embodiment, VNS is applied with a pulse width of about 100-500 µs. In one embodiment, VNS is applied with a pulse width of about 250-500 µs. In one embodiment, VNS is applied with a pulse width of about 130 µs.

In one embodiment, VNS is applied with a current of about 0.1-10 mA. In one embodiment, VNS is applied with a current of about 0.5-5 mA. In one embodiment, VNS is applied with a current of about 1-2 mA. In one embodiment, VNS is applied with a current of about 0.6-3.5 mA.

In one embodiment, the method comprises providing an electrical stimulus to the spinal cord, which thereby modulates parasympathetic autonomic activity of, for example, the nodose ganglion. In certain embodiments, the method comprises providing an electrical stimulation to the T1-T4 dorsal column of the spinal cord or the C1-C2 dorsal column of the spinal cord.

In one embodiment, the method comprises providing an electrical stimulus that increases activity in the spinal cord. In one embodiment, the method comprises providing an electrical stimulus that inhibits or decreases activity the spinal cord.

In one embodiment, the method comprises contacting one or more stimulating electrodes to the spinal cord and applying spinal cord stimulation (SCS). In certain embodiments, SCS can be applied to modulate parasympathetic autonomic activity, and treat or prevent cardiac dysfunction.

In one embodiment, SCS is applied at about 1 Hz-100 Hz. In one embodiment, SCS is applied at about 5 Hz-75 Hz. In one embodiment, SCS is applied at about 10 Hz-50 Hz.

In one embodiment, SCS is applied with a pulse width of about 0.1-1000 µs. In one embodiment, SCS is applied with a pulse width of about 1-500 µs. In one embodiment, SCS is applied with a pulse width of about 100-500 µs.

In one embodiment, SCS is applied with a current of about 0.1-10 mA. In one embodiment, SCS is applied with a current of about 0.5-5 mA. In one embodiment, SCS is applied with a current of about 1-2 mA.

In one embodiment, the method comprises decreasing activity in a nerve by administering high frequency alternating current (HFAC) or kilohertz frequency alternating current (KHFAC) to an upstream input, for example the vagus nerve or spinal cord.

In one embodiment, KHFAC is applied at about 5 kHz-30 kHz. In one embodiment, KHFAC is applied at about 10 kHz-25 kHz. In one embodiment, KHFAC is applied at about 15 kHz-20 kHz.

In one embodiment, KHFAC is applied at a voltage of about 5-30 volts. In one embodiment, KHFAC is applied at a voltage of about 10-25 volts. In one embodiment, KHFAC is applied at a voltage of about 15-20 volts.

In one embodiment, the method comprises decreasing the activity in a nerve by administering charged balanced direct current (CBDC) to an upstream input, for example the vagus nerve, spinal cord, intrathoracic nerves exiting the vagosympathetic nerve trunk, ansae subclavia, and paravertebral ganglia. For example, in certain embodiments, the method comprises use of a CBDC carousel electrode comprising a plurality of nodes that each deliver temporally offset pulses to the nerve, such that the carousel electrode delivers a substantially constant DC charge to the nerve. In one embodiment, CBDC is delivered at a current of about 0.05 to 10 mA. In one embodiment, CBDC is delivered at a current of about 0.1 to 4 mA.

In certain embodiments, modulation of parasympathetic control of the cardiac function or dysfunction, as described herein, is triggered by a signal derived from the monitoring of cardiac autonomic activity and/or cardiac electrical activity. For example, in certain aspects, the method comprise detecting a signal, pattern, or signature indicative of the need for therapeutic intervention; and modulating the parasympathetic activity by way of a drug or electrical intervention.

In certain embodiments, the invention comprises a method of monitoring cardiac autonomic activity. For example, in certain aspects, the method comprises measuring the activity of one or more of: intrinsic cardiac nervous system (ICNS), local circuit neurons (LCNs), atrial intrinsic cardiac ganglia, ventricular intrinsic cardiac ganglia, nodose ganglia, mediastinal ganglia, middle cervical ganglia, stellate ganglia, and dorsal root ganglia. For example, in certain embodiments, the method comprises contacting, placing, or inserting one or more recording electrodes at one or more recording sites, including, but not limited to, intrinsic cardiac nervous system (ICNS), local circuit neurons (LCNs), atrial intrinsic cardiac ganglia, ventricular intrinsic cardiac ganglia, ventral interventricular ganglionated plexus (VIV GP), dorsal interventricular glanglionated plexus (DIV GP), right marginal artery ganglionated plexus, right atrial ganglionated plexus, nodose ganglia, mediastinal ganglia, middle cervical ganglia, stellate ganglia, and dorsal root ganglia.

In certain embodiments, the method comprises monitoring cardiac electrical activity. For example, in certain embodiments, the method comprises contacting, placing or inserting one or more recording electrodes on or in a location of the heart, including but not limited to atrial epicardial surface, atrial endocardial surface, ventricular epicardial surface, ventricular endocardial surface. In certain embodiments, the method comprises inserting electrodes into the myocardial wall within the atria or ventricles.

In certain embodiments, the method comprises monitoring multi-pole cardioneural function by measuring cardiac electrical activity and autonomic neural activity. For example, in certain embodiments, the method comprises contacting, placing, or inserting one or more recording electrodes on or in a location of the heart; and contacting, placing, or inserting one or more electrodes at one or more non-cardiac recording sites, including, but not limited to, intrinsic cardiac nervous system (ICNS), local circuit neurons (LCNs), atrial intrinsic cardiac ganglia, ventricular intrinsic cardiac ganglia, nodose ganglia, mediastinal ganglia, middle cervical ganglia, stellate ganglia, and dorsal root ganglia.

The recording electrode(s) may be any suitable type and size electrode for detecting electrical signals in the heart or autonomic nervous system. Exemplary electrodes include, but are not limited to, single shank electrodes, 2D multi-shank electrodes, 3D multi-shank electrodes, and multielectrode arrays. In one embodiment, the method comprises the use of an implantable or partially implantable sensor incorporating a plurality of electrodes for detecting electrical. For example, in one embodiment, the sensor comprises a linear microelectrode array (LMA). In certain embodiments, the LMA comprises a plurality of electrodes. For example, in one embodiment, the LMA comprises 16 platinum/iridium electrodes. The electrodes may be placed at their desired recording sites using any suitable method, including, but not limited to, vascular access, epicardial access, and surgical access In certain embodiments, the method comprises monitoring the cardiac electrical activity and/or cardiac autonomic activity under basal or resting conditions. In certain aspects, the method comprises monitoring the cardiac electric activity and/or cardiac autonomic activity as the subject carries on day to day tasks, including, but not limited to, sleeping, eating, working, walking, and the like. In certain aspects, the method comprises monitoring the cardiac electric activity and/or cardiac autonomic activity in response to a stimulus, including but not limited to, exercise, epicardial mechanical stimulation, endocardial mechanical stimulation, changes in preload or afterload, thermal stress, orthostatic stress, mental stress, electrical stimulation of the sympathetic nervous system, electrical stimulation of the parasympathetic nervous system, administration of a biologic or chemical treatment, or the like In certain embodiments, the method comprises monitoring activity for a given duration to detect a pattern of activity or to detect the presence or frequency of abnormal activity. In certain aspects, the monitored or measured activity can be referred to as a neural signature. The neural signature may be indicative of cardiac function or dysfunction, or the risk of cardiac dysfunction. In one exemplary embodiment, a monitored neural signature may be compared to a baseline or reference signature. Baseline or reference neural signatures may be patient specific, or they may be collective or pooled data representative of average values for subjects having at least one characteristic in common. Exemplary characteristics may include patient gender, age, activity level, diet, congenital defect, genetic trait, metabolic status, and the like. In certain embodiments, the baseline or reference neural signature is defined with respect to one or more cardiovascular stressors, including, but not limited to, exercise, orthostatic stress, temperature, Valsalva maneuver, and spirometry test. After establishing a baseline or reference neural signature representative of a healthy state, subsequent measurements of cardiac electrical activity and/or cardiac autonomic activity are taken to establish a real-time neural signature for comparison to the baseline or reference, such that a determination can be made as to whether the subject is in need of a treatment.

As contemplated herein, the neural signature may include one or more parameters, including without limitation, parameters relating to spontaneous firing rate, activity during cardiac cycle phases, temporal relationships between neurons, response to mechanosensitive input, change in cardiac loading conditions, response to epicardial pacing, chemoreceptor and nociceptive input. For each parameter, a threshold value may be established that is indicative of a subject in need of a treatment, or of a particular type of treatment. In certain embodiments, exceeding only one threshold value may be determinative of a need for treatment and/or type of treatment, whereas in other embodiments, multiple threshold values may be exceeded in order to be determinative of a need for treatment, or particular type of treatment. In still other embodiments, a scoring algorithm may be used to determine whether the differences in neural signature comparisons is demonstrative of a need for treatment, or of a particular type of treatment. In certain embodiments, scoring includes changes in individual or grouped activity, directionality of changes in such activity and temporal relationships between 2 or more neurons The method may be used to diagnose a cardiac condition, assess the recovery of a cardiac condition, assess the efficacy of a therapy of a cardiac condition, determine the likelihood of a future cardiac event, or determine that a prior cardiac event has occurred.

Exemplary cardiac conditions or events detected or monitored by way of the presently described method includes, but is not limited to ischemic heart disease, myocardial infarction, premature ventricular contraction, arrhythmia, reduced ejection heart failure, preserved ejection heart failure, atrial fibrillation, ventricular tachycardia, and the like.

In certain embodiments, the method comprises determining the number or percentage of intrinsic cardiac neurons that are afferent, efferent, or convergent neurons. In certain embodiments, the number or percentage of afferent neurons can be assessed by determining which neurons transduce a response to mechanical stimuli of myocardial tissue, change in preload (i.e., by transient IVC occlusion), or change in afterload (i.e., by transient occlusion of the descending aorta). In certain embodiments, the method comprises identifying which neurons transduce a response to mechanical stimuli at various locations, for example stimuli in the infarct region, border zone, and remote regions. Mechanical stimuli may be generated by a applying a force to the myocardial tissue, which may be generated by a blunt object (i.e., electrode, needle, or catheter) or by flow of a liquid or gas on to the tissue. In certain embodiments, the numbers or percentage of afferent neurons can be assessed by determining which neurons transduce a chemical stimuli delivered in proximity to the sensory field of the recorded neuron(s). For example, suitable chemicals may be delivered by catheter or needle to focal areas of myocardial tissue or intrinsic cardiac ganglia.

In certain embodiments, the number or percentage of efferent neurons can be assessed by determining which neurons transduce an electrical stimuli delivered to upstream parasympathetic or sympathetic inputs, including but not limited to stimuli to the vagus, stellate ganglia, middle cervical ganglia, or mediastinal ganglia. The delivered stimuli may be of any intensity, frequency, or duration, known to be transduced by typical efferent intrinsic cardiac neurons.

In one embodiment, activity of intrinsic cardiac neurons can increase at rest or in response to cardiovascular stressors when associated with myocardial infarction. In one embodiment, activity can decrease at rest or in response to cardiovascular stressors when associated with myocardial infarction. In another embodiment, activity can increase in a subset of cardiac neurons, can decrease in a subset of cardiac neurons, and remain unaltered in a subset of cardiac neurons. These changes are reflective of the types of neurons being recorded from (afferent, efferent or convergent neurons), the characteristics of the stressor imposed (e.g. mechanical, chemical, nociceptive), and the structure/function of the nerve/myocyte remodeling in heart disease.

In one embodiment, the temporal relationship of cardiac neurons to the cardiac cycle can change with myocardial infarction. This can include those neurons who activity is temporally related to diastole (cardiac relaxation), systole (ejection phase) and isovolumetric contraction and relaxation.

In one embodiment, the temporal relationship of one cardiac neuron to another can change with myocardial infarction. This temporal relationship may include cardiac neurons on one functional class (e.g. afferent related) or may extend across classes (afferent to efferent, afferent to convergent, efferent to afferent and efferent to convergent).

For example, in one embodiment, the spontaneous firing rate may demonstrate a drop of at least 5% when associated with myocardial diseased tissue. In other embodiments, the spontaneous firing rate may demonstrate varying degrees of changes, for example a drop of at least 10%, at least 15%, at least 20%, at least 25%, at least 30%, and even at least 35% or more, when associated with myocardial diseased tissue. In one embodiment, neuron activity during cardiac cycle phases may demonstrate a drop of at least 5% during diastolic-related activity when associated with myocardial diseased tissue. In other embodiments, neuron activity during cardiac cycle phases may demonstrate a drop of at least 10%, at least 15% or even at least 20% or more during diastolic-related activity when associated with myocardial diseased tissue. In another embodiment, neuron activity during cardiac cycle phases may demonstrate an increase of at least 5% during systolic-related activity when associated with myocardial diseased tissue. In other embodiments, neuron activity during cardiac cycle phases may demonstrate an increase of at least 10%, at least 15%, at least 20%, at least 25%, at least 30%, at least 35%, at least 40%, at least 45%, or even at least 50% or more during systolic-related activity when associated with myocardial diseased tissue. In another embodiment, neuron activity during cardiac cycle phases may demonstrate a drop of at least 5% in dual diastolic- and systolic-related activity when associated with myocardial diseased tissue. In other embodiments, neuron activity during cardiac cycle phases may demonstrate a drop of at least 10%, at least 20%, at least 30%, at least 40%, or even at least 50% or more in dual diastolic- and systolic-related activity when associated with myocardial diseased tissue.

In one embodiment, the response to mechanosensitive input may demonstrate a drop of at least 5% when associated with myocardial diseased tissue. In other embodiments, the response to mechanosensitive input may demonstrate a drop of at least 10%, at least 15%, at least 20%, at least 25%, at least 30%, at least 35%, at least 40%, at least 45%, and even at least 50% or more, when associated with myocardial diseased tissue.

In another embodiment, the ability of neurons to transduce changes in cardiac loading conditions may include a drop in neural response to a decrease in preload conditions by at least 5% when associated with myocardial diseased tissue. In other embodiments, the ability neurons to transduce changes in cardiac loading conditions may include a drop in neural response to a decrease in preload conditions by at least 10%, at least 15%, at least 20%, at least 25%, at least 30%, and even at least 35% or more, when associated with myocardial diseased tissue.

In another embodiment, the response to epicardial pacing may include an upregulation of pacing-responsive convergent neurons associated with myocardial diseased tissue. In yet another embodiment, the response to epicardial pacing may include a downregulation of pacing-responsive afferent neurons associated with myocardial diseased tissue.

In one aspect, the present invention provides a system for monitoring autonomic and cardiac activity and modulating parasympathetic activity. For example, in certain embodiments, the system is a closed-loop system comprising one or more recording electrodes and one or more stimulating electrodes. In one embodiment, the system comprises a control unit that receives input from the recording electrodes and delivers input to the stimulating electrodes. For example, in certain embodiments, the recording electrodes detect a signal or signal, the control unit processes the signal or signals to determine the activity or pattern of activity at the recording site, and, when applicable, the control unit communicates with the stimulating electrodes to deliver a stimulus.

The system may include at least one recording electrode, including, but not limited to single shank electrodes, 2D multi-shank electrodes, 3D multi-shank electrodes, and multielectrode arrays, to monitor electrical signals from the ICNS, LCNs, atrial intrinsic cardiac ganglia, ventricular intrinsic cardiac ganglia, nodose ganglia, and the like. In one embodiment, the system comprises an implantable or partially implantable sensor incorporating a plurality of electrodes for detecting electrical signals generated by intrinsic cardiac neurons. For example, in one embodiment, the sensor comprises a linear microelectrode array (LMA). In certain embodiments, the LMA comprises a plurality of electrodes. For example, in one embodiment, the LMA comprises 16 platinum/iridium electrodes. In one embodiment, the LMA comprises multiple shank electrodes in 2D or 3D configurations. The sensor may comprise any suitable type and size of electrode suitable for detecting electrical signals.

These electrodes may be designed for insertion into (or to make contact with) the intrinsic cardiac neurons or ganglia of a subject to effectively detect electrical activity of the neurons for recording at a control unit connected to the electrodes. While the electrodes are implantable in a subject, the control unit may either be implantable in the subject or external to the subject, as desired.

In one embodiment, the system may comprise one or more pre-amplifiers, amplifiers, or filters to process the detected electrical signal. Such components may be positioned on an implanted sensor, or alternatively be present on external hardware. For example, in one embodiment, the preamplifier provides for low and high pass filtering with gain control. In one embodiment, the filtering range is 300 to 3 KHz with gain up to 5K. In certain embodiments, the filtering range and/or gain of the preamplifier is adjustable to optimize signal to noise ratio. In one embodiment, the preamplifier and control device allow for transient blocking of input signal as related to electrical stimuli or electrical activity generated by atrial or ventricular tissues.

In one embodiment, the system comprises a an implantable or external control unit, which may be powered by any method understood in the art, including a standard battery, standard wiring for external power transfer, or it may include a receiver coil for wireless power transfer. The control unit may include a microprocessor and any form of memory for storing control software and any received and/or processed data. The control unit may further include a transceiver or any hardware and software necessary for transmitting and/or receiving data with an external processing unit for further analysis of the recorded activity within each neuron being measured. The external processing unit may be one or more computing units, and may be or include any type of computing device including a desktop laptop, tablet, smartphone or other wireless digital/cellular phones, wrist watches, televisions or other thin client device as would be understood by those skilled in the art. Generally, any computing devices described herein may include at least one processor, standard input and output devices, as well as all hardware and software typically found on computing devices for storing data and running programs, and for sending and receiving data over a network, if needed. It should also be appreciated that the recorded data may be further filtered (such as, amplified or any other type of additional processing for analyzing and displaying the data as desired by the external processing unit or other connected computing device within the system.

In certain embodiments, the system of the invention comprises one or more components to stimulate a parasympathetic input, including, but not limited to, the vagus nerve, mediastinal verve, spinal cord, and intrinsic cardiac ganglia. In certain embodiments, the system comprises one or more stimulatory electrodes to apply an electrical signal to the parasympathetic nervous system, used to stimulate the efferent intrinsic cardiac neurons. Exemplary electrodes include cuff electrodes, needle electrodes, flat interface electrodes, intrafasicular electrodes, glass suction electrodes, paddle electrodes, bipolar hemi-cuff electrodes, bipolar hook electrodes, percutaneous cylindrical electrodes, and the like. The electrodes may be monopolar, bipolar, tripolar, quaripolar, or having five or more poles. The electrodes may be fabricated from, or be partially or entirely coated with, a high charge capacity material such as platinum black, iridium oxide, titanium nitride, tantalum, poly(elthylenedioxythiophene) and suitable combinations thereof. An electrode suited for delivery of HFAC or KHFAC is described in U.S. Patent Publication US2011/0125216. In certain embodiments, the system comprises a carousel electrode, which is suited for delivery of CBDC, as described in US2015/0174397.

In certain embodiments, the system comprises one or more pulse generators coupled to one or more electrodes to provide electrical stimulation. The pulse generators may be implantable or external to the subject.

In one embodiment, the system comprises one or more pacing electrodes suitable for application of cardiac electrical stimulation at one or more epicardial or endocardial sites.

The system may further include a software platform with a graphical user interface (GUI) for modulating the function of the one or more sensors, pulse generators, and/or electrodes and for displaying information regarding the historical or real-time electrical activity of the measured neurons or ganglia, as well as historical or real-time measurement of the subject's cardiac function. In certain embodiments, the wireless communication information transfer to and from the sensor control unit and the external processing unit may be via a wide area network and may form part of any suitable networked system understood by those having ordinary skill in the art for communication of data to additional computing devices, such as, for example, an open, wide area network (e.g., the internet), an electronic network, an optical network, a wireless network, a physically secure network or virtual private network, and any combinations thereof. Such an expanded network may also include any intermediate nodes, such as gateways, routers, bridges, internet service provider networks, public-switched telephone networks, proxy servers, firewalls, and the like, such that the network may be suitable for the transmission of information items and other data throughout the system.

As would be understood by those skilled in the art, the external processing unit may be wirelessly connected to the expanded network through, for example, a wireless modem, wireless router, wireless bridge, and the like. Additionally, the software platform of the system may utilize any conventional operating platform or combination of platforms (Windows, Mac OS, Unix, Linux, Android, etc.) and may utilize any conventional networking and communications software as would be understood by those skilled in the art.

To protect data, an encryption standard may be used to protect files from unauthorized interception over the network. Any encryption standard or authentication method as may be understood by those having ordinary skill in the art may be used at any point in the system of the present invention. For example, encryption may be accomplished by encrypting an output file by using a Secure Socket Layer (SSL) with dual key encryption. Additionally, the system may limit data manipulation, or information access. Access or use restrictions may be implemented for users at any level. Such restrictions may include, for example, the assignment of user names and passwords that allow the use of the present invention, or the selection of one or more data types that the subservient user is allowed to view or manipulate.

In certain embodiments the network provides for telemetric data transfer from the sensor control unit to the external processing unit, and vice versa. For example, data transfer can be made via any wireless communication and may include any wireless based technology, including, but not limited to radio signals, near field communication systems, hypersonic signal, infrared systems, cellular signals, GSM, and the like. In some embodiments, data transfer is conducted without the use of a specific network. Rather, in certain embodiments, data is directly transferred to and from the sensor control unit and external processing unit via systems described above.

The software may include a software framework or architecture that optimizes ease of use of at least one existing software platform, and that may also extend the capabilities of at least one existing software platform. The software provides applications accessible to one or more users (e.g. patient, clinician, etc.) to perform one or more functions. Such applications may be available at the same location as the user, or at a location remote from the user. Each application may provide a graphical user interface (GUI) for ease of interaction by the user with information resident in the system. Exemplary GUIs of the invention may include the ability for a user to control the function or mode of the sensors, as well as the ability to display individual intrinsic cardiac neuron activity, pooled data of neuronal activity, or of general cardiac function as would be understood by those skilled in the art. Such data may include indices of network function including, but not limited to, temporal relationships of neural activity to one another, temporal relationships to cardiac electrical or mechanical events, temporal relationships to controlled events including pacing, mechanical, or chemical stressors. A GUI may be specific to a user, set of users, or type of user, or may be the same for all users or a selected subset of users. The system software may also provide a master GUI set that allows a user to select or interact with GUIs of one or more other applications, or that allows a user to simultaneously access a variety of information otherwise available through any portion of the system. Presentation of data through the software may be in any sort and number of selectable formats. For example, a multi-layer format may be used, wherein additional information is available by viewing successively lower layers of presented information. Such layers may be made available by the use of drop down menus, tabbed folder files, or other layering techniques understood by those skilled in the art.

The software may also include standard reporting mechanisms, such as generating a printable results report, or an electronic results report that can be transmitted to any communicatively connected computing device, such as a generated email message, text or file attachment. Likewise, particular results of the aforementioned system can trigger an alert signal, such as the generation of an alert email, text or phone call, to alert a patient, doctor, nurse, emergency medical technicians, or other health care provider of the particular results.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Vagal Stimulation Targets Select Populations of Intrinsic Cardiac Neurons to Control Neutrally Induced Atrial Fibrillation The model of atrial fibrillation used in the present experiments is intermittent focal mediastinal nerve stimulation (MNS) (Armour J A et al., 2005, Auton Neurosci, 118:68-78). MNS elicits intrinsic cardiac nervous system (ICNS) network hyperexcitability (Gibbons D D et al., 2012, Am J Physiol Regul Integr Comp Physiol, 302:R357-R364) that in turn deranges efferent neuronal outflows to atrial tissues, thereby causing heterogeneities in atrial electrical indexes (Armour J A et al., 2005, Auton Neurosci, 118:68-78; Richer L P et al., 2008, Am J Physiol Regul Integr Comp Physiol, 295:R1175-R1180). Such heterogeneities in the atrial electrical substrate rapidly degenerate into self-limiting episodes of AF (Armour J A et al., 2005, Auton Neurosci, 118:68-78; Richer L P et al., 2008, Am J Physiol Regul Integr Comp Physiol, 295:R1175-R1180). The MNS-induced AF episodes occur with a latency of ~1 second from stimulation onset, have a duration of ~30 seconds, and are reproducible over hours of experimentation (Armour J A et al., 2005, Auton Neurosci, 118:68-78; Gibbons D D et al., 2012, Am J Physiol Regul Integr Comp Physiol, 302:R357-R364; Richer L P et al., 2008, Am J Physiol Regul Integr Comp Physiol, 295:R1175-R1180). This model provides a reproducible experimental platform whereby anti-arrhythmic therapies can be evaluated and optimized (Armour J A et al., 2005, Auton Neurosci, 118:68-78; Gibbons D D et al., 2012, Am J Physiol Regul Integr Comp Physiol, 302:R357-R364; Leiria T L et al., 2011, Auton Neurosci, 161:68-74; Richer L P et al., 2008, Am J Physiol Regul Integr Comp Physiol, 295:R1175-R1180). Previous work has demonstrated that MNS-induced AF can be eliminated by atropine (Armour J A et al., 2005, Auton Neurosci, 118:68-78), modified by timolol (Armour J A et al., 2005, Auton Neurosci, 118:68-78), and blunted by α-adrenoceptor blockade (Richer L P et al., 2008, Am J Physiol Regul Integr Comp Physiol, 295: R1175-R1180). Hexamethonium likewise reduces the number of AF responses to MNS stimulation from 90% baseline to 10% posttreatment (Richer L P et al., 2008, Am J Physiol Regul Integr Comp Physiol, 295:R1175-R1180). These data substantiate fundamental aspects of ICNS neural activity in relationship to regulation of the AF potential. However, the role of local circuit neurons (LCNs) in mediating AF remain unclear, and whether LCNs may be a preferential target for bioelectric therapies remains unknown.

Vagus nerve stimulation modulates cardiac electrical indexes (Levy M N et al., 1979, Neural control of the heart. In: Handbook of Physiology. The Cardiovascular System. The Heart. Bethesda, Md.: Am Physiol Soc, 1(2), 581-620; Yamakawa K et al., 2014, Am J Physiol Heart Circ Physiol, 307:H722-H731) and, as such, has the potential to either increase or decrease the propensity to arrhythmias (Chen P S et al., 2014, Circ Res, 114:1500-1515). Higher-intensity stimulations tend to increase atrial fibrillation inducibility (Zhang Y et al., 2009, Heart Rhythm, 6:244-250; Zhang Y et al., 2009, J Intery Card Electrophysiol, 24:5-10); lower-intensity vagal stimulation can stabilize atrial electrical function (Chen M et al., 2015, Int J Cardiol, 199:437-438; Stavrakis S et al., 2015, J Am Coll Cardiol, 65:867-875). To understand the efficacy of VNS therapy with respect to atrial arrhythmia suppression, the response characteristics of functionally delineated subpopulations of intrinsic cardiac (IC) neurons to MNS-evoked AF were first defined, and then the capacity of cervical VNS (right vs. left) to modify neural network and cardiac electrical responses to such destabilizing inputs was determined. To this purpose, the activity of multiple neurons in the canine right atrial ganglionated plexuses (RAGP), an aggregate of IC neurons directly involved in control of chronotropic function (Ardell J L et al., 1986, Am J Physiol Heart Circ Physiol, 251:H764-H773; McGuirt A S et al., 1997, Am J Physiol Heart Circ Physiol, 272:H2525-H2533; Randall D C et al., 2003, Am J Physiol Regul Integr Comp Physiol, 285:R1066-R1075), was recorded. Data presented herein demonstrate mechanistically the pivotal role of LCNs in mediating AF secondary to neural imbalances and that these same neurons are the preferential target for bioelectric therapies to reduce the arrhythmogenic potential. It is further demonstrated herein that these bioelectric interventions exhibit memory to extend the atrial antiarrhythmic effects well beyond the primary activity phase of VNS therapy.

It is demonstrated herein that MNS reproducibly evokes AF by excessive and heterogeneous activation of IC neurons. The experiments presented herein evaluated whether preemptive VNS impacts MNS-induced evoked changes in IC neural network activity to thereby alter susceptibility to AF. IC neuronal activity in the right atrial ganglionated plexus was directly recorded in anesthetized canines (n=8) using a linear microelectrode array concomitant with right atrial electrical activity in response to: 1) epicardial touch or great vessel occlusion vs. 2) stellate or vagal stimulation. From these stressors, post hoc analysis (based on the Skellam distribution) defined IC neurons so recorded as afferent, efferent, or convergent (afferent and efferent inputs) local circuit neurons (LCN). The capacity of right-sided MNS to modify IC activity in the induction of AF was determined before and after preemptive right (RCV)-vs. left (LCV)-sided VNS (15 Hz, 500 fs; 1.2× bradycardia threshold). Neuronal (n=89) activity at baseline (0.11±0.29 Hz) increased during MNS-induced AF (0.51±1.30 Hz; P<0.001). Convergent LCNs were preferentially activated by MNS. Preemptive RCV reduced MNS-induced changes in LCN activity (by 70%) while mitigating MNS-induced AF (by 75%). Preemptive LCV reduced LCN activity by 60% while mitigating AF potential by 40%. IC neuronal synchrony increased during neurally induced AF, a local neural network response mitigated by preemptive VNS. These antiarrhythmic effects persisted post-VNS for, on average, 26 min.

In summary, VNS preferentially targets convergent LCNs and their interactive coherence to mitigate the potential for neurally induced AF. The antiarrhythmic properties imposed by VNS exhibit memory.

The materials and methods employed in these experiments are now described.

Animal Preparation

Eleven mongrel dogs of either sex, weighing 18.6-26.9 kg, entered this study. Animals were sedated with propofol (3-8 mg/kg iv), followed by endotracheal intubation and mechanical ventilation. General anesthesia was maintained with isoflurane (1-2%, inhalation). Following completion of surgery, anesthesia was changed to α-chloralose (50 mg/kg iv bolus), with continuous infusion (8-12 mg·kg$^{-1}$·h$^{-1}$ iv) adjusted to effect throughout the duration of each study. The depth of anesthesia was assessed throughout the experiments by monitoring corneal reflexes, jaw tone, and hemodynamic indexes. Body temperature was maintained via a circulating water heating pad (Gaymar T/Pump; Gaymar Industries, Orchard Park, N.Y.). At the completion of the experiments, animals were humanely killed under deep anesthesia and by inducing ventricular fibrillation via application of direct current stimulation and removing the heart.

Hemodynamic Recording

The left femoral artery was catheterized to record arterial blood pressure (Ao BP). The left femoral vein was catheterized to allow for fluid replacement, as well as anesthetic and pharmacological agent delivery. The right femoral artery was catheterized to monitor left ventricular chamber pressure (LVP) via placement in the left ventricular (LV) chamber of a Mikro-Tip Pressure Transducer Catheter (Millar Instruments, Houston, Tex.). Heart rate was monitored via a Lead II electrocardiogram (ECG). Pressures (Ao BP, LVP) and ECG were input to a Cambridge Electronics Design (model 1401) data acquisition system for continuous monitoring of hemodynamic status.

Vagal Stimulation (VNS)

Following a midline incision in the ventral neck, the right and left cervical vagi were exposed, and bipolar stimulation electrodes (PerrenialFlex, model 304, Cyberonics) were placed around each nerve. Cervical vagosympathetic trunks remained intact throughout each aspect of the protocol. Each lead was connected individually to a Grass S88 stimulator via separate PSIU6 constant current isolation units. Bradycardia thresholds for each nerve stimulated were identified using 20 Hz, 500-µs pulse width stimuli, as determined by progressive increases in current intensity until 10% bradycardia was evoked. With respect to right-sided VNS, this current was found to be, on average, 1.75 mA; for left-sided VNS it was 2.25 mA. VNS was applied to each vagus for 3-min periods (15 Hz; 500-µs pulse width) at a current intensity that was 1.2× bradycardia threshold.

Mediastinal Nerve Stimulation

Following thoracotomy, an incision was made in the pericardial sac, and a pericardial cradle was formed. A bipolar electrode was affixed to the right atrium 1 cm dorsal to the sinoatrial node to record an atrial electrogram. Right-sided mediastinal nerves were identified visually coursing over the ventral and ventrolateral surface of the intrapericardial aspects of the superior vena cava. These mediastinal nerves represent aggregates of sympathetic and parasympathetic efferent axons, as well as interganglionic projections arising from local circuit neurons contained within the ICNS (Armour J A et al., 2005, Auton Neurosci, 118:68-78; Gibbons D D et al., 2012, Am J Physiol Regul Integr Comp Physiol, 302:R357-R364; Gray A L et al., 2004, J Appl Physiol, 96:2273-2278; Waldmann M et al., 2006, J Appl Physiol, 101:413-419).

Each nerve was stimulated individually using detailed published techniques (Armour J A et al., 2005, Auton Neurosci, 118:68-78; Gibbons D D et al., 2012, Am J Physiol Regul Integr Comp Physiol, 302:R357-R364). Briefly, trains of five electrical stimuli (0.3-1.2 mA, 1 ms duration, 5 ms pulse interval) were delivered during individual atrial refractory periods to identified mediastinal sites for up to 20 seconds. Electrical stimuli were delivered to a mediastinal nerve via a roving bipolar probe electrode. Active nerve sites were identified by the immediate induction of atrial tachyarrhythmias (including atrial fibrillation) when first exposed to focal electrical stimuli. Each active mediastinal nerve site so identified was marked with India ink for repeated stimulation. By these means, two to four active nerve sites were identified in each animal. Contact between the bipolar electrodes and tissue was discontinued immediately after the onset of the atrial tachyarrhythmia to limit their durations (Armour J A et al., 2005, Auton Neurosci, 118:68-78; Richer L P et al., 2008, Am J Physiol Regul Integr Comp Physiol, 295:R1175-R1180).

Neuronal Recording

Extracellular activity generated by intrinsic cardiac neurons in situ was recorded using a multichannel linear microelectrode array (MicroProbes, Gaithersburg, Md.) that consisted of 16 platinum/iridium electrodes (25 µm-diameter electrode with an exposed tip of 2 mm; impedance 0.3-0.5 MΩ at 1 kHz). The linear microelectrode array was embedded in the right atrial fat that contained the right atrial ganglionated plexus (RAGP), as described previously (Beaumont E et al., 2013, J Physiol, 591:4515-4533). The connecting wires of the multichannel electrode, along with ground and reference wires, were attached to a 16-channel microelectrode amplifier with a headstage preamplifier (model 3600; A-M Systems, Carlsborg, Wash.). For each channel, filters were set to 300 Hz to 3 KHz and gain to 5 K. Another electrode was sewn to the atrial myocardium close to the RAGP to provide a reference right atrial electrogram that was used to determine atrial rate, duration and characterization of atrial arrhythmias, along with a timing index for subsequent identification of atrial electrical artifacts in IC neural recording data. The 16 microelectrode array signals, along with recorded cardiovascular indexes (ECG, right atrium electrogram, and hemodynamic data), were digitized via a Cambridge Electronics Design (model 1401) data acquisition system for off-line analysis. The sampling frequency for neuronal data was 5.26 kHz; it was six times lower (0.877 kHz) for all other recorded signals.

Identification of Neuronal Activity

The extracellular activity generated by individual neuronal somata located within the RAGP was recorded. Identification of the activity generated by individual neurons via the 16-channel electrodes was performed off line using the Spike2 software program (Cambridge Electronic Design) in two steps: 1) artifact identification and blanking and 2) spike detection, waveform classification, and validation with principal component analysis as defined previously (Beaumont E et al., 2013, J Physiol, 591:4515-4533). With the use of these procedures, consistent waveforms derived from individual somata (not axons of passage) can be identified in situ for up to 8- to 10-hour periods (Beaumont E et al., 2013, J Physiol, 591:4515-4533; Rajendran P S et al., 2016, J Physiol, 594:321-341; Thompson G W et al., 2000, J Physiol, 528:561-571). Of the 11 animals, recordings with sufficient signal to noise were obtained in eight animals. As such, the remaining three were excluded from all subsequent analysis.

Statistical Analysis of Evoked Changes in IC Neuronal Activity

Using statistical approaches based on a Skellam distribution (Shin H C et al., 2010, IEEE Trans Biomed Eng, 57:754-760), the significance of changes in firing rates recorded before and during each intervention was computed post hoc for all identified IC neurons. The behavior of identified neurons was classified according to their activity characteristics in response to the following interventions: 1) touching the ventral LV and then right ventricle (conus vs. sinus); 2) 20 second descending aorta occlusion; 3) 20 second inferior vena cava occlusion; 4) stimulation (1 Hz for 1 min) of right vs. left cervical vagosympathetic trunk (RCV; LCV); and 5) stimulation (1 Hz for 1 min) of right vs. left stellate ganglia. By these means, each neuron was classified according to how it responded to each of those interventions by its change in firing rate, each serving as its own control. When a neuron responded solely to one or more of the afferent stressors (interventions 1-3 above), it was classified as an afferent LCN. Efferent LCNs were identified as those responding indirectly (variable latency) to one or more of the efferent (vagal vs. sympathetic; interventions 4 and 5 above) inputs. IC neurons that respond with a fixed latency to efferent inputs were classified at efferent IC neurons (Armour J A., 2008, Exp Physiol, 93:165-176). IC neurons that responded indirectly to both afferent and efferent stressor were classified as convergent LCN (Beaumont E et al., 2013, J Physiol, 591:4515-4533). Identified neurons that did not respond to any of these stressors were classified as exhibiting unknown function.

One objective of this study was to assess the efficacy of preemptive VNS to alter the IC neural network response to MNS and thereby impact the atrial arrhythmogenic potential. Repeated-measure ANOVA was used to assess the effect of different factors on neuronal activity. The three-way ANOVA test was performed on RCV and LCV separately. It involved two within-subject factors (effect of MNS vs. baseline, and pre- vs. post-VNS response) and one between-subjects factor (neuron type). Huynd-Fedlt correction was applied to correct the violation of sphericity assumption. When significance was achieved overall for ANOVA (P<0.05), post hoc test and all other paired-sample comparisons were done by paired t-test.

In each animal, a synchrony index (SI) was also calculated (Longpre J P et al., 2014, Physiol Meas, 35:549-566) to evaluate synchrony of activity generated among different populations of IC neurons. This index was estimated during: 1) baseline states compared with 2) during episodes of neurally induced atrial arrhythmias. The potential of VNS to alter IC synchrony was likewise assessed. There was a limitation of analysis imposed by the limited number of action potentials generated per neuron, especially when suppressed during VNS therapy; as such, synchrony analysis was not performed in those instances. The synchrony of activities displayed by different populations of identified neurons, as defined by Agmon (Agmon A., 2012, Neural Syst Circuits, 2:5), was performed by assessing the activity generated by pairs of identified neurons in each animal. To calculate such a SI, one neuron was defined as the reference and the other as the target neuron.

Different SI values were obtained that depended on which neuron was considered reference, thus making the SI a nonsymmetric measure. As such, calculation of this SI required the identification of coincidences of activities among differing neurons when reference and target neurons both generate activity within a time window of selected duration T. The optimal value for T with respect to intrinsic cardiac neuronal activities was previously defined to be 40 ms (Longpre J P et al., 2014, Physiol Meas, 35:549-566). Given that some coincidences may be random in nature, the coincidence count was also estimated in surrogate data obtained by applying a random jitter to the reference spikes in each time window of duration 4T (Agmon A., 2012, Neural Syst Circuits, 2:5). To obtain normalized SI values, the mean coincidence count in surrogate data was subtracted from the actual coincidence count identified. Thereafter, the resultant was divided by the number of reference spikes. Surrogate data also served to calculate a P value so that we could assess statistical significance of these data. When the number of neuron pairs demonstrating significant synchrony was so identified (P<0.01 and SI >0.01), a Chi square test was performed to assign statistical significance to changes occurring in the number of synchronized pairs for each neuronal subtype combination studied (Snedocor G, et al., 1980, Statistical Methods, Ames, Iowa: Iowa State Univ Press).

AF Characteristics

Atrial electrograms were recorded from the ventral right atrial free wall and referenced to a Wilson Central terminal. From these atrial electrograms, the following response characteristics were determined during the atrial tachyarrhythmia: 1) latency (defined as the interval from the first applied stimulus to tachyarrhythmia initiation); 2) duration of the AF (defined as time from onset to self-termination of AF); and 3) dominant frequency of atrial activity during induced AF episode. When AF was not initiated by MNS, AF duration was by definition set to zero. The duration of AF episodes recorded before and after VNS were compared by reference to the duration of each, as obtained from one or more AF episodes induced before and after full recovery from the VNS protocols. The effects of VNS therapy were separated into four categories, using MNS as the constant defined stressor: 1) AF prevention (AF initiation failed); 2) AF mitigation (AF duration reduced by 20% or more); 3) AF prolongation (AF duration increased by at least 20%); and 4) having no effect. Results were considered to be not significant (no effect) when occurring within the 20% range.

Time Dependence of VNS Effect

Kaplan-Meier survival analysis was performed to estimate how long the effect of VNS lasted as represented by the varied number (up to 7) of successive AF initiation attempts (at 5- or 10-min intervals after the first, if needed). When a mediastinal nerve stimulus evoked an AF episode as long as the reference (control state) episode, sequential MNS trials were terminated. Accordingly, VNS efficacy at time t was defined as the percentage of experiments for which the latest unsuccessful AF attempt (if any) occurred after time t. A second survival curve was also created based on the percentage of experiments in which the latest mitigated AF episode (if any) occurred after time t to determine how long VNS effectiveness lasted.

The results of the experiments are now described.

Functional Response Characteristics of Identified Right Atrial Neurons

A total of 89 neurons were identified in the 8 animals studied (11.1±3.5 neurons/dog). The response characteristics of individual neurons differed with respect to the stressor tested, which could be reflected as either an increase or decrease in activity (FIG. 1). Of the 89 identified right atrial neurons (those that generated spontaneous activity), 65 neurons were functionally classified as being 1) afferent (n=15; 17%), 2) efferent (n=20; 22%), or 3) convergent local circuit neurons (n=30; 34%). The rest (n=24; 27%) did not respond to any of these imposed stressors; as such, their function was labeled as being unknown.

Effects of Right-Sided Mediastinal Nerve Stimulation on Cardioneural Activity

Figure 2:
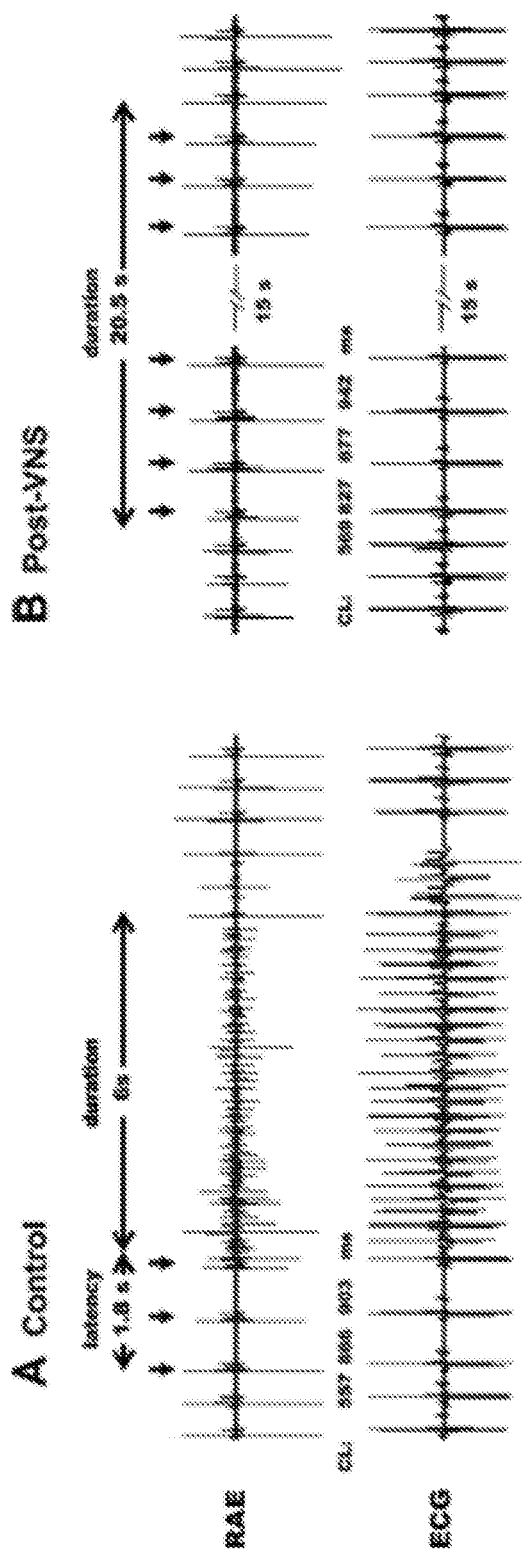
FIG. 2 depicts results from example experiments, showing vagus nerve stimulation (VNS) effects on MNS-induced atrial fibrillation (AF). Atrial electrical activity recorded from a unipolar electrode on the ventral right atrial free wall along with lead II ECG. Bursts of electrical stimuli applied to a caudal right-sided mediastinal nerve during the atrial refractory period (downward arrows) elicited arrhythmias before (FIG. 2A) but not after (FIG. 2B) preemptive right-sided VNS.

FIG. 2 illustrates a representative atrial arrhythmic response elicited by brief periods of MNS stimulation before (control; FIG. 2A) and following (post-VNS; FIG. 2B) preemptive VNS. In the control state, MNS on average induced transient periods of AF with a latency to onset of 2.68±2.32 s, a duration of 11.1±1.2 s, and a dominant frequency of 7.1±0.1 Hz during AF. Note that bradycardia usually preceded the onset of atrial tachycardia/AF (FIG. 2A) and that this onset transient bradycardia was maintained following VNS (FIG. 2B). In this same animal, VNS pretreatment prevented the tachyarrhythmias induced by MNS (FIG. 2B), even when applied for up to 20 s. The hemodynamic response to VNS is summarized in FIG. 3. The evoked changes in chronotropic and left ventricular inotropic function, with suppression during the active VNS phase followed by a rebound phase (1 min duration) following stimulation, are consistent with the 1.2× threshold intensity used herein. By onset of MNS stressors post-VNS, hemodynamics had returned to baseline values.

Figure 4:
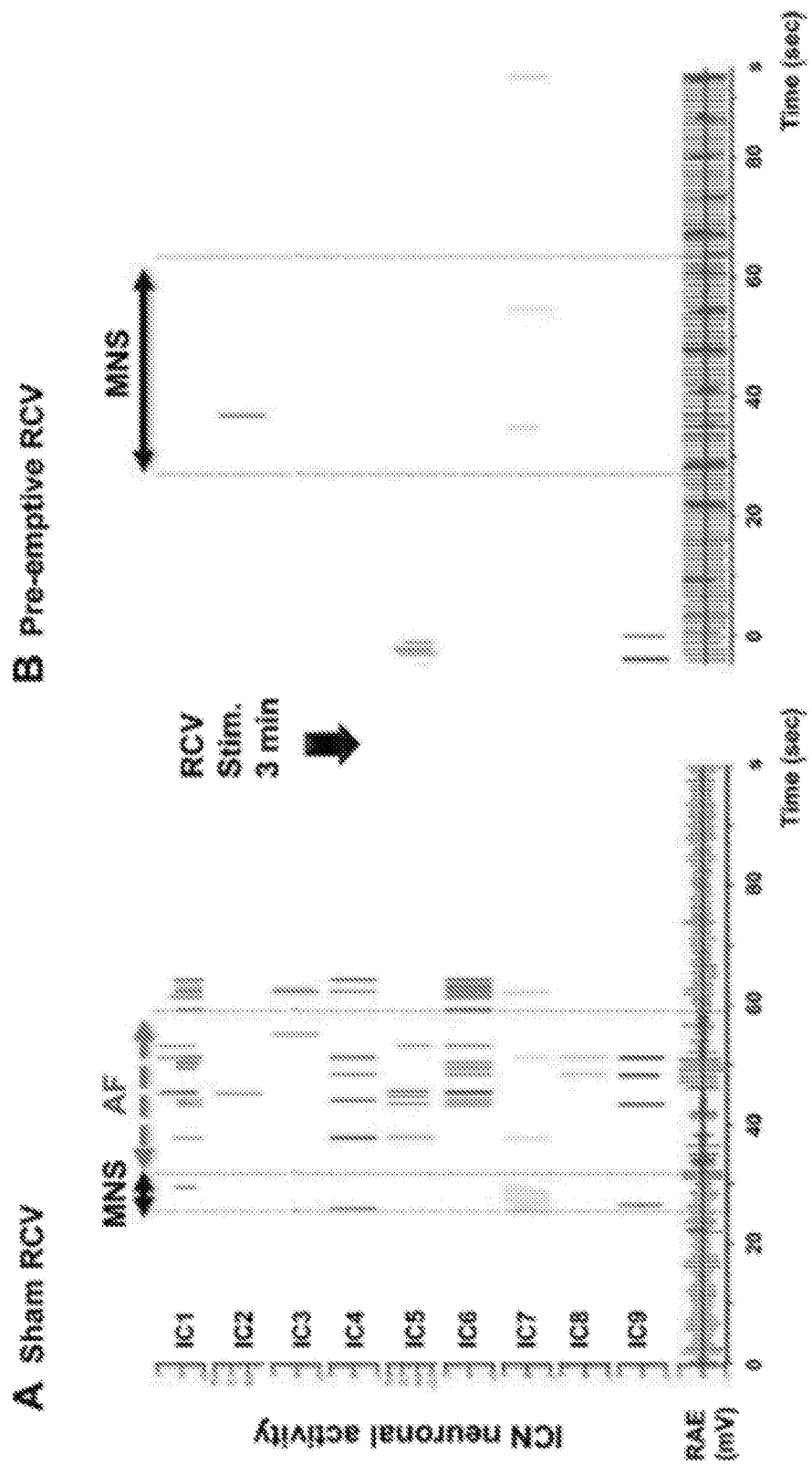
FIG. 4 depicts results from example experiments, showing representative responses to MNS before (FIG. 4A) and after (FIG. 4B) RCV VNS. A right atrial electrogram (RAE, bottom) is displayed with concomitant activities generated by 9 identified IC neurons.

MNS stimulation triggered changes in IC activity leading to atrial arrhythmias, with residual effects continuing even post-conversion to sinus rhythm. In the representative animal depicted in FIG. 4, in the control state bursting of activity was elicited among nine identified right atrial neurons by MNS (FIG. 4A, MNS: sham RCV). Neural activity enhancement occurred immediately before the induction of the transient atrial arrhythmia (cf., AF). Activity persisted in five of these nine neurons for a brief period of time even after spontaneous conversion to sinus rhythm. Average neuronal activity recorded among all classified IC neurons across all animals was $0.11±0.29$ Hz in control states, increasing to $0.51±1.30$ Hz ($P<0.001$) during the MNS-induced atrial tachyarrhythmia. From subset analysis, IC activity increased preferentially among convergent LCNs ($0.13±0.3$ to $0.88±1.73$ Hz, $P<0.001$) in response to MNS, with afferent LCNs responding to a lesser degree ($0.07±0.3$ to $0.14±0.43$ Hz, $P<0.032$). No changes were identified in identified efferent LCN populations ($0.11±0.3$ to $0.21±0.74$ Hz, $P=0.24$).

Figure 5:
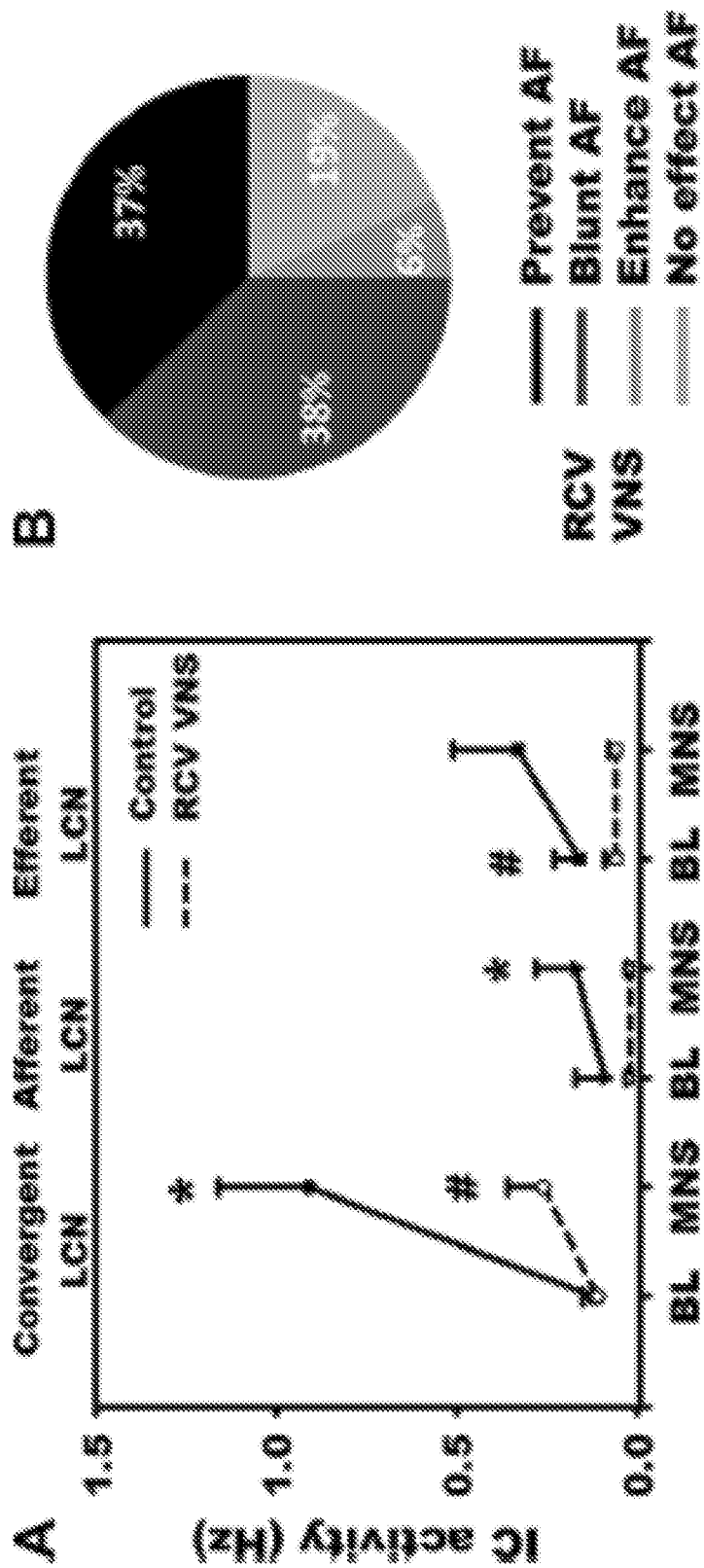
FIG. 5 depicts results from example experiments, showing (FIG. 5A) response of IC neurons to MNS before (solid line) vs. following (broken line: RCV VNS) preemptive right-sided (ipsilateral) bioelectric therapy. IC neurons were subclassified as convergent, afferent, or efferent LCNs (compare with FIG. 1). Convergent LCNs were the predominant population of neurons activated by MNS and the primary target for preemptive RCV neuromodulation therapy.

Effects of Ipsilateral Vagus Nerve Stimulation on Right-Sided Atrial Neuronal Activity and the Potential for Neurally Induced Atrial Arrhythmias Preemptive right-sided VNS mitigated IC neural responses to MNS (FIG. 4B and FIG. 5A). It blunted or prevented the potential for neurally induced AF by 75% (FIG. 5B), with no significant changes in onset latency or dominant frequency in residual arrhythmias. Before VNS, MNS increased the activity among both afferent and convergent LCN subpopulations (FIG. 5A). Following preemptive right-sided VNS, basal activity was differentially decreased among efferent LCNs ($0.16±0.4$ vs. $0.06±0.19$ Hz, $P<0.01$). Post-VNS, MNS-induced excitation of convergent LCNs was blunted ($0.91±1.73$ vs. $0.26±0.73$ Hz; $P<0.002$), being totally eliminated among afferent LCN populations (FIG. 5A).

Figure 6:
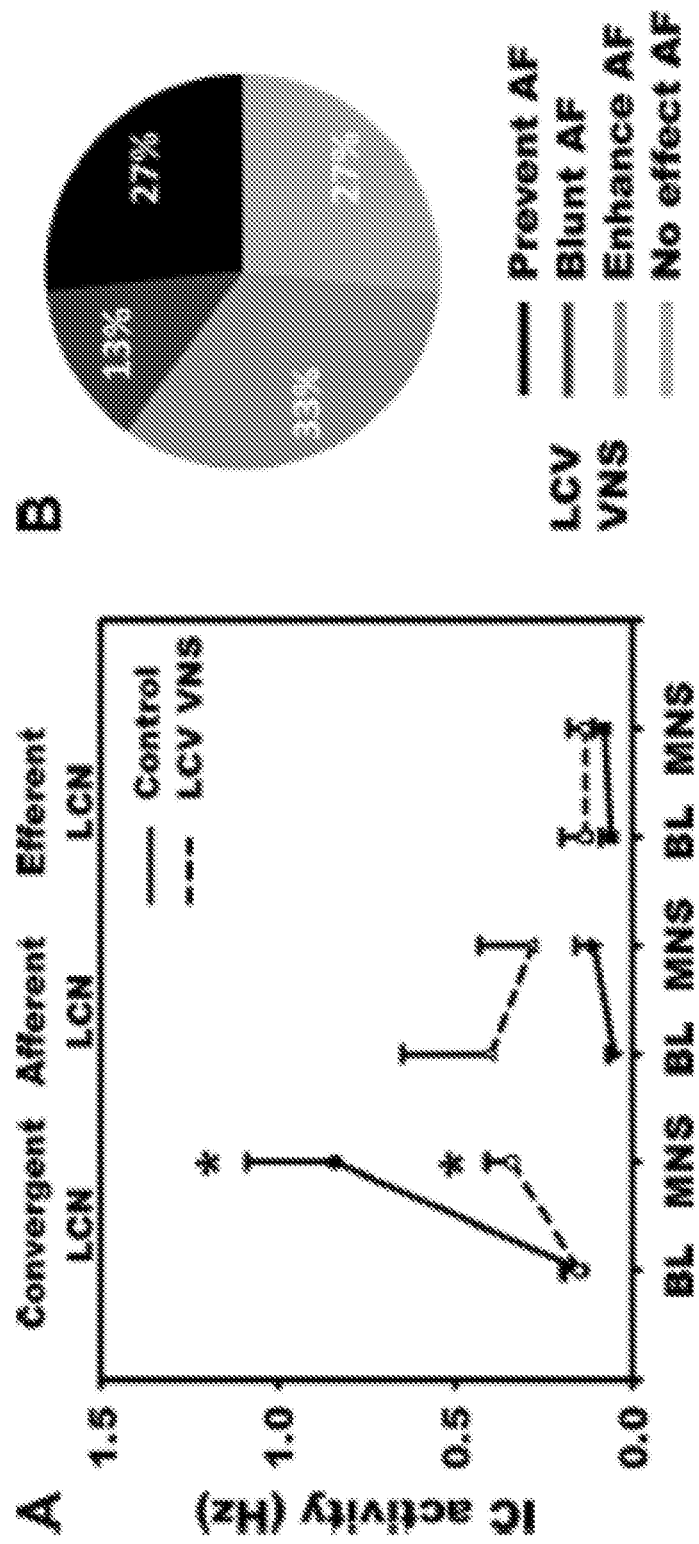
FIG. 6 depicts results from example experiments, showing (FIG. 6A) response of IC neurons to MNS before (solid line) vs. after (broken line: LCV VNS) preemptive left-sided (contralateral) bioelectric therapy. IC neurons were subclassified as convergent, afferent, or efferent LCNs, as defined in FIG. 1. Convergent LCNs were the predominant population activated by MNS and the primary target for preemptive LCV therapy.

Effects of Contralateral Vagus Nerve Stimulation on Right-Sided Atrial Neuronal Activity and the Potential for Neutrally Induced Atrial Arrhythmias In contrast to ipsilateral VNS, left-sided vagus stimulation exerted no significant change in basal IC neuronal activity (FIG. 6A). However, as with right-sided VNS, LCV differentially mitigated the MNS-induced increase in convergent LCN activity ($0.84±1.74$ vs. $0.34±0.49$ Hz, $P=0.057$). In contradistinction to ipsilateral-mediated effects, though blunted, the neural activity in convergent neurons still increased significantly above baseline during MNS following the LCV VNS. The potential for MNS-induced AF was prevented or blunted 40% by LCV VNS and without effect in 27% of cases. Preemptive left-sided VNS enhanced AF induced from 33% of right-sided MNS sites evaluated (FIG. 6B).

IC Network Characteristics: Neuronal Synchrony

Figure 7:
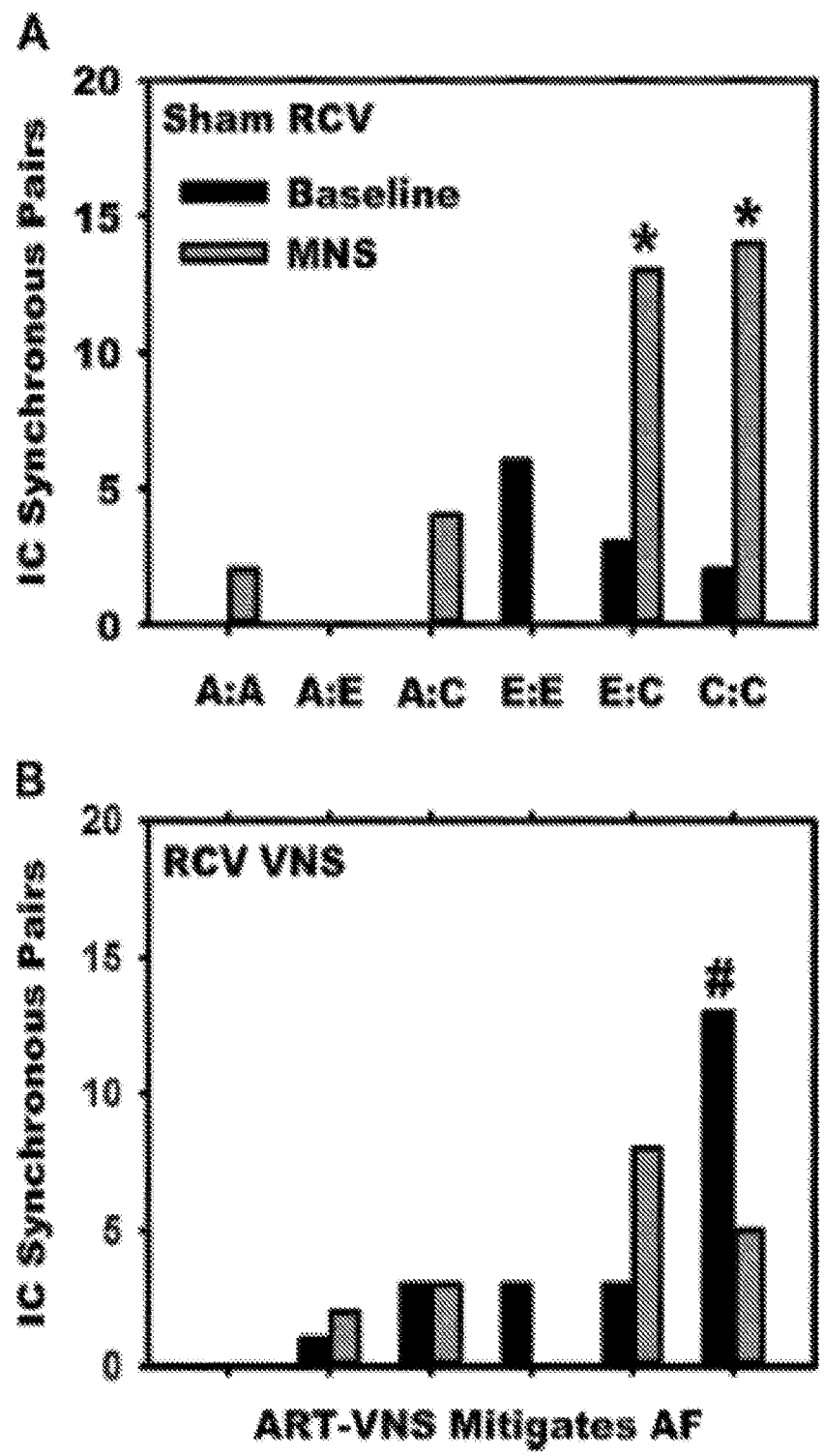
FIG. 7 depicts results from example experiments, showing MNS-induced changes in IC network synchrony. The synchronized activities generated by identified pairs of IC neurons (synchrony index (SI) >0.01 and $P<0.01$) were determined and classified post hoc, according to comparing concomitant activities generated by: afferent LCNs (A); efferent LCNs (E); and convergent LCNs (C). Vertical columns represent the degree of synchrony (number of synchronous pairs) between the 6 combinations of neuron pairings elicited during: 1) baseline (black bars) vs. 2) MNS-induced (gray bars) arrhythmias. These relationships are depicted in untreated (sham VNS, FIG. 7A) states and following preemptive bioelectric therapy (RCV VNS, FIG. 7B). Note that MNS induced differential increases in synchrony between efferent-to-convergent IC pairs (E:C), as well as convergent-to-convergent neuronal pairings (C:C) (top). Whereas at baseline preemptive RCV differentially increased synchrony between convergent LCNs, it eliminated the increase in synchrony across all other neuronal subclass pairings during MNS (bottom). *$P<0.02$ from baseline and #$P<0.01$ sham to RCV VNS state.

The MNS-induced increases in IC activity are reflective of common shared inputs and/or IC network interconnections mediated by LCNs (Armour J A., 2008, Exp Physiol, 93:165-176). FIG. 7 evaluates this short-term interactive potential by determining synchrony among the specific pairs of IC neurons identified within the RAGP during baseline conditions, as well as during MNS-induced changes 1) before (top) and following (bottom) preemptive right-sided VNS. In the sham (unstimulated) treatment state, note that, while there was minimal coherence of activity among the various subpopulations of IC neurons identified, in response to MNS there was a preferential increase in IC synchrony among convergent LCNs, as well as between convergent and efferent LCN subpopulations. Following right-sided VNS, while there was a differential increase in synchrony during baseline states among convergent LCNs (FIG. 7, bottom), any MNS-induced change in IC synchrony was extinguished.

IC Network Characteristics: Memory

Figure 8:
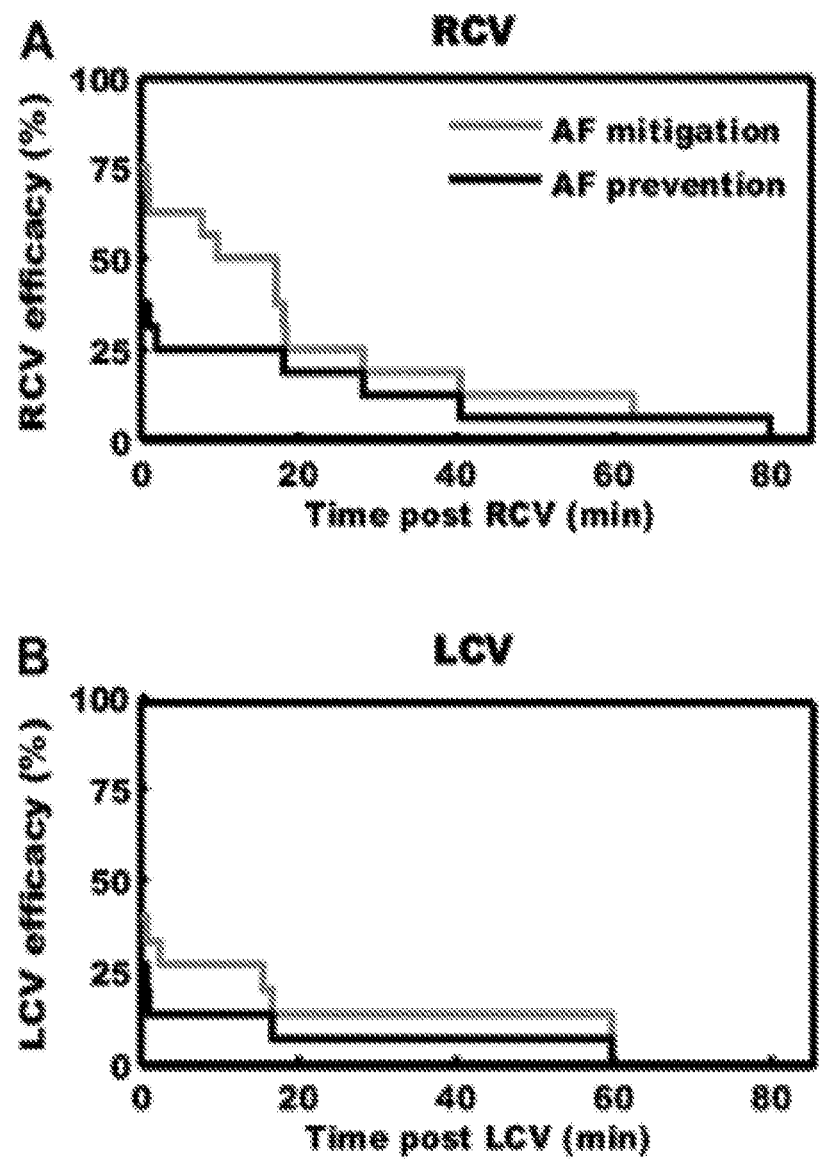
FIG. 8 depicts results from example experiments, showing that VNS-induced antiarrhythmic effects exhibit memory.

The efficacy of VNS therapy in terms of shortening/preventing MNS-induced arrhythmias (post-VNS) was assessed via Kaplan-Meier survival analysis (FIG. 8). Following right-sided VNS, antiarrhythmic effects against repeated MNS-induced arrhythmias were attenuated for 20 min after VNS therapy (top) and extinguished by ~40 min post-VNS (fitting exponential function resulted in a time constant of $26±2$ min (95% confidence interval); FIG. 8A). While the overall antiarrhythmic efficacy of contralateral VNS was reduced (FIG. 8, bottom), the time constants derived from RCV vs. LCV responses were not significantly different (log-rank test). For corresponding MNS-induced changes in IC activity, the pre-VNS-induced change in convergent activity (0.11 to 1.57 Hz, $P=0.023$) was suppressed immediately after VNS (0.04 to 0.38 Hz, $P=0.17$) and recovered ~30 min post-VNS (0.07 to 1.28 Hz, $P=0.016$). Following recovery, characteristics of MNS-induced AF (latency, duration, and dominant frequency) were similar to sham VNS control.

VNS Therapy Attenuates AF Via Convergent LCNs

The major findings of the experiments described herein are: 1) enhanced activity on convergent LCNs underlies neurally induced AF; 2) VNS therapy attenuates AF via its effects on select intrinsic cardiac neuronal populations, namely convergent LCNs; 3) disruptive neural inputs to the ICNS increase coherence of activity among IC neurons, and preemptive VNS prevents such effects; 4) ipsilateral VNS imparts a greater impact on IC neural function and the ability to stabilize the ICNS against neural imbalance; and 5) the antiarrhythmic effects imparted by VNS have memory.

ICN Modulation of Cardiac Function

The ICNS is composed of heterogeneous populations of neurons loosely organized in multiple ganglionated plexi located within atrial and ventricular tissues (Armour J A., 2008, Exp Physiol, 93:165-176; Beaumont E et al., 2013, J Physiol, 591:4515-4533; Yuan B X et al., 1994, Anat Rec, 239:75-87). These IC neurons can be functionally stratified by their in situ behavior based on their responses to different stressors according to whether they belong to either afferent, efferent, or convergent LCN subtypes (Armour J A., 2008, Exp Physiol, 93:165-176; Beaumont E et al., 2013, J Physiol, 591:4515-4533). Structure is intricately intertwined to function (Beaumont E et al., 2013, J Physiol, 591:4515-4533; Cardinal R et al., 2009, Auton Neurosci, 145:55-62; Rajendran P S et al., 2016, J Physiol, 594:321-341). The convergent LCNs are responsible for primary reflex integration within the ICNS (Armour J A., 2008, Exp Physiol, 93:165-176), coordinating atrial and ventricular tissues via its efferent outputs. With respect to central autonomic efferent preganglionic axons, they project directly on intrinsic cardiac efferent postganglionic (intrinsic cardiac parasympathetic and sympathetic) neurons and convergent LCNs (Beaumont E et al., 2013, J Physiol, 591:4515-4533; McGuirt A S et al., 1997, Am J Physiol Heart Circ Physiol, 272:H2525-H2533; Randall D C et al., 2003, Am J Physiol Regul Integr Comp Physiol, 285:R1066-R1075). These IC network interactions are critical to mediating sympathetic/parasympathetic cardiomotor outflow to control regional cardiac function (McGuirt A S et al., 1997, Am J Physiol Heart Circ Physiol, 272:H2525-H2533; Randall D C et al., 1998, Am J Physiol Regul Integr Comp Physiol, 275:R779-R787).

ICN Processing and Atrial Arrhythmias

Asymmetric neural inputs to the IC network increase the potential for atrial tachycardia/AF (Armour J A et al., 2005, Auton Neurosci, 118:68-78; Chen P S et al., 2014, Circ Res, 114:1500-1515). Stochastic processing within that network underlies the instability that can occur within the ICNS to initiate arrhythmias (Kember G et al., 2013, J Theor Biol, 317:39-46; Kember G et al., 2013, Physiol Genomics, 45:638-644). The resultant "hyperstochasticity" displayed among its convergent LCNs in response to MNS appears to be fundamental to any enhancement of an arrhythmia potential (Gibbons D D et al., 2012, Am J Physiol Regul Integr Comp Physiol, 302:R357-R364). The present invention shows that any such enhancement of activity among IC LCNs is associated with increases in their coherence to effect local efferent neuronal outflows (Gray A L et al., 2004, J Appl Physiol, 96:2273-2278; McGuirt A S et al., 1997, Am J Physiol Heart Circ Physiol, 272:H2525-H2533). Such coherence, or lack thereof, is ultimately dependent on intraganglionic interconnections (Hoover D B et al., 2009, Neuroscience, 164:1170-1179; Thompson G W et al., 2000, J Physiol, 528:561-571). The present data indicate that IC network interactions can be targeted therapeutically to modify atrial arrhythmia induction.

VNS therapy not only impacts excitability among select populations of intrinsic cardiac neurons but also the coherence of function displayed among its varied neuronal populations (Kember G et al., 2014, PLoS One, 9:e114498). Before VNS, MNS increased functional connectivity within convergent-to-convergent neuron pairs and between convergent and efferent IC neuron populations. These data suggest that excessive inputs can cascade through the local neural networks with the potential to overwhelm local feedback mechanisms leading to excessive efferent outputs to disparate regions of the heart. This neural signature can be tempered by VNS, primarily via its suppression of convergent IC neural activity. By dampening intrinsic cardiac neural circuits the potential for atrial arrhythmias is reduced.

Unilateral VNS can exert bilateral influences on IC neural function (Beaumont E et al., 2013, J Physiol, 591:4515-4533; Rajendran P S et al., 2016, J Physiol, 594:321-341) and on control of regional cardiac function (Ardell J L et al., 2015, Am J Physiol Heart Circ Physiol, 309:H1740-H1752; Levy M N et al., 1979, Neural control of the heart. In: Handbook of Physiology. The Cardiovascular System. The Heart. Bethesda, Md.: Am Physiol Soc, 1(2), 581-620; Yamakawa K et al., 2015, Am J Physiol Heart Circ Physiol, 309:H1579-H1590). Previous studies have demonstrated that aggregates of the intrinsic ganglionic plexus neurons exert preferential spheres of influence on cardiac indexes, manifested by their direct and indirect projections to cardiomyocytes (Ardell J L et al., 1986, Am J Physiol Heart Circ Physiol, 251:H764-H773; Yuan B X et al., 1993, Cardiovasc Res, 27:760-769; Yuan B X et al., 1994, Anat Rec, 239:75-87). With respect to the RAGP, although it exerts preferential control of sinoatrial nodal pacemaker activity, some of its neurons also influence distant atrial and ventricular electrical and contractile indexes (Ardell J L et al., 1986, Am J Physiol Heart Circ Physiol, 251:H764-H773; Yuan B X et al., 1993, Cardiovasc Res, 27:760-769). Medullary derived parasympathetic efferent preganglionic neurons likewise have spheres of influence (Geis G S et al., 1980, Circ Res, 46:606-611; Gray A L et al., 2004, J Appl Physiol, 96:2279-2287), reflecting their projections onto specific populations of intrinsic cardiac neurons as well as their interactions mediated by interganglionic projections (Armour J A., 2008, Exp Physiol, 93:165-176; Gray A L et al., 2004, J Appl Physiol, 96:2279-2287; McAllen R M et al., 2011, J Physiol, 589:5801-5818; Randall W C et al., 1988, Prog Clin Biol Res, 275:15-31). The present data show that ipsilateral VNS exerts substantially greater antiarrhythmic effects when targeting right atrial neuronal networks than contralateral preganglionic projections to such ganglia (FIG. 8). Without wishing to be bound by any particular theory, this may reflect insufficient preganglionic efferent innervation of respective (contralateral vs. ipsilateral) aggregates of IC neurons (Randall D C et al., 1998, Am J Physiol Regul Integr Comp Physiol, 275:R779-R787; Randall W C et al., 1985, Am J Physiol Heart Circ Physiol, 248:H61-H68; Randall W C et al., 1988, Prog Clin Biol Res, 275:15-31). This anatomical-functional heterogeneity likely underlies any increased AF potential that right-sided ICNS neural imbalance elicits in the presence of left-sided VNS therapy.

VNS and Memory

Regardless of VNS site of delivery, its antiarrhythmic effects exhibit memory. For this study, 3 min of VNS conferred protection for up to 26 min. First and foremost, memory is neural and not myocyte dependent (Ardell J L et al., 2009, Am J Physiol Regul Integr Comp Physiol, 297:R470-R477; Armour J A et al., 2002, Auton Neurosci, 95:71-79; Baddeley A., 2012, Annu Rev Psychol, 63:1-29). It likely involves in the short term local release of neuromodulators and plasticity within local neural network processing (Hardwick J C et al., 2015, Am J Physiol Regul Integr Comp Physiol, 309:R179-R188; Herring N., 2015, Exp Physiol, 100:354-358; Kember G et al., 2013, J Theor Biol, 317:39-46; Kember G et al., 2011, J Theor Biol, 277:41-47; Parsons R L., 2004, Mammalian cardiac ganglia as local integration centers: histochemical and electrophysiological evidence. In: Neural Mechanisms in Cardiovascular Regulation, edited by Dun N J, Machado B H, Pilowsky P M. Boston, Mass.: Kluwer, 335-356) and in the longer term changes in synaptic efficacy (Beaumont E et al., 2015, Am J Physiol Heart Circ Physiol, 309:H1198-H1206; Hardwick J C et al., 2014, Auton Neurosci, 181:4-12). While the precise structure/function mechanisms underlying short- to longer-term effects of VNS on neural function and the nerve/myocyte interface remain poorly defined, future studies should consider potential contributions by muscarinic (Armour J A et al., 2005, Auton Neurosci, 118:68-78; Richer L P et al., 2008, Am J Physiol Regul Integr Comp Physiol, 295:R1175-R1180; Smith F M et al., 2001, Am J Physiol Regul Integr Comp Physiol, 281:R1474-R1482), angiotensin (Hardwick J C et al., 2015, Am J Physiol Regul Integr Comp Physiol, 309:R179-R188; Levett J M et al., 1996, J Surg Res, 66:167-173), and adrenergic (Hardwick J C et al., 2012, Am J Physiol Regul Integr Comp Physiol, 303:R950-R958; Richer L P et al., 2008, Am J Physiol Regul Integr Comp Physiol, 295:R1175-R1180) receptor mechanisms.

Perspectives and Significance

What is clear from recent studies is that there is asymmetry in neural remodeling with progressive cardiac disease and that this neural process is a major determinant of adverse outcomes, including the potential for arrhythmias (Ajijola O A et al., 2015, Heart Rhythm, 12:1027-1035; Chen P S et al., 2014, Circ Res, 114:1500-1515; Fukuda K et al., 2015, Circ Res, 116:2005-2019). The adaptations in neuronal remodeling must likewise be evaluated in terms of the alterations in the cardiac electrophysiological substrate (Chen P S et al., 2014, Circ Res, 114:1500-1515; Gloschat C R et al., 2016, J Physiol, 594:3963-3980). In contradistinction to ablation approaches, a major advantage of electrical neuromodulation when applied at more rostral sites in the cardiac neuraxis is that single point therapy can moderate reflex function in the disparate ganglia within the ICNS (Armour J A., 2008, Exp Physiol, 93:165-176; Randall W C et al., 1988, Prog Clin Biol Res, 275:15-31; Randall W C et al., 1986, Ann Clin Lab Sci, 16:198-208; Zhang Y et al., 2011, Heart Fail Rev, 16:147-161). As demonstrated herein, this form of bioelectric therapy is readily reversible, has a rapid therapeutic onset, and exhibits memory (induces effects that outlast application). For the first time, the pivotal role of local circuit neurons in mediating neurally involved arrhythmias has been defined, and these neurons identified as the primary target for bioelectric medicine.

Example 2: Vagus Nerve Stimulation Mitigates Intrinsic Cardiac Neuronal and Adverse Myocyte Remodeling Postmyocardial Infarction This paper aims to determine whether chronic vagus nerve stimulation (VNS) mitigates myocardial infarction (MI)-induced remodeling of the intrinsic cardiac nervous system (ICNS), along with the cardiac tissue it regulates. Guinea pigs underwent VNS implantation on the right cervical vagus. Two weeks later, MI was produced by ligating the ventral descending coronary artery. VNS stimulation started 7 days post-MI (20 Hz, 0.9±0.2 mA, 14 s on, 48 s off; VNS-MI, n=7) and was compared with time-matched MI animals with sham VNS (MI n=7) vs. untreated controls (n=8). Echocardiograms were performed before and at 90 days post-MI. At termination, IC neuronal intracellular voltage recordings were obtained from whole-mount neuronal plexuses. MI increased left ventricular end systolic volume (LVESV) 30% (P=0.027) and reduced LV ejection fraction (LVEF) 6.5% (P<0.001) at 90 days post-MI compared with baseline. In the VNS-MI group, LVESV and LVEF did not differ from baseline. IC neurons showed depolarization of resting membrane potentials and increased input resistance in MI compared with VNS-MI and sham controls (P<0.05). Neuronal excitability and sensitivity to norepinephrine increased in MI and VNS-MI groups compared with controls (P<0.05). Synaptic efficacy, as determined by evoked responses to stimulating input axons, was reduced in VNS-MI compared with MI or controls (P<0.05). VNS induced changes in myocytes, consistent with enhanced glycogenolysis, and blunted the MI-induced increase in the proapoptotic Bcl-2-associated X protein (P<0.05). VNS mitigates MI-induced remodeling of the ICNS, correspondingly preserving ventricular function via both neural and cardiomyocyte-dependent actions.

The materials and methods employed in these experiments are now described.
Implantation of VNS Systems Eighteen male Hartley guinea pigs (Charles River Laboratories, Wilmington, Mass.), weighing between 500 and 650 g (9 wk old), were implanted with a VNS system comprised of a pulse generator and bipolar lead. Under aseptic conditions, animals were pretreated with atropine (0.1 mg/kg sc) and ketamine (80 mg/kg ip). Thereafter, anesthesia was induced with 3% isoflurane via an induction chamber (VetEquip, Pleasanton, Calif.). Upon removal from the induction chamber, 2.5% isoflurane was delivered via a conical nose cone (VetEquip) until responses to hindlimb toe-pinch stimuli were absent. Following endotracheal intubation, mechanical ventilation was initiated and maintained with a positive pressure ventilator (SAR-830/P ventilator; IITC Life Science, Woodland Hills, Calif.) using 100% $O_2$. Anesthesia was maintained with isoflurane (1-3%). Core body temperature was maintained at 38.5° C. with a circulating water heating pad. Buprenorphine (0.05 mg/kg sc) was administered preoperatively.

Following anesthesia induction, a midline neck incision was made. The right cervical carotid and associated vagus nerve were isolated, and a bipolar VNS electrode (Cyberonics, Houston, Tex.) was positioned around that artery-nerve complex. The lead was secured in place and tunneled to a subcutaneous pocket created over the dorsal aspect of the back where the implantable VNS pulse generator (Demipulse, Model 103; Cyberonics) was positioned. Incisions were closed in layers. Postoperative care included buprenorphine (0.05 mg/kg sc), given as needed, and cefazolin (30 mg/kg im) for 7 days. The pulse generator was inactive for the recovery period (~2 wk).
Surgical Induction of Heart Disease Two weeks later, using techniques detailed previously (Hardwick J C et al., 2014, Auton Neurosci, 181:4-12; Hardwick J C et al., 2008, Am J Physiol Regul Integr Comp Physiol, 295:R1926-R1933), MI was surgically induced by ligation of the ventral descending coronary artery and associated vein in all 18 guinea pigs equipped with a VNS system. Anesthesia and postoperative care were the same as defined above. Previous work (Hardwick J C et al., 2014, Auton Neurosci, 181:4-12; Hardwick J C et al., 2008, Am J Physiol Regul Integr Comp Physiol, 295:R1926-R1933; Dawson T A et al., 2008, Am J Physiol Heart Circ Physiol, 295:H990-H998) has shown that such methodology induces an ~8% infarct. Of 18 animals, two died early on as a direct result of MI, and two were euthanized secondary to necrosis surrounding the pulse generator. Of the remaining 14 animals, following 1 wk of MI recovery, animals were randomized to groups that were either stimulated (VNS-MI group; n=7) or not stimulated (MI group; n=7). All VNS-MI animals were treated with chronic, intermittent (continuously cyclic), low-intensity right cervical VNS (20 Hz pulse frequency, 0.9±0.2 mA pulse amplitude, 500 µs pulse duration, 14 s on time, 48 s off time for 80 days). Age-matched animals without surgery were used as concurrent controls (control group, n=8).

VNS stimulation parameters were chosen to be close to the neural fulcrum, where any effects on heart rate were minimized by the relative effects of VNS on afferent- and efferent-dependent responses (Kember G et al., 2014, PLoS One, 9:e114498). One-third of the animals demonstrated a 5% evoked bradycardia during active-phase VNS. Fifty percent of animals exhibited no significant change in heart rate with VNS. Two animals exhibited a slight tachycardia during active-phase VNS. VNS intensity levels are limited in the guinea pig by effects on water and food intake. In the animals that did not exhibit bradycardia, attempts to increase stimulus intensity further resulted in loss of body weight.
Echocardiography Following sedation with isoflurane (1-2% via nodose cone), short-axis and long-axis echocardiograms were used to determine the left ventricular end systolic volume (LVESV) and the LV ejection fraction (LVEF) for each animal. These measurements were acquired before VNS implant surgery and at 90 days post-MI, just before the terminal experiment.
Terminal Experiments Following echocardiography, animals were euthanized by $CO_2$ inhalation and exsanguination. The heart was removed and placed into ice-cold Krebs-Ringer solution (in mM: NaCl 121, KCl 5.9, $CaCl_2$ 2.5, $MgCl_2$ 1.2, $NaH_2PO_4$ 1.2, $NaHCO_3$ 25, glucose 8, aerated with 95% $O_2$/5% $CO_2$ for a pH of 7.4). The heart and lungs were weighed. The lungs were dried at 37° C. and weighed again (dry lungs). The cardiac nerve plexus, located in the epicardium of the atrial walls, was dissected as described previously (Hardwick J C et al., 1995, J Auton Nerv Syst, 53:166-174). Following dissection, tissue was superfused continuously (6-8 ml/min) with 35-37° C. Krebs-Ringer.

Electrophysiological Methods

Intracellular voltage recordings from IC neurons were obtained with an Axoclamp 2B amplifier (Molecular Devices, Sunnyvale, Calif.) from cells impaled with 3 M KCl-filled glass micropipettes (40-80 MΩ). In the guinea pig model, the IC neurons, recorded with such sharp microelectrodes, are primarily cholinergic in nature (Mawe G M et al., 1996, Cell Tissue Res, 285:281-286). Data were collected, digitized, and analyzed using pCLAMP 10.2 (Molecular Devices). Individual neurons were used for data analysis if the resting membrane potential (RMP) was −40 mV or less and produced action potentials with an overshoot of at least 20 mV (Girasole A E et al., 2011, Am J Physiol Regul Integr Comp Physiol, 301:R1391-R1399). Single action potentials were produced by brief depolarizing current injections (0.7-1.2 nA, 3 ms). Six individual traces were averaged and analyzed to determine afterhyperpolarization (AHP) amplitudes and durations. AHP durations were analyzed to determine the time needed to reach 50% of the amplitude from the peak of the AHP to the RMP. Neuronal input resistance was determined by injecting small hyperpolarizing current pulses of 0.1 and 0.2 nA using 500 ms pulse duration. Neuronal excitability was monitored by observing the number of action potentials generated in response to a series of long depolarizing current pulses (0.1-0.6 nA, 500 ms) before and after brief (1 s) application of NE 10-3 M (Sigma, St. Louis, Mo.), applied by local pressure ejection (4-6 psi; Picospritzer II; General Valve, Fairfield, N.J.) through a small tip diameter (5-10 μm) glass micropipette, positioned 50-100 μm from the individual neuron. The cells were then washed (via the circulating Krebs solution) for several minutes until their response returned to control levels.

To activate synaptic inputs, an extracellular, bipolar, concentric electrode was placed on nerve-fiber bundles leading to the ganglion containing the neuron of interest (Hardwick J C et al., 2014, Auton Neurosci, 181:4-12; Hardwick J C et al., 2012, Am J Physiol Regul Integr Comp Physiol, 303:R950-R958). Orthodromic responses to fiber-tract stimulation (0.1-10 V, 1 ms duration) were determined by the ability to generate an excitatory postsynaptic potential or by the presence of a time delay between the stimulus artifact and the neuronal response. Suprathreshold stimuli leading to action potentials were then given in 2 s trains at frequencies of 1, 2, 5, 10, and 20 Hz, and the number of action potentials produced by the neuron of interest at each stimulus frequency was determined.

Preparation of Heart Homogenate

Concurrently, with the dissection of the cardiac neuronal plexus from the atria, the ventricles were washed briefly in PBS, and ventricular samples from each heart were grossly dissected into three tissue portions and clamped immediately with a set of tongs that was prechilled in liquid nitrogen. The portion (~100 mg) that contained the infarct and some surrounding tissue were designated the central zone (CZ). Moving concentrically away from infarction, an ~350-mg intermediate zone (IZ) and an ~350-mg distal zone (DZ) were also obtained. They were then ground into a fine powder using a mortar and pestle under liquid nitrogen. The powdered heart samples were homogenized in radioimmunoprecipitation assay buffer composed of 50 mM Tris-HCl, pH 7.4 (Calbiochem, Darmstadt, Germany), 1% vol/vol Triton X-100 (Fisher Scientific, Pittsburgh, Pa.), 1% wt/vol sodium deoxycholate (Fisher Scientific), 0.1% wt/vol SDS (EMD Millipore, Billerica, Mass.), and 1 mM EDTA (Fisher Scientific), with 1:40 vol/vol protease inhibitor cocktail mix (Sigma). The homogenates were incubated on ice for 1 h and then centrifuged at 12,000 g at 4° C. for 10 min. The supernatant was collected. Protein concentration for guinea pig heart homogenates was determined using the Pierce BCA Protein Assay Kit (Thermo Fisher Scientific, Rockford, Ill.), according to the manufacturer's protocol.

SDS-PAGE and Western Blot

Phosphorylation status of GSK-3β and its substrate glycogen synthase (GS) was determined from each zone from the MI, VNS-MI, and control guinea pigs, essentially as described previously (Wu J et al., 2013, Am J Physiol Heart Circ Physiol, 305:H821-H828). Western blots were prepared from these gels and probed with antibodies specific for phosphorylated Ser641 of GS (p-GS), GS protein (GS), phosphorylated Ser9 of GSK-3β (p-GSK-3β), GSK-3β protein (GSK-3β), and proapoptotic Bcl-2-associated X (BAX) protein. Protein samples (60 μg/lane) were separated using SDS-PAGE in Pierce Tris-Hepes-SDS 4-20% precast polyacrylamide gels (Thermo Fisher Scientific). Proteins were transferred onto polyvinylidene fluoride membranes (Bio-Rad Laboratories, Richmond, Calif.) at 75 V for 2 h. After transfer, Ponceau (Sigma) staining was used to ensure complete transfer and equal protein loading. Membranes were blocked in 5% nonfat dry milk in Tris-buffered saline (TBS) with 1% Tween 20 (TBS-T) for 1 h at room temperature. GS expression was probed with a rabbit primary MAb at 1:1,000 dilution in TBS-T. Other antibodies were used at the manufacturer's recommended dilutions. Membranes were incubated at 4° C. overnight and washed for 5 min in TBS-T (5x) before incubation with goat anti-rabbit horseradish peroxidase-conjugated secondary antibody. Protein bands were detected using the Pierce SuperSignal West Pico Chemiluminescence Substrate (Thermo Fisher Scientific) in the G:Box Chemiluminescence and Fluorescence Imaging System. Serial exposure times in increments of 10 s were recorded for up to 2 min. For densitometry analysis, lower exposure times were selected to ensure linearity, whereas higher exposures are shown in figures for visual clarity. In some of the figures, blots were cut and rearranged strictly for presentational purposes; however, within rows, images were from the same blot and treated identically. Unless otherwise noted, all antibodies were purchased from Cell Signaling Technology (Beverly, Mass.) and used according to the manufacturer's instructions. Band intensities were quantified using ImageJ software analysis.

Statistical Analysis

Heart function using echocardiography was analyzed with a repeated-measures ANOVA to compare each animal with its baseline condition. The neuronal activity determined by intracellular current injections (see FIG. 12 and FIG. 13) was not normally distributed when analyzed using a Shapiro-Wilk test. A nonparametric Friedman test at the ordinal level and post hoc Wilcoxon signed-rank tests with a Bonferroni correction were done to determine differences among study groups. The data related to tissue weights (see FIG. 10), neuronal transmembrane properties (see FIG. 11), synaptic properties (see FIG. 14B), and myocyte function (see FIG. 15 and FIG. 16) were continuous and normally distributed by using a Shapiro-Wilk test. These data were analyzed using a simple or a mixed-model ANOVA, followed by a Newman-Keuls post hoc analysis. Results with $P<0.05$ were considered statistically significant. Statistical analyses were conducted using SPSS software.

The results of the experiments are now described.

IC Neuronal Properties

The membrane properties of IC neurons derived from MI (n=7; 55 IC neurons), VNS-MI (n=7; 55 IC neurons), and time-matched control guinea pigs (n=8; 64 neurons) are summarized in FIG. 11. A significant depolarization (~5 mV) of the RMP in the MI group was identified compared with controls. VNS was effective in restoring these RMPs to control values. Neuronal input resistance increased significantly in the MI group. VNS mitigated this MI-induced increase in input resistance. There were no significant differences in the amplitude or duration of the AHP half-decay times among IC neurons derived from all three groups.

Figure 12:
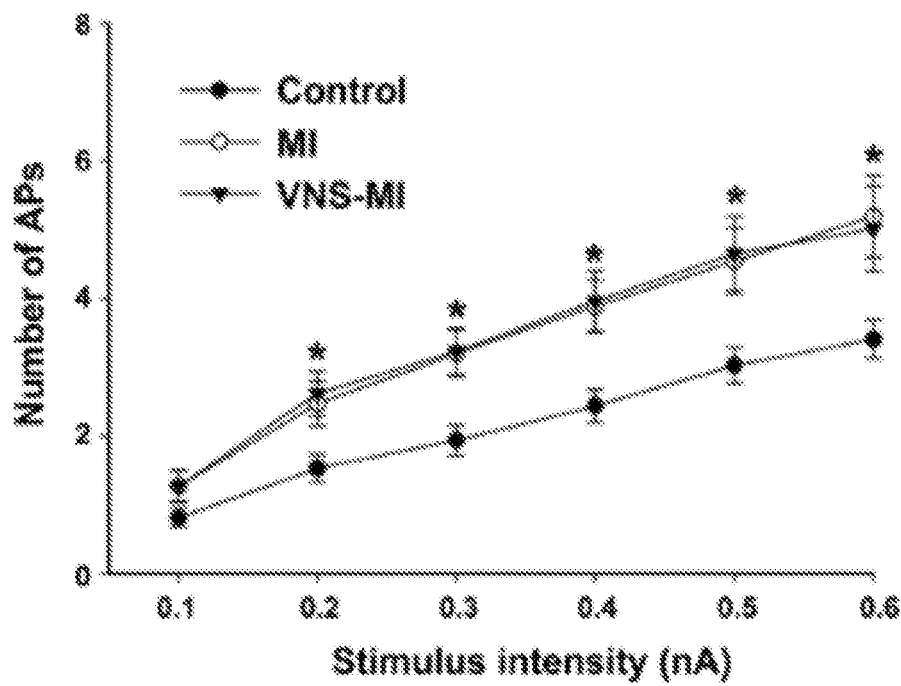
FIG. 12 depicts results from example experiments, demonstrating the number of action potentials (AP) as a function of stimulus intensity (nA), determined by intracellular voltage recordings. Evoked action potential (AP) frequencies with increasing intracellular stimulus intensities (0.1-0.6 nA, 500 ms) were determined by intracellular voltage recordings from intrinsic cardiac (IC) neurons in control preparations, in preparations at 90 days post-myocardial infarction (MI), and in preparations at 90 days post-MI that included 80 days of autonomic regulation therapy (vagus nerve stimulation (VNS)-MI), starting 10 days post-MI induction. A nonparametric Friedman test was used to evaluate difference among groups, followed by Wilcoxon signed-rank post hoc tests using a Bonferroni correction. Points represent the means±SE from ~60 cells for each condition. *$P<0.05$, control vs. MI and VNS-MI.
Figure 13:
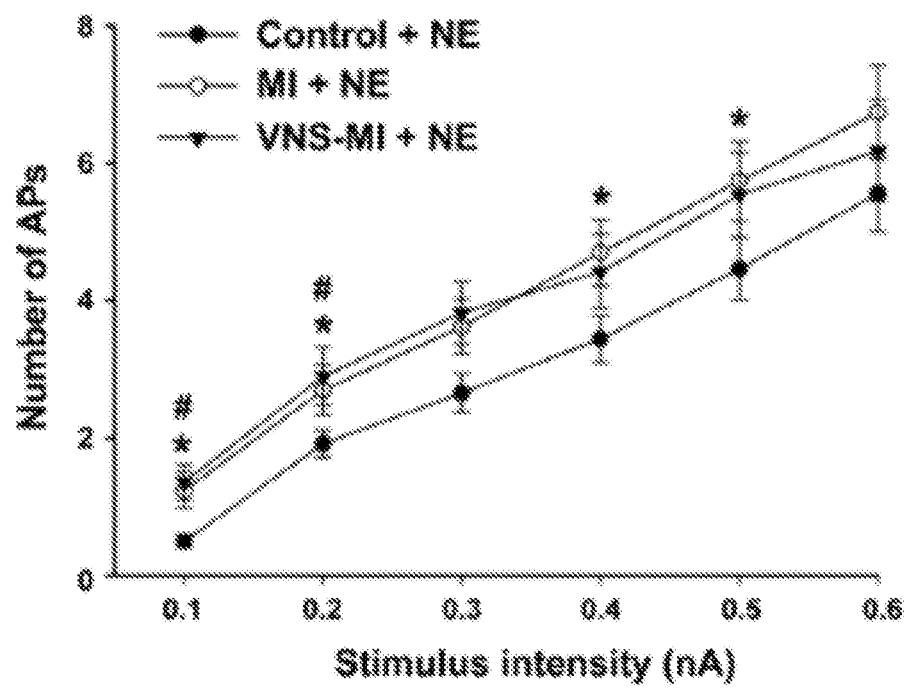
FIG. 13 depicts results from example experiments, demonstrating the number of action potentials (AP) as a function of stimulus intensity (nA), determined by intracellular voltage recordings. Evoked action potential frequencies in response to increasing intracellular stimulus intensities were evaluated, concurrent with brief (1 s), local exposure to exogenous norepinephrine (NE) in IC soma derived from control animals and animals following MI, with and without chronic VNS. A nonparametric Friedman test was used to see differences among groups, followed by Wilcoxon signed-rank post hoc tests using a Bonferroni correction. Points represent the means±SE from ~60 cells for each condition. *$P<0.05$, control vs. MI; #$P<0.05$, control vs. VNS-MI.

Soma excitability was assessed by measuring the number of evoked action potentials in response to intracellular depolarizing current steps. Neuronal excitability increased in MI and VNS-MI groups compared with controls (FIG. 12). Previous studies demonstrated that chronic MI produces an increase in IC neuron sensitivity to NE, as seen in an increase in the number of evoked action potentials in response to depolarizing currents with NE application (Hardwick J C et al., 2008, Am J Physiol Regul Integr Comp Physiol, 295:R1926-R1933). In the current study, IC neuronal sensitivity to NE was increased in the MI group at lower (0.1 and 0.2 nA) and higher (0.4 and 0.5 nA) intensities compared with controls. Neural sensitivity also increased in the VNS-MI group at lower intensities (0.1 and 0.2 nA) compared with controls (FIG. 2).

Synaptic Efficacy

Figure 14:
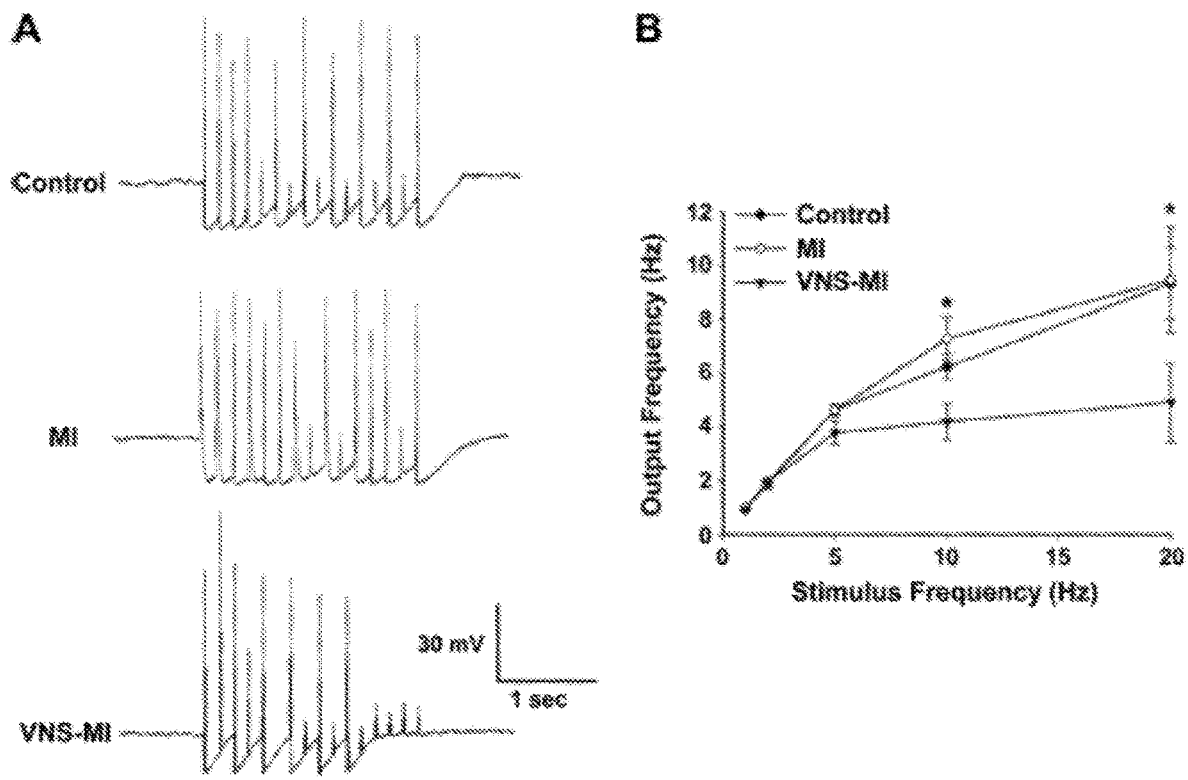
FIG. 14 depicts results from example experiments, demonstrating that chronic VNS reduces synaptic efficacy of IC neurons. Nerve fibers synapsing with the IC neurons were stimulated via an extracellular concentric electrode (0.1-10 V, 2 ms) for 2 s at frequencies of 1, 2, 5, 10, and 20 Hz.

Synaptic efficacy was evaluated among the three groups by measuring neuronal responses to stimulating axon bundles leading to the ganglion containing the neuron of interest (2 s suprathreshold train at 1, 2, 5, 10, and 20 Hz). Whereas the responses between MI and controls did not differ, the number of action potentials so produced was reduced significantly in the VNS-MI compared with MI and control animals (FIG. 14). The maximum neuronal output firing frequency was ~8 Hz in control and MI animals; it was reduced to ~4 Hz with chronic VNS.

Myocyte Function

Figure 15:
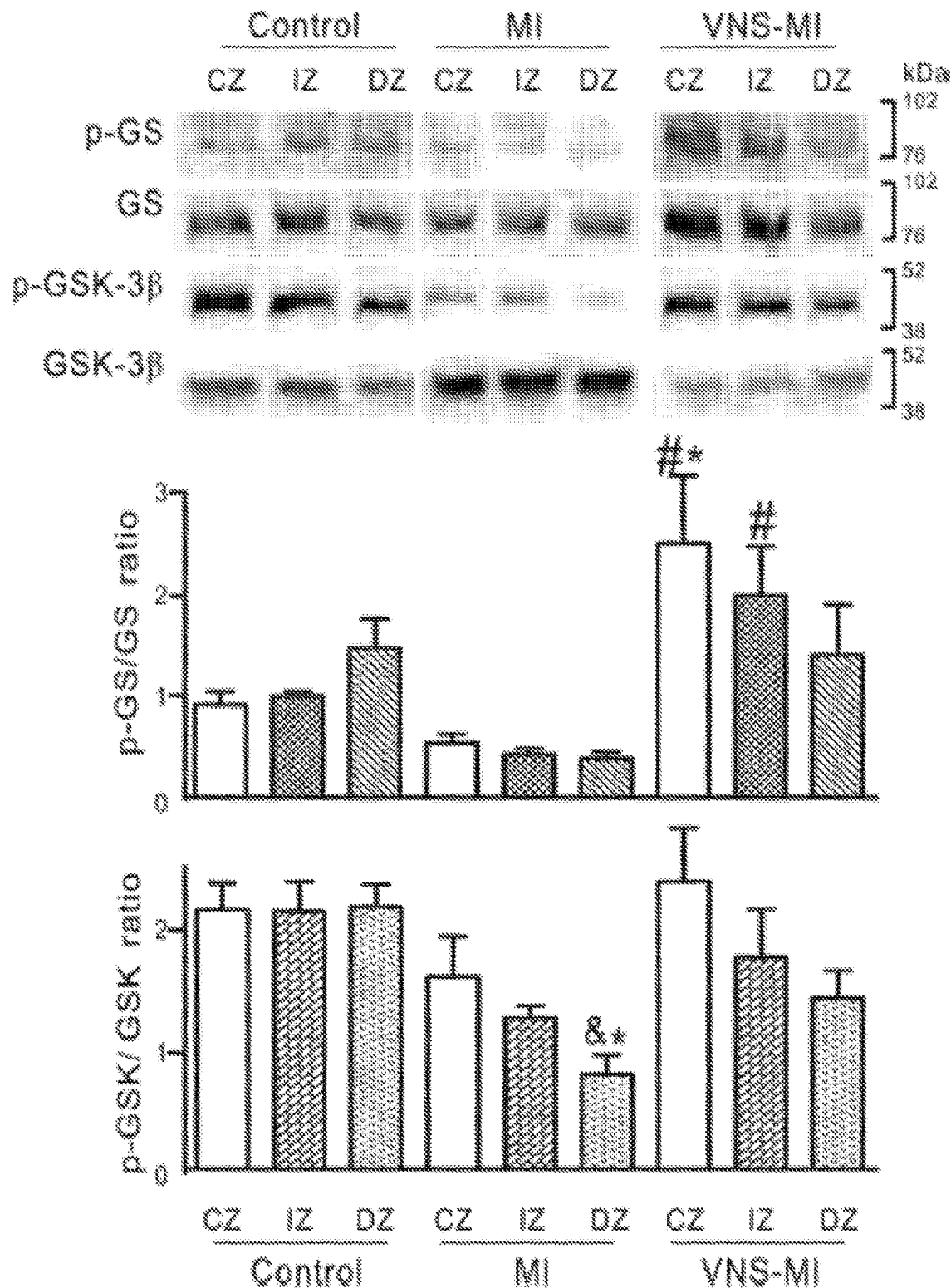
FIG. 15 depicts results from example experiments, demonstrating the phosphorylation status of GSK-3 and its substrate glycogen synthase (GS) in heart tissue derived from the MI (n=5), VNS-MI (n=4), and control (n=3) animals. Shown are representative Western blots probed with antibodies specific for phosphorylated Ser641 of GS (p-GS), GS protein (GS), phosphorylated Ser9 of GSK-3 (p-GSK-3), and GSK-3 protein (GSK-3). Densitometry analysis of protein band intensity was performed for all Westerns. The graphs show the ratio of the p-GS/GS and p-GSK-3/GSK-3, where the protein bands were expressed in arbitrary densitometric units. ANOVA analysis indicating differences among the treatments was followed by Newman-Keuls post hoc analysis. *$P<0.05$ vs. control central zone (CZ), intermediate zone (IZ), and distal zone (DZ); #$P<0.05$ vs. MI-CZ, MI-IZ, and MI-DZ; and & $P<0.05$ vs. VNS-MI-CZ.

Three ventricular tissue samples were removed at time of termination, including from the infarct or CZ, the IZ, and a DZ. The ratio of the p-GS (inactive) to the active form of GS (GS) was determined by Western blot analysis in all three ventricular regions in control, MI, and VNS-MI heart samples. The VNS-MI heart tissue showed a significantly elevated p-GS/GS ratio compared with MI hearts in both the CZ and IZ (FIG. 15). In VNS-MI animals, the p-GS/GS ratio in the CZ was significantly higher compared with control animals (FIG. 15). Besides its role in glycogen metabolism, GS is of interest as a downstream substrate of the key stress signaling kinase, GSK-3β, which is also regulated by phosphorylation. p-GSK-3β is inactive as a kinase but is considered the cardioprotective form of the protein (Tong H et al., 2002, Circ Res, 90:377-379). The ratio of p-GSK-3β/GSK-3 β decreased in the DZ of MI hearts compared with controls; this level was re-established in the CZ of the VNS-MI animals (FIG. 15).

Figure 16:
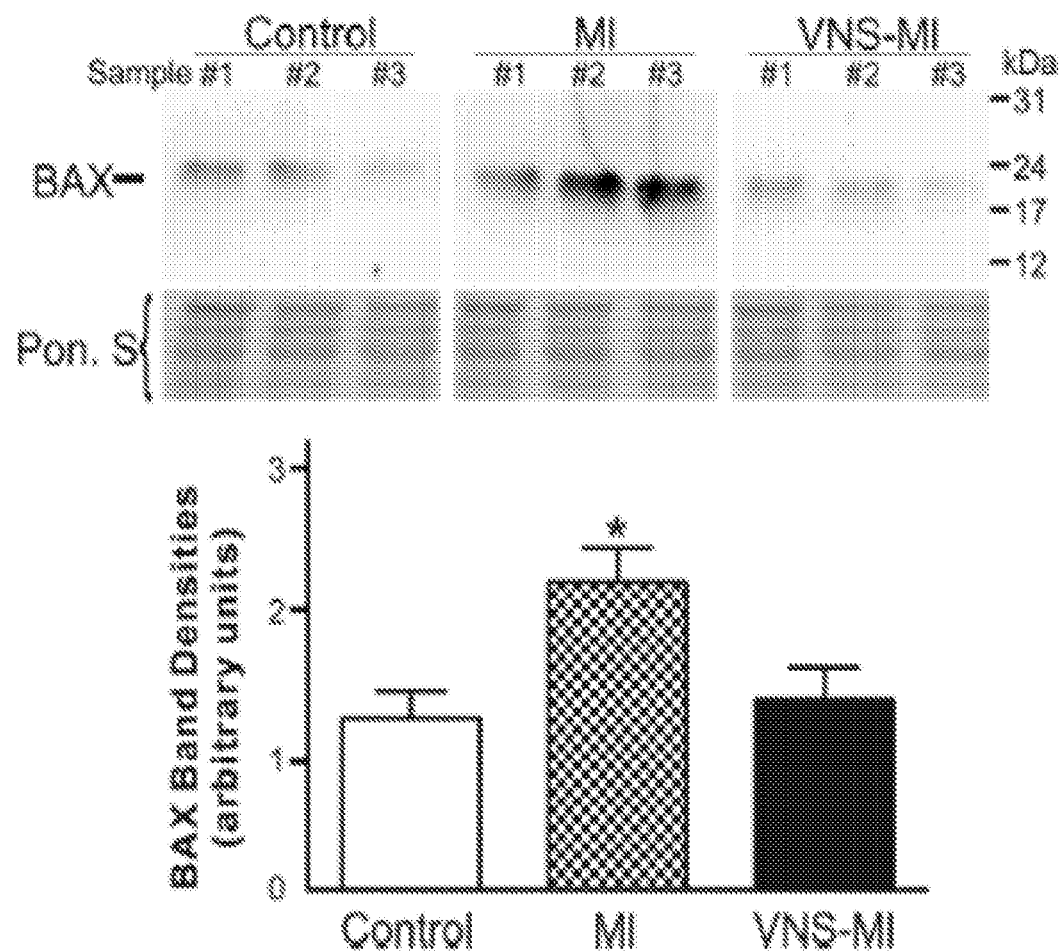
FIG. 16 depicts results from example experiments, demonstrating the elevation of proapoptotic Bcl-2-associated X (BAX) in MI hearts is mitigated by VNS. A representative Western blot probed with antibodies specific for BAX protein is shown (30 µg total protein/lane). The experiment was repeated 4 times with all hearts. The graph shows the densitometry analysis of protein band intensity, which was performed for all Westerns for control (n=3), MI (n=5), and VNS-MI (n=4). The blot stained with Ponceau S (Pon. S) is shown as protein-loading control. ANOVA analysis indicated significant differences among the treatments and was followed by Newman-Keuls post hoc analysis. *$P<0.05$ MI vs. control and VNS-MI hearts.

To evaluate the potential of VNS to exert cardioprotection via modulation of the apoptotic pathway in cardiac myocytes, the expression of several members of the mitochondrial apoptotic machinery were evaluated (Bcl-2, Bcl-xl, and BAX) (Murphy E., 2004, Circ Res, 94:7-16). No significant differences in the levels of Bcl-2 or Bcl-xl were identified (data not shown). However, the level of the proapoptotic protein BAX was elevated twofold in MI hearts. VNS mitigated the increase in BAX level, such that no difference was evident between control and VNS-MI group data (FIG. 16).

Summary

MI remodels both the cardiac nervous system and the cardiac tissue that it modulates. These changes are dynamic, persisting for several weeks after the initial insult (Hardwick J C et al., 2014, Auton Neurosci, 181:4-12; Hardwick J C et al., 2008, Am J Physiol Regul Integr Comp Physiol, 295:R1926-R1933). Associated with the loss of tissue (~8%) post-MI in the guinea pig model (Hardwick J C et al., 2008, Am J Physiol Regul Integr Comp Physiol, 295:R1926-R1933), LVESV increased (30%), and LVEF fell (6.5%). Whereas sufficient to alter contractile function, the level of cardiac damage induced by this MI was not sufficient for progression into congestive heart failure. At the cellular level, IC neurons post-MI displayed depolarization of their RMPs, increases in input resistance, and increased excitability. Since these IC neurons were not in the ischemic zone (i.e., their blood supply was uninterrupted), these IC neuronal changes presumably were a consequence of infarct-induced changes in afferent neuronal feedback to the ICNS (Armour J A., 1999, Cardiovasc Res, 41:41-54; Hardwick J C et al., 2014, Auton Neurosci, 181:4-12; Wang H J et al., 2014, Hypertension, 64:745-755). Presumably, they also reflect an MI reflex-induced decrease in parasympathetic efferent preganglionic neuronal drive (Armour J A., 1999, Cardiovasc Res, 41:41-54; Billman G E et al., 2006, Pharmacol Ther, 111:808-835; Kember G et al., 2013, Physiol Genomics, 45:638-644).

The increase in the parasympathetic efferent neuronal drive to the ICNS by application of chronic VNS restored the IC neuronal RMPs and input resistances toward control values (FIG. 11). Furthermore, VNS also reduced synaptic efficacy by 50% for network interactions within the ICNS. The changes that VNS induced within the ICNS occurred in conjunction with the following: 1) preservation of LV function (as evidenced by echocardiographic data), 2) improvement in cardiomyocyte metabolic capacity, and 3) a reduced potential for ventricular myocyte apoptosis.

Regional LV MI produces an eccentric insult to the heart, which would change afferent neuronal signaling derived from the region where sensory neurites are located, namely, ischemic vs. normal zones. Such altered afferent input is transduced to somata in IC, intrathoracic, and central components of the cardiac neuroaxis (De Ferrari G M, Vanoli E, Schwartz P J. Cardiac vagal activity, myocardial ischemia and sudden death. In: Cardiac Electrophysiology: From Cell to Bedside (2nd ed), edited by Zipes D P and Jalifa J. Philadelphia, Pa.: WB Sanders, 1995, p. 422-434; Foreman R D., 1999, Annu Rev Physiol, 61:143-167; Wang H J et al., 2014, Hypertension, 64:745-755). Such alteration in afferent inputs has the potential to induce reactive changes in neuronal processing throughout the cardiac neuroaxis (Ajijola O A et al., 2013, Am J Physiol Heart Circ Physiol, 305:H1031-H1040; Hopkins D A et al., 2000, Anat Rec, 259:424-436; Wang H J et al., 2014, Hypertension, 64:745-755). With respect to IC neurons, such remodeling is most dynamic at 7 days post-MI, becoming stabilized by 14 days post-MI (Ahonen A et al., 1975, Acta Physiol Scand, 93:336-344; Dobaczewski M et al., 2010, J Mol Cell Cardiol, 48:504-511; Hardwick J C et al., 2014, Auton Neurosci, 181:4-12). In the current study, VNS was initiated during the peak of this remodeling process (cf. 7 days post-MI). As such, this strategy was effective in mitigating not only adverse cardiac functional changes but also targeted MI-induced remodeling of the ICNS.

IC Neuronal Properties

In this study, increased IC neuronal excitability post-MI presumably was due to the following: 1) enhancement in neuronal input resistance, which as a consequence, necessitated lower current density to modify the RMP, and 2) depolarization of the IC neuronal RMP by ~5 mV, thereby decreasing the absolute voltage change needed to induce action potentials. As a consequence, increasing numbers of action potentials were evoked with progressive increases in input stimulus intensities, an effect enhanced by the IC neuronal changes evoked post-MI (Hardwick J C et al., 2014, Auton Neurosci, 181:4-12). The most dramatic effects identified among groups were related to neuronal, following frequencies elicited when stimulating axons innervating IC ganglia containing somata of interest. IC neurons derived from both control and MI groups showed no differences in neuronal output frequencies (FIG. 14). Likewise, whereas MI by itself increases IC soma sensitivity to NE, VNS therapy did not alter it. In contrast, the VNS-MI group showed a dramatic reduction in the efficacy of synaptic transmission within the ICNS, as evidenced by the decrease in activation at equivalent stimulation frequencies.

Previous studies have demonstrated that IC neuronal synaptic efficacy increases in animals subjected to chronic pressure overload (Hardwick J C et al., 2009, Am J Physiol Regul Integr Comp Physiol, 297:R859-R866) or animals, 7 days post-MI (Hardwick J C et al., 2014, Auton Neurosci, 181:4-12). In both cases, neurons were able to follow input frequencies up to ~25 Hz with very good efficacy. This abnormal, high frequency of synaptic transmission in the IC network presumably is, in part, an adaptive response to altered afferent inputs derived from the stressed myocardium (Armour J A, Kember G. Cardiac sensory neurons. In: Basic and Clinical Neurocardiology, edited by Armour J A and Ardell J L. New York: Oxford University Press, 2004, p. 79-117; Fu L W et al., 2009, Handb Exp Pharmacol, 194: 185-225; Wang H J et al., 2014, Hypertension, 64:745-755), with a corresponding decrease in central neuronal drive from medullary parasympathetic efferent preganglionic neurons (Billman G E et al., 2006, Pharmacol Ther, 111:808-835; Brack K E et al., 2013, Heart Fail Rev, 18:389-408; De Ferrari G M, Vanoli E, Schwartz P J. Cardiac vagal activity, myocardial ischemia and sudden death. In: Cardiac Electrophysiology: From Cell to Bedside (2nd ed), edited by Zipes DP and Jalifa J. Philadelphia, Pa.: WB Sanders, 1995, p. 422-434; Zucker I H et al., 2012, Heart Fail Clin, 8:87-99). With the use of chronic VNS to restore biomimetic levels of parasympathetic efferent neuronal drive to the ICNS, synaptic efficacy was reduced by 50%. VNS also activates afferent fibers, with the potential to alter central efferent drive (Bonaz B et al., 2013, Neurogastroenterol Motil, 25:208-221; Buckley U et al., 2015, Curr Heart Fail Rep, 12:284-293). However, it should be recognized that the ICNS will process both exogenously and endogenously derived inputs and thereby functions as a primary target for VNS (Buckley U et al., 2015, Curr Heart Fail Rep, 12:284-293; Shen M J et al., 2015, Heart Fail Clin, 11:337-348). It is postulated that VNS, by reducing IC synaptic efficacy, will blunt network hyperexcitability within the ICNS occurring secondary to ischemia-induced afferent feedback (Kember G et al., 2013, J Theor Biol, 317:39-46; Kember G et al., 2013, Physiol Genomics, 45:638-644). This would be analogous to placing a governor on an internal combustible engine. These neural influences are likely mediated via descending projections to local circuit neurons contained within the ICNS (Beaumont E et al., 2013, J Physiol, 591:4515-4533; Gibbons D D et al., 2012, Am J Physiol Regul Integr Comp Physiol, 302:R357-R364).

The second major neural influence derived from chronic VNS therapy is its antiadrenergic influences. In large animal studies, data demonstrate that peripheral sympathetic-parasympathetic efferent interactions occur within IC ganglia (McGuirt A S et al., 1997, Am J Physiol Heart Circ Physiol, 272:H2525-H2533; Randall D C et al., 2003, Am J Physiol Regul Integr Comp Physiol, 285:R1066-R1075) and at the efferent neural-myocyte interface (both presynaptic (Levy M N. 1971, Circ Res, 29:437-445) and postsynaptic (Lefkowitz R J., 2013, Angew Chem Int Ed Engl, 52:6366-6378)). Both preclinical (Wang Z et al., 2014, Int J Cardiol, 177:676-677; Wang Z et al., 2014, Circ Heart Fail, 7:1014-1021) and clinical (De Ferrari G M et al., 2011, Eur Heart J, 32:847-855; Premchand R K et al., 2014, J Card Fail, 20:808-816) studies indicate that the benefits of VNS can be made manifest at stimulation levels that exert minimal effects on resting heart rate. Since the cervical vagus is a mixed nerve, 80% of which is afferent fibers (Bonaz B et al., 2013, Neurogastroenterol Motil, 25:208-221; Woodbury D M et al., 1990, Epilepsia, 31: Suppl 2:S7-S19), it is the interaction among multiple levels of the cardiac neural hierarchy that ultimately determines functional effects on target organs (Ardell J L. Intrathoracic neuronal regulation of cardiac function In: Basic and Clinical Neurocardiology, edited by Armour J A, Ardell J L. New York: Oxford University Press, 2004, p. 118-152; Armour J A., 2008, Exp Physiol, 93:165-176; Bonaz B et al., 2013, Neurogastroenterol Motil, 25:208-221; McAllen R M et al., 2011, J Physiol, 589:5801-5818).

Cardiomyocyte Function

Examination of the metabolic enzyme markers in ventricular myocytes demonstrated a clear trend of increasing the p-GS/GS ratio in normally perfused tissue located more distal to the arterial ligation in VNS-MI hearts. Increases in the p-GS/GS ratio represent an increase in glycogen use rather than storage via inactivation of glycogen synthetic enzymes. These results indicate that VNS supports glycogen mobilization and glucose use in recovering and/or compensating cardiac tissues. Whereas additional work is needed to ascertain the precise nature of the effects of VNS on such glucose metabolism and whether the increased p-GS/GS ratio indeed represents an upregulation of glycogenolysis, these data suggest that VNS exerts a profound regulatory influence upon glycogen metabolism in the post-MI heart.

Glucose provides more ATP per mole of $O_2$ than free fatty acids (FFA). Shifting metabolism from FFA oxidation to glucose oxidation has been suggested as a therapeutic approach in heart failure (Stanley W C et al., 2005, Physiol Rev, 85:1093-1129; Stanley W C et al., 2005, Heart Fail Rev, 10:275-279). Whereas cardiac tissue has a relatively small pool of glycogen, its turnover rates are high-reported to account for ≤40% of glucose-derived ATP production (Henning S L et al., 1996, Circulation, 93:1549-1555). As mobilization of glycogen stores represents a classic response to ischemia, any increase in phosphorylation of GS post-MI with VNS suggests less glycogen synthesis. This, in turn, implies more glucose use. Since the border and CZs have less $O_2$ availability, glucose therein would be available for anaerobic metabolism.

Multiple stress pathways converge upon GSK-3β, such that it has emerged recently as a pivotal cardioprotective molecule. p-GSK-3β inhibits its kinase activity and increases its cardioprotective potential through poorly understood effects at the mitochondrial level (Tong H et al., 2002, Circ Res, 90:377-379). The current study did not show any decrease in p-GSK-3 in tissue samples with increased p-GS/GS ratios. This finding indicates that increased GSK-3β activity is not responsible for the higher p-GS/GS ratio that was observed in these samples. Since a multitude of other kinases and phosphatases exerts regulatory influence upon GS, any disconnect between the apparent activity of p-GSK-3β and p-GS status is not entirely unexpected. Regardless of the influence of GSK-3β on GS under these particular circumstances, the findings of an increased p-GSK-3β/GSK-3β ratio, as well as the normalization of the mitochondrial proapoptotic protein BAX in VNS-treated hearts, potentially represent important findings pertinent to cardioprotection. These cellular data are especially relevant when considered in light of evidence of improved function of VNS-MI hearts in both small (FIG. 9) and large animal models of ischemic heart disease (Li M et al., 2004, Circulation, 109:120-124; Shinlapawittayatorn K, et al., 2013, Heart Rhythm, 10:1700-1707; Wang Z et al., 2014, Circ Heart Fail, 7:1014-1021).

Significance and Perspectives

VNS is an emerging neuromodulation therapy that is currently being evaluated for treating cardiac arrhythmias (Brack K E et al., 2013, Heart Fail Rev, 18:389-408; Zhang Y et al., 2011, Heart Fail Rev, 16:147-161) and heart failure (De Ferrari G M et al., 2014, Eur J Heart Fail, 16:692-699; Premchand R K et al., 2014, J Card Fail, 20:808-816; Schwartz P J., 2012, Heart, 98:1687-1689). In animal models, the deleterious consequences of MI on cardiac structure and function have been shown to be attenuated by chronic VNS, such that survival improves (Li M et al., 2004, Circulation, 109:120-124; Wang Z et al., 2014, Circ Heart Fail, 7:1014-1021). VNS protects cardiomyocytes against apoptosis (Kakinuma Y et al., 2005, FEBS Lett, 579:2111-2118; Katare R G et al., 2009, J Thorac Cardiovasc Surg, 137:223-231), mitigates mitochondrial dysfunction (Shinlapawittayatorn K, et al., 2013, Heart Rhythm, 10:1700-1707), and reduces the inflammatory responses (Calvillo L et al., 2011, J Cardiovasc Pharmacol, 58:500-507; Wang Q et al., 2012, Inflamm Res, 61:1273-1282). At the level of the ICNS, VNS does not alter MI-induced increases in neuronal excitability; VNS did reduce ICNS synaptic efficacy; and VNS can exert antiadrenergic effects within peripheral autonomic ganglia (McGuirt A S et al., 1997, Am J Physiol Heart Circ Physiol, 272:H2525-H2533; Randall D C et al., 2003, Am J Physiol Regul Integr Comp Physiol, 285:R1066-R1075) and at their end-terminus (Levy M N. 1971, Circ Res, 29:437-445). Together, these effects of VNS would moderate overall network processing within the ICNS in transducing myocardial ischemia to shift the autonomic balance at the neural-myocyte interface away from pathological levels of adrenergic hyperactivity (Armour J A., 2008, Exp Physiol, 93:165-176; Kember G et al., 2014, PLoS One, 9:e114498). VNS, both directly and indirectly (via the nervous hierarchy), improved cardiac myocyte metabolic function, while reducing cardiac myocyte apoptotic state.

VNS is currently in multiple clinical trials for reduced ejection-fraction heart failure (Buckley U et al., 2015, Curr Heart Fail Rep, 12:284-293; De Ferrari G M. 2014, J Cardiovasc Transl Res, 7:310-320). These include the Increase of Vagal Tone in CHF (INOVATE-HF), Neural Cardiac Therapy for Heart Failure (NECTAR-HF), and Autonomic Neural Regulation Therapy to Enhance Myocardial Function in Heart Failure (ANTHEM-HF). Initial results of these trials have been positive for INOVATE-HF and ANTHEM-HF, with neutral effects for NECTAR-HF (De Ferrari G M et al., 2011, Eur Heart J, 32:847-855; De Ferrari G M et al., 2014, Eur J Heart Fail, 16:692-699; Premchand R K et al., 2014, J Card Fail, 20:808-816). One of the key differences among these trials is the choice of stimulation parameters (current, frequency, pulse width, and duty cycle) and especially, the different levels of stimulus intensity. The understanding mechanistically of what is being stimulated within the autonomic nervous system by any bioelectric therapy and how the neural network-heart interface reacts to such stimuli is essential for optimizing stimulation parameters and for the future development of effective autonomic regulation therapies (Buckley U et al., 2015, Curr Heart Fail Rep, 12:284-293). As demonstrated here, targeted VNS exerts multiple effects on the cardiac nervous system and the cardiac tissues it regulates and ultimately, preserves contractile function and as such, cardiac output.

Example 3: Vagus Nerve Stimulation Mitigates Intrinsic Cardiac Neuronal Remodeling and Cardiac Hypertrophy Induced by Chronic Pressure Overload in Guinea Pig The present objective was to determine whether chronic vagus nerve stimulation (VNS) mitigates pressure overload (PO)-induced remodeling of the cardioneural interface. Guinea pigs (n=48) were randomized to right or left cervical vagus (RCV or LCV) implant. After 2 wk, chronic left ventricular PO was induced by partial (15-20%) aortic constriction. Of the 31 animals surviving PO induction, 10 were randomized to RCV VNS, 9 to LCV VNS, and 12 to sham VNS. VNS was delivered at 20 Hz and 1.14±0.03 mA at a 22% duty cycle. VNS commenced 10 days after PO induction and was maintained for 40 days. Time-matched controls (n=9) were evaluated concurrently. Echocardiograms were obtained before and 50 days after PO. At termination, intracellular current-clamp recordings of intrinsic cardiac (IC) neurons were studied in vitro to determine effects of therapy on soma characteristics. Ventricular cardiomyocyte sizes were assessed with histology along with immunoblot analysis of selected proteins in myocardial tissue extracts. In sham-treated animals, PO increased cardiac output (34%, $P<0.004$), as well as systolic (114%, $P<0.04$) and diastolic (49%, $P<0.002$) left ventricular volumes, a hemodynamic response prevented by VNS. PO-induced enhancements of IC synaptic efficacy and muscarinic sensitivity of IC neurons were mitigated by chronic VNS. Increased myocyte size, which doubled in PO ($P<0.05$), was mitigated by RCV. PO hypertrophic myocardium displayed decreased glycogen synthase (GS) protein levels and accumulation of the phosphorylated (inactive) form of GS. These PO-induced changes in GS were moderated by left VNS. Chronic VNS targets IC neurons accompanying PO to obtund associated adverse cardiomyocyte remodeling.

The materials and methods employed in these experiments are now described.

Implantation of VNS Systems

Male Hartley guinea pigs (n=48, 500-650 g body wt, 9 wk of age; Charles River) were implanted with bipolar VNS electrodes connected to a pulse generator. Under aseptic conditions, animals were pretreated with atropine (0.1 mg/kg sc) and ketamine (80 mg/kg ip). Thereafter, anesthesia was induced with 3% isoflurane via an induction chamber (VetEquip, Pleasanton, Calif.). Upon removal of the animals from the induction chamber, 2.5% isoflurane was delivered via a conical nose cone (VetEquip) until responses to hindlimb toe pinch stimuli were absent. After endotracheal intubation, mechanical ventilation was initiated and maintained with a positive-pressure ventilator (model SAR-830/P, IITC Life Science, Woodland Hills, Calif.) using 100% $O_2$. Anesthesia was maintained with isoflurane (1-3%). Core body temperature was maintained at 38.5° C. via a circulating-water heating pad. Buprenorphine (0.05 mg/kg sc) was administered preoperatively.

After anesthesia induction, a midline incision was made in the ventral neck. The right or left vagus nerve and the adjacent carotid arteries were identified and isolated, and a bipolar VNS electrode (PerennialFlex, Cyberonics) was positioned around that artery-nerve complex. The leads were secured in place and tunneled to a subcutaneous pocket created over the dorsal aspect of the back, where the implantable VNS pulse generator (Demipulse, model 103, Cyberonics) was positioned. The incisions were closed in layers. Subsequent postoperative care included buprenorphine (0.05 mg/kg sc as needed) and cefazolin (30 mg/kg im) administered for 7 days. The pulse generator remained inactive during the recovery period (~2 wk duration).

Animal Identification

At the time of VNS system implantation, a 12-gauge needle was used to place a microchip (AVID MicroChip ID Systems, Folsom, La.) into the interscapular subcutaneous space. A MiniTracker (AVID MicroChip ID Systems) scanner was passed over the implant site to detect the identification number assigned to each animal.

Induction of Chronic PO

PO was induced 2 wk after implantation of the VNS stimulator. The anesthetic regimen described above for VNS implantation under aseptic surgical techniques was used to perform a left thoracotomy in the second-third intercostal space to expose the descending thoracic aorta. A 3-0 surgical ligature tied around a metal tube (1-2 mm external diameter and ~1 cm long, made from an 18-gauge needle) placed adjacent to the descending aorta was used to produce uniform constriction of the thoracic aorta. After suture placement to produce the aortic constriction, the metal tube was removed. After placement of a flexible chest tube into the chest cavity and closure of the rib space, local musculature and subcutaneous tissues were closed with absorbable sutures; the skin was closed with nonabsorbable sutures. Once the chest was closed, residual air was withdrawn via the chest tube, the chest tube was removed, and spontaneous ventilation was reinstituted. Postoperative care included administration of buprenorphine (0.05 mg/kg sc) as needed and cefazolin (30 mg/kg im) once per day for the next 7 days. Animals were maintained for (on average) 50 days after PO induction. In this group of PO animals, 17 with PO induction demonstrated clinical signs of pulmonary congestion within a few days; these animals were euthanized within 0-2 days of PO onset and were not included in subsequent data accumulation.

Neuromodulation Therapy

In 19 of these animals, active VNS therapy was initiated 10 days following PO induction: 10 were treated with right-sided [right cervical vagus (RCV)] VNS and 9 with left-sided (left cervical vagus (LCV)) VNS. These groups are designated RCV-PO and LCV-PO, respectively. The parameters chosen for VNS therapy were close to the neural fulcrum, where it was previously demonstrated that any effects on heart rate (HR) are minimized by the combined effects on VNS on afferent and efferent axonal stimulation within the cervical vagosympathetic complex (Ardell J L et al., 2015, Am J Physiol Heart Circ Physiol, 309:H1740-H1752; Beaumont E et al., 2015, Am J Physiol Heart Circ Physiol, 309:H1198-H1206). Continuous cyclic VNS therapy was delivered at a pulse frequency of 20 Hz, 250-μs pulse duration, and 22.5% duty cycle (14 s on-phase and 48 s off-phase). The average current intensity was 1.13±0.04 mA for RCV and 1.17±0.06 mA for LCV. The intensity of stimulation elicited by VNS therapy was limited in the guinea pig over time by its effects on water and/or food intake. In those animals that did not exhibit bradycardia, attempts to further increase stimulus intensity resulted in loss of body weight. In 12 of the animals the VNS system implant remained inactive throughout the 50-day chronic PO induction (sham treatment control group). Time-matched controls (n=9) were also evaluated concurrently with the PO models.

Cardiac Indexes

After sedation with isoflurane (1-2% via nose cone), short-axis echocardiograms were used to determine LV internal diameter at end systole and end diastole, along with estimated LV volume, such that stroke volume could be estimated. These data, along with HR data, were used to derive cardiac output for each animal in the initial and final stages of each experiment. As such, these indexes were determined prior to PO and/or VNS implant, as well as at 50 days after PO just prior to the terminal experiment.

After completion of the echocardiogram, the isoflurane dose was increased to 2.5% until responses to hindlimb toe pinch stimuli were absent. After endotracheal intubation, mechanical ventilation was initiated and maintained with a positive-pressure ventilator (model SAR-830/P, IITC Life Science) using 100% $O_2$. The right carotid artery was isolated, and a 2-Fr pressure-volume catheter connected to a pressure-volume loop single-segment system (MPVS, Millar Instruments, Houston, Tex.) was inserted into it and advanced to the LV. From this catheter, indexes of LV performance, including LV systolic pressure, LV end-diastolic pressure, and rate of change of LV developed pressure (LV +dp/dt and LV −dp/dt) were determined, along with basal HR.

Terminal Experiments

After echocardiographic and LV hemodynamic analyses, animals were euthanized via $CO_2$ inhalation. The heart and lungs were removed rapidly and placed into ice-cold Krebs-Ringer solution (mM: 121 NaCl, 5.9 KCl, 2.5 $CaCl_2$, 1.2 $MgCl_2$, 1.2 $NaH_2PO_4$, 25 $NaHCO_3$, and 8 glucose) aerated with 95% $O_2$-5% $CO_2$ to achieve pH 7.4. Hearts were weighed, and lungs were dried at 37° C. and weighed (dry lungs). The IC nerve plexus, located in the epicardium of dorsal atrial walls, was dissected free of other tissues and placed in a tissue bath, so that the tissues could be continuously superfused (6-8 ml/min) with 35-37° C. Krebs-Ringer solution.

Preparation of Guinea Pig Heart Homogenates and Western Blots

The ventricles from time-matched control, PO, LCV-PO, and RCV-PO guinea pigs were removed and briefly washed in ice-cold PBS to remove blood, and the LV was removed, flash-frozen, and ground into a fine powder using a liquid nitrogen-jacketed mortar and pestle. The frozen heart powder was homogenized in RIPA buffer (50 mM Tris-HCl, pH 7.4 (Calbiochem, Darmstadt, Germany), 1% Triton X-100 (Fisher, Fair Lawn, N.J.), 1% (wt/vol) sodium deoxycholate (Fisher), 0.1% (wt/vol) SDS (EMD, Billerica, Mass.), and 1 mM EDTA (Fisher)) with 1:100 (vol/vol) protease inhibitor cocktail mix (Sigma, St. Louis, Mo.). These homogenates were incubated on ice for 1 h and then centrifuged at 12,000 rpm at 4° C. for 10 min. The supernatant was collected so that the following assays of tissues could be performed.

Protein quantification of lysates was performed on ventricular homogenates using the Pierce bicinchoninic acid protein assay kit (Thermo Scientific, Rockford, Ill.), according to the manufacturer's protocol. Protein samples were subjected to SDS-PAGE using Pierce Tris-HEPES-SDS precast 4-20% polyacrylamide mini gels (Thermo Scientific). Proteins were transferred to polyvinylidene difluoride membranes (Bio-Rad Laboratories, Hercules, Calif.), and Ponceau S (Sigma) staining was used to ensure complete transfer and equal protein loading. Membranes were blocked in 5% nonfat dry milk (Bio-Rad Laboratories) in Tris-buffered saline (TBS) with 0.1% Tween 20 (TBS-T) for 1 h at room temperature.

Phosphorylated Bcl-2-associated death promoter (pBAD) and BAD were exposed to ventricular tissues incubated with rabbit monoclonal primary antibodies diluted 1:1,000 in TBS-T (Cell Signaling Technology, Danvers, Mass.): Bcl-2-associated X (BAX), Bcl-xL, and phosphorylated Akt (pAkt). Glycogen synthase (GS) and phosphorylated GS (pGS) were incubated with rabbit polyclonal primary antibodies diluted 1:1,000 in TBS-T (Cell Signaling Technology). Membranes were incubated in primary antibody at 4° C. overnight. After incubation in primary antibody, the membranes were washed three times for 10 min each in TBS-T before incubation with 1:3,000 goat anti-rabbit horseradish peroxidase-conjugated secondary antibodies (EMD Millipore, Temecula, Calif.) for all the primary antibodies as described above at room temperature for 1 h. Membranes were washed three times in TBS-T for 10 min. Pierce SuperSignal West Pico chemiluminescence substrate (Thermo Scientific) was used for signal detection in the G:BOX imaging system (Syngene, Frederick, Md.). ImageJ software (National Institutes of Health, Bethesda, Md.) was used for densitometry of the protein bands.

Terminal Deoxynucleotide Transferase-Mediated Nick-End Labeling Assay

Ventricular tissue sections were deparaffinized gradually in xylene and ethanol and then fixed in 4% paraformaldehyde and embedded in paraffin (Fisher). Apoptotic guinea pig cardiomyocytes in ventricular tissues were assayed by terminal deoxynucleotide transferase-mediated nick-end labeling (TUNEL) using CardioTACS in situ detection kit (R & D Systems, Minneapolis, Minn.) according to the manufacturer's instructions. Thereafter, TUNEL-positive cardiomyocytes were counted throughout random fields of tissue (×20; Nikon Eclipse TE2000s). ImageJ software was used for myocyte size determinations of paraffin sections stained with Masson's trichrome using standard procedures.

Neuronal Electrophysiological Methods

Neuronal Transmembrane Properties

Intracellular voltage recordings from IC neurons derived from explanted IC ganglia placed in 35-37° C. Krebs-Ringer solution were obtained by impaling cells with 3 M KCl-filled glass micropipettes (40- to 80-MΩ resistance) using an Axoclamp 2B amplifier (Molecular Devices). Data were collected, digitized, and analyzed using pClamp 10.2 (Molecular Devices). Individual neurons were used for data analysis if their resting membrane potential (RMP) was −40 mV or less and produced action potentials (APs) with an overshoot of >20 mV. Input resistance was determined using 0.1- and 0.2-nA pulses (500 ms). Neuronal soma excitability was monitored by observing the response to a series of long depolarizing current pulses (0.1-0.6 nA, 500 ms). The number of evoked APs vs. stimulus intensity was determined to assess relative changes in excitability. Afterhyperpolarization (AHP) durations were analyzed to determine the time to reach 50% of the amplitude from the peak of the AHP to the RMP.

For each cell, after characterization of the basic electrophysiological properties, induced changes in the number of evoked APs by depolarizing pulses were again assessed immediately following a 1- to 2-s application of NE ($10^{-3}$ M; Sigma) or bethanechol (a muscarinic agonist, $10^{-3}$ M; Sigma). Drugs were applied by local pressure ejection (6-9 psi; Picospritzer, General Valve) through small-tip-diameter (5-10 μm) glass micropipettes positioned 50-100 μm from the individual neuron. For multiple tests of responses in the same cell, the cells were allowed to remain in the circulating Krebs solution for several minutes between applications, until the responses returned to control levels.

Neuronal Synaptic Efficacy

To activate synaptic inputs to investigated neurons, a bipolar concentric electrode was placed on nerve bundles connected to the ganglion containing the neuron of interest. Orthodromic responses to fiber tract stimulation (0.1-10 V, 1-ms duration) were assessed by studying 1) the ability of axonal activation to generate an excitatory postsynaptic potential and/or 2) the presence of a time delay between the stimulus artifact and a neuronal response. Suprathreshold stimuli leading to APs were then applied in 2-s trains at varying frequencies (5, 10, 20, and 30 Hz). The number of APs produced by the neuron of interest at each stimulus frequency was assessed.

Statistical Analysis

Cardiac indexes recorded in the control, PO, and different therapy states were analyzed via ANOVA to compare changes induced among different animal groups compared with baseline conditions, as well as among groups. The Holm-Sidak method was used for all pair-wise post hoc multiple comparisons. As neuronal activity was not normally distributed when analyzed using a Shapiro-Wilk test, a nonparametric Friedman's test was utilized at the ordinal level followed by post hoc Wilcoxon's signed-rank tests with Bonferroni's correction to determine differences in neural data obtained in the different study groups. A Shapiro-Wilk test showed data depicting HR and LV pressure indexes (FIG. 17) and tissue weights (FIG. 18), along with neuronal transmembrane properties (FIG. 19) and synaptic properties (see FIG. 22), as well as myocyte structure (see FIG. 24) and function (see FIG. 25, FIG. 26, and FIG. 27), to be continuous and normally distributed. These data were analyzed using a simple or a mixed-model ANOVA followed by a Newman-Keuls post hoc analysis. $P<0.05$ was considered statistically significant. Statistical analyses were conducted using SigmaPlot 12 software.

The results of the experiments are now described.

Hemodynamic Indexes

Figure 20:
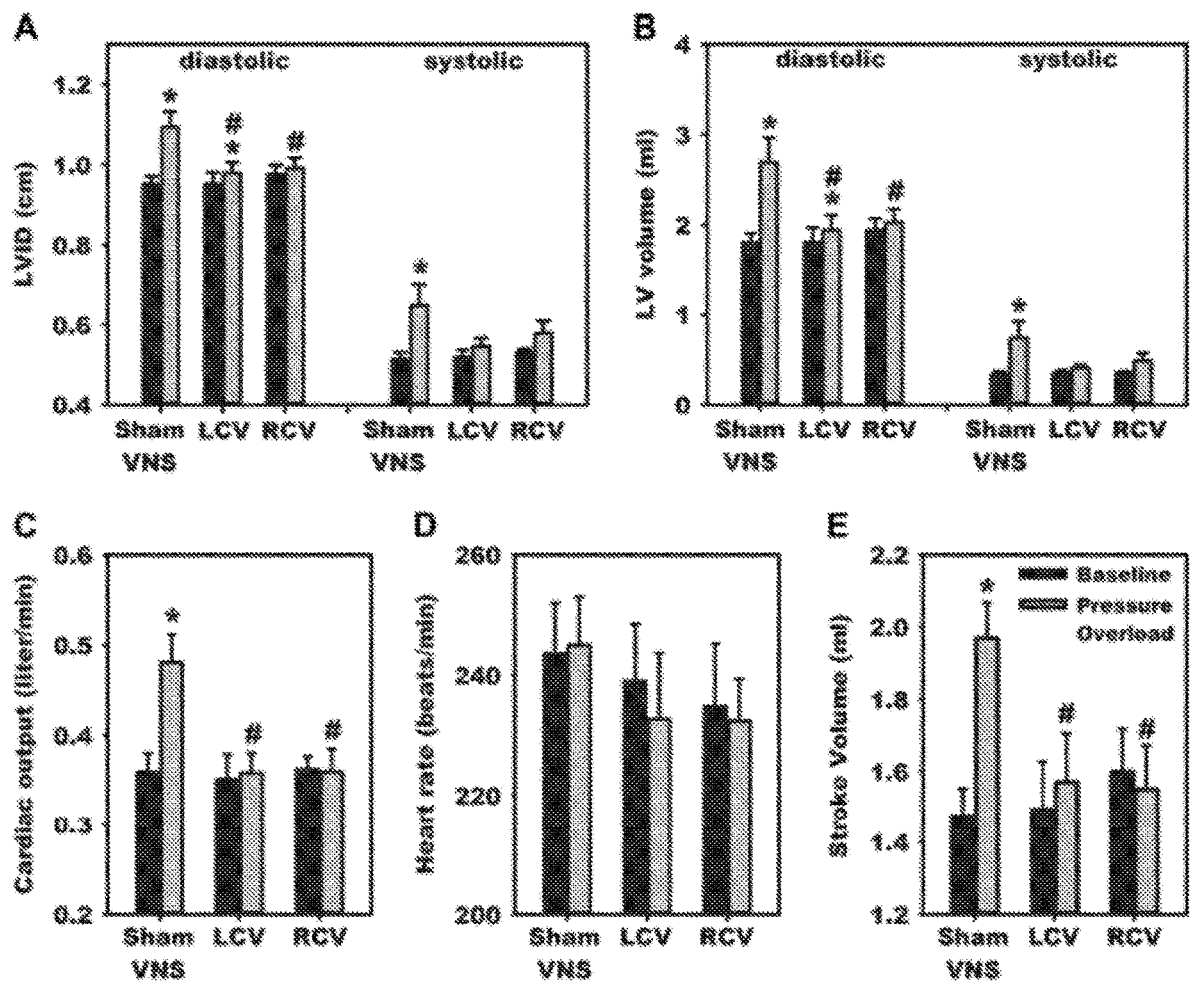
FIG. 20 depicts results from example experiments, demonstrating vagal nerve stimulation (VNS) mitigates pressure overload (PO)-induced hypertrophy and hyperdynamic cardiac behavior. Echocardiographic indexes were determined via a short-axis view at baseline (before) and again at 50 days after PO induction. Treatment groups are as follows: animals with VNS implant, but without active stimulation (sham VNS) and animals in which right cervical vagus (RCV) or left cervical vagus (LCV) stimulation was initiated at 10 days after PO induction and maintained until termination. Cardiac indexes evaluated included left ventricular (LV) internal diameter (LVID.

Paired echocardiographic assessments, from baseline vs. time of termination (51.5±0.5 days after PO induction), demonstrated that LV diameters and volumes (systolic and diastolic) increased significantly in the untreated PO states (FIG. 20). PO likewise was associated with significantly increased LV stroke volume and cardiac output. These PO-induced cardiac changes were minimized by application of chronic VNS, either RCV or LCV. In these three chronic PO groups, LV pressure measurement at termination further indicted that LCV differentially increased LV chamber systolic pressure and ±dp/dt relative to sham VNS or RCV (FIG. 17).

Figure 21:
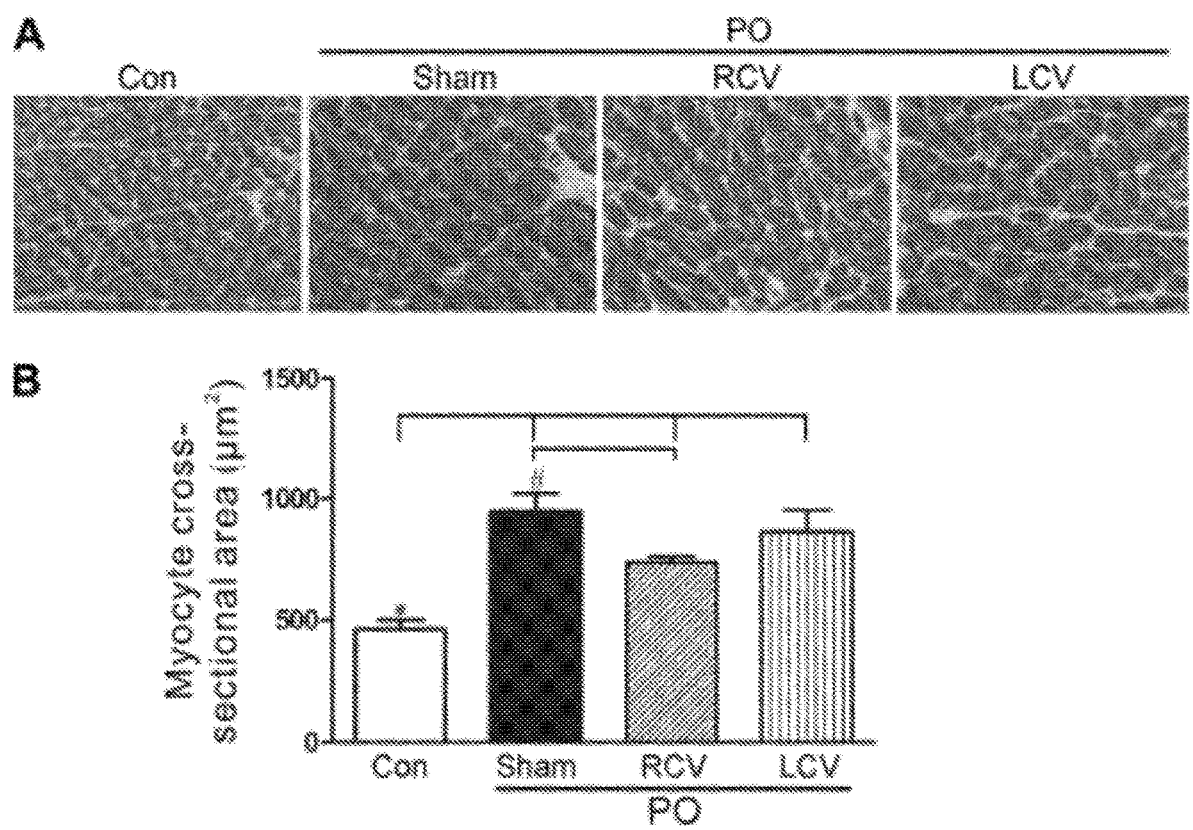
FIG. 21 depicts results from example experiments, demonstrating myocyte hypertrophy associated with PO is significantly reduced by RCV.

In support of echocardiographic data, measurement of LV myocyte cross-sectional area confirmed the PO-induced hypertrophy (FIG. 21). Note the doubling in myocyte size in the sham VNS group, a response that was mitigated by RCV, but not by LCV. In contrast to the myocyte cross-sectional area, no significant differences were found in heart (wet) and lung (wet and dry) weights as a percentage of body weight among treated groups (FIG. 18).

IC Neuronal Transmembrane Properties

The transmembrane potentials of IC neurons derived from controls and PO animals, as well as animals subjected to right (RCV-PO) vs. left (LCV-PO) VNS (including time-matched sham VNS (PO)) are summarized in FIG. 19. No significant differences in the amplitude of AHP or neuronal input resistances were identified among groups. However, cellular RMPs increased (became more negative) in neurons derived from PO animals subjected to RCV compared with controls or animals subjected to PO alone. AHP half-decay time also increased with RCV in the presence of PO compared with the other groups.

Figure 22:
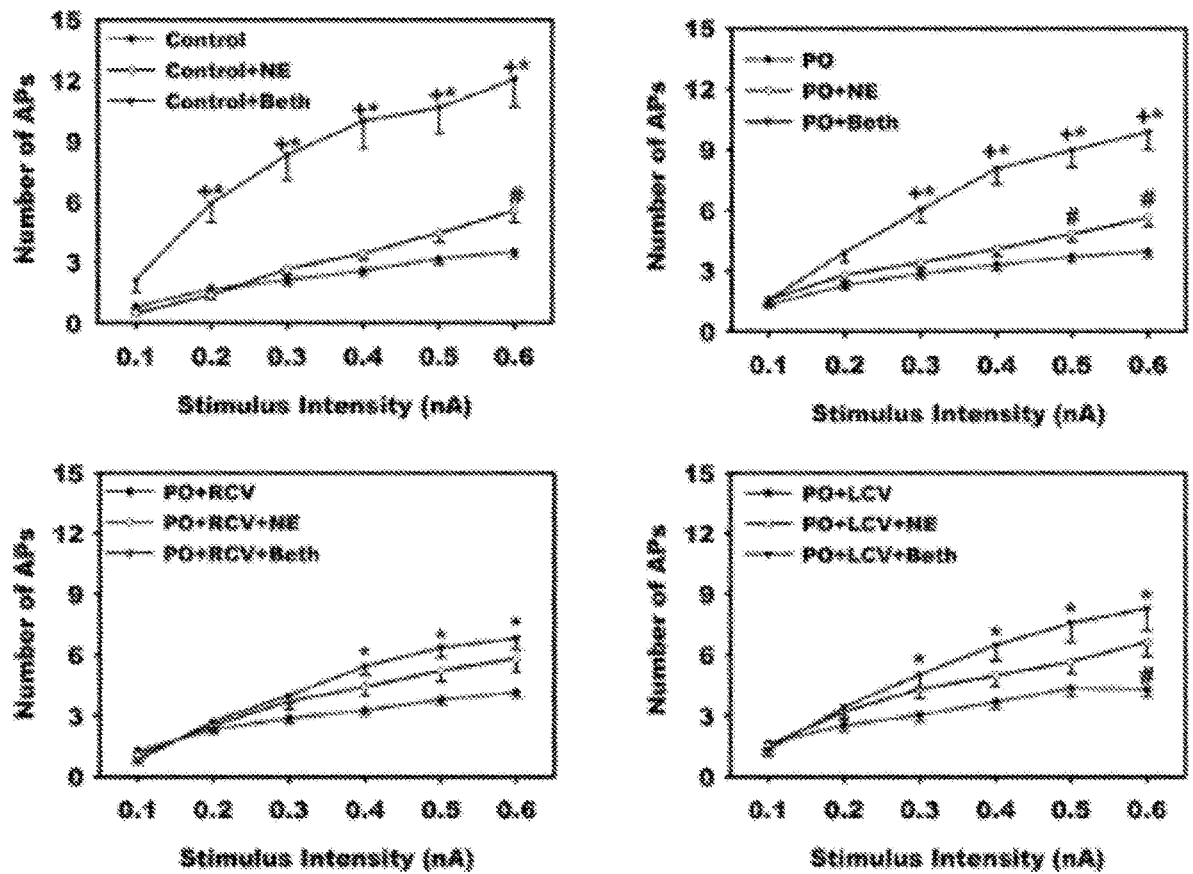
FIG. 22 depicts results from example experiments, demonstrating muscarinic enhancement of neuronal excitability is mitigated with VNS. Evoked action potential (AP) frequencies in response to increasing intracellular stimulus intensities were evaluated concurrently with brief (1–s) local exposure to exogenous norepinephrine (NE) or bethanechol (Beth) in intrinsic cardiac (IC) somata derived from control animals and animals subjected to PO with and without chronic VNS (RCV or LCV). Animals were evaluated 50 days after PO induction. RCV or LCV was initiated 10 days after PO induction and was maintained to termination. Values are means±SE from ~60 cells for each condition. A nonparametric Friedman's test was used to evaluate difference among groups followed by Wilcoxon's signed-rank post hoc tests using Bonferroni's correction. *P<0.05, baseline (control, PO, PO+RCV, or PO+LCV) vs. Beth. +P<0.05, NE vs. Beth. #P<0.05, baseline (control, PO, PO+RCV, or PO+LCV) vs. NE.

Functional excitability of somata, as assessed by measurement of the number of APs evoked in response to intracellular depolarizing current injection steps, was not significantly altered by PO alone or in response to chronic VNS (FIG. 22). Across all groups, changes in IC neuronal sensitivity elicited by local NE application was less than that elicited by bethanecol. Soma excitability to muscarinic agonists was blunted by chronic RCV or LCV (FIG. 22, bottom).

IC Neuronal Synaptic Efficacy

Figure 23:
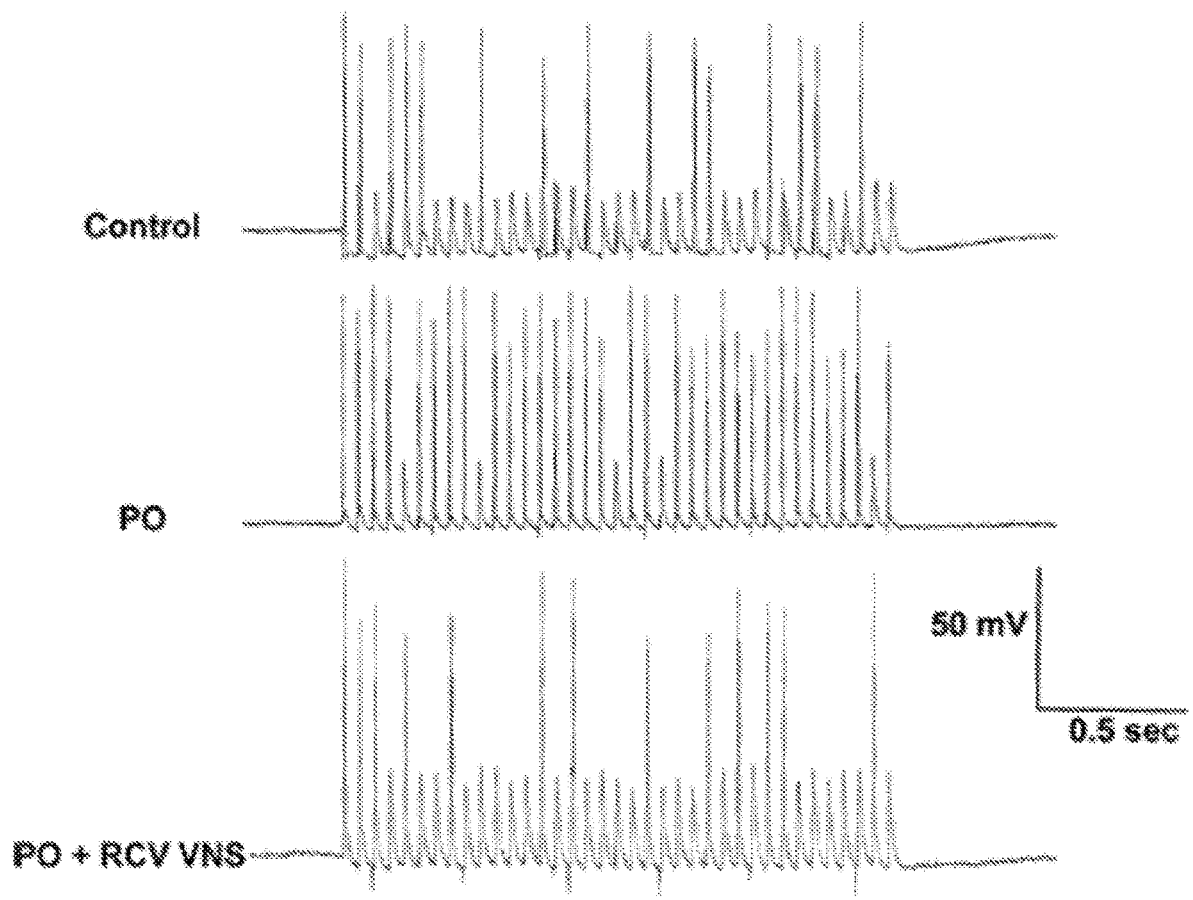
FIG. 23 depicts results from example experiments, demonstrating representative responses of IC neurons to local bioelectric stimulation of primary nerve inputs. Neurons were derived from control, PO, and PO+RCV VNS animal models. Nerve fibers were stimulated at 20 Hz for 2 s.
Figure 24:
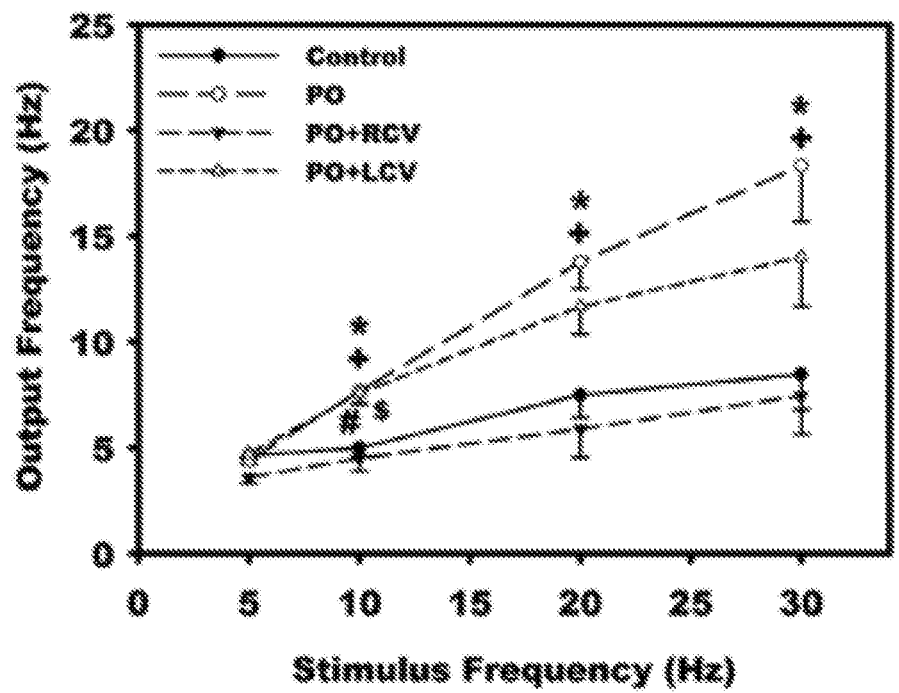
FIG. 24 depicts results from example experiments, demonstrating chronic VNS reduces synaptic efficacy of IC neurons. Nerve fibers synapsing with the IC neurons were stimulated via an extracellular concentric electrode (0.1-10 V, 2 ms) for 2 s at frequencies of 5, 10, 20, and 30 Hz. Values are means±SE from ~30 cells for each condition. *P<0.05, control vs. PO; #P<0.05, control vs. PO+LCV; +P<0.05, PO vs. PO+RCV; $P<0.05, PO+LCV vs. PO+RCV (by ANOVA followed by Newman-Keuls post hoc analysis).

Input synaptic efficacy was evaluated by measuring IC neuronal responsiveness during stimulation of axon bundles associated with the ganglia containing these neurons of interest (FIG. 23). Suprathreshold trains of stimuli (delivered for 2 s at 5, 10, 20, and 30 Hz) resulted in significantly greater output frequencies of neurons derived from PO animals than controls (FIG. 24, control). While RCV restored this index to control values (FIG. 24, PO+RCV), LCV only showed a tendency to reduce the index.

Cardiomyocytes

Figure 25:
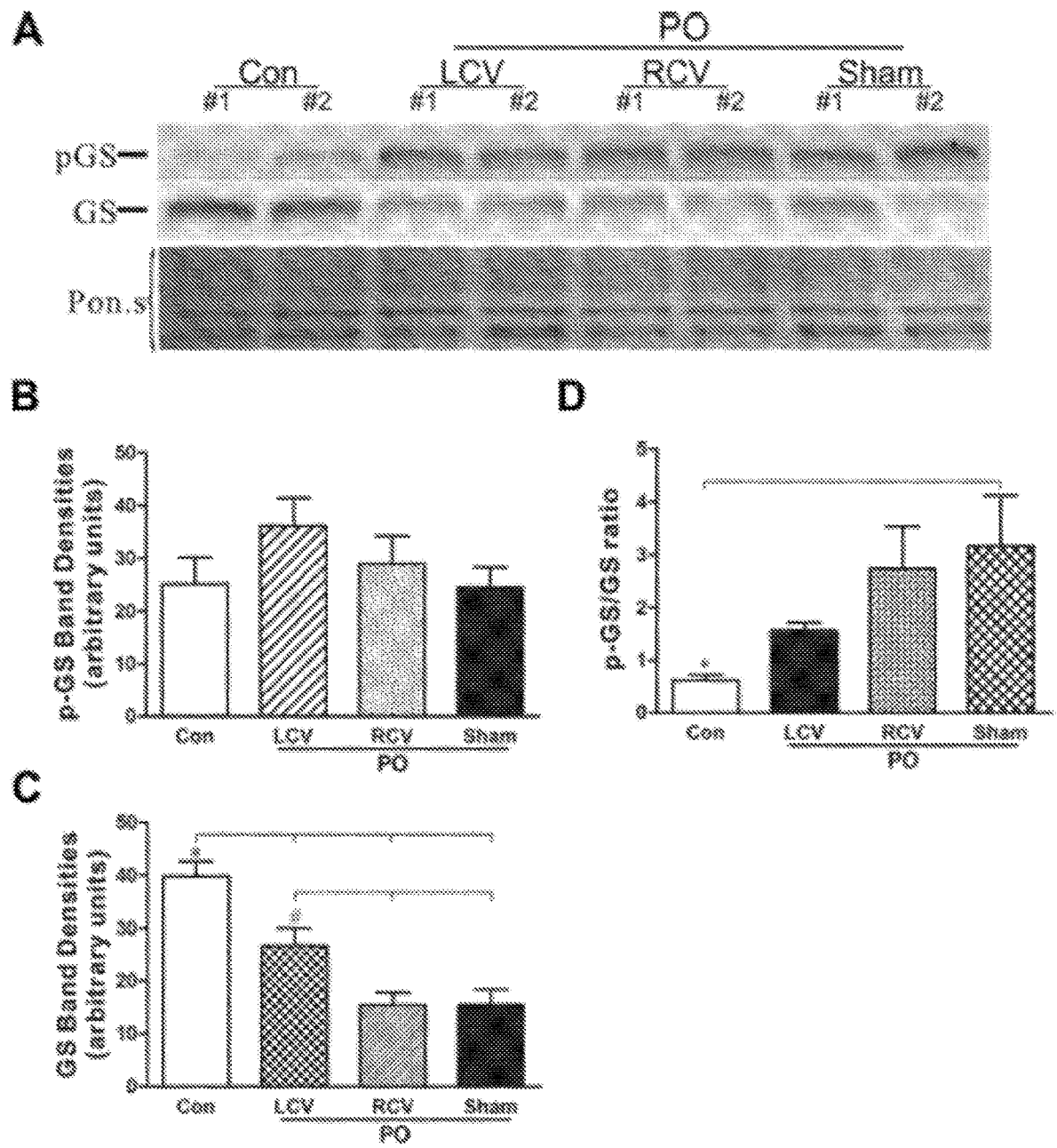
FIG. 25 depicts results from example experiments, demonstrating glycogen synthase (GS) protein levels are significantly reduced and shifted to the inactive phosphorylated form (pGS) in PO; these effects are opposed by left vagus stimulation.
Figure 26:
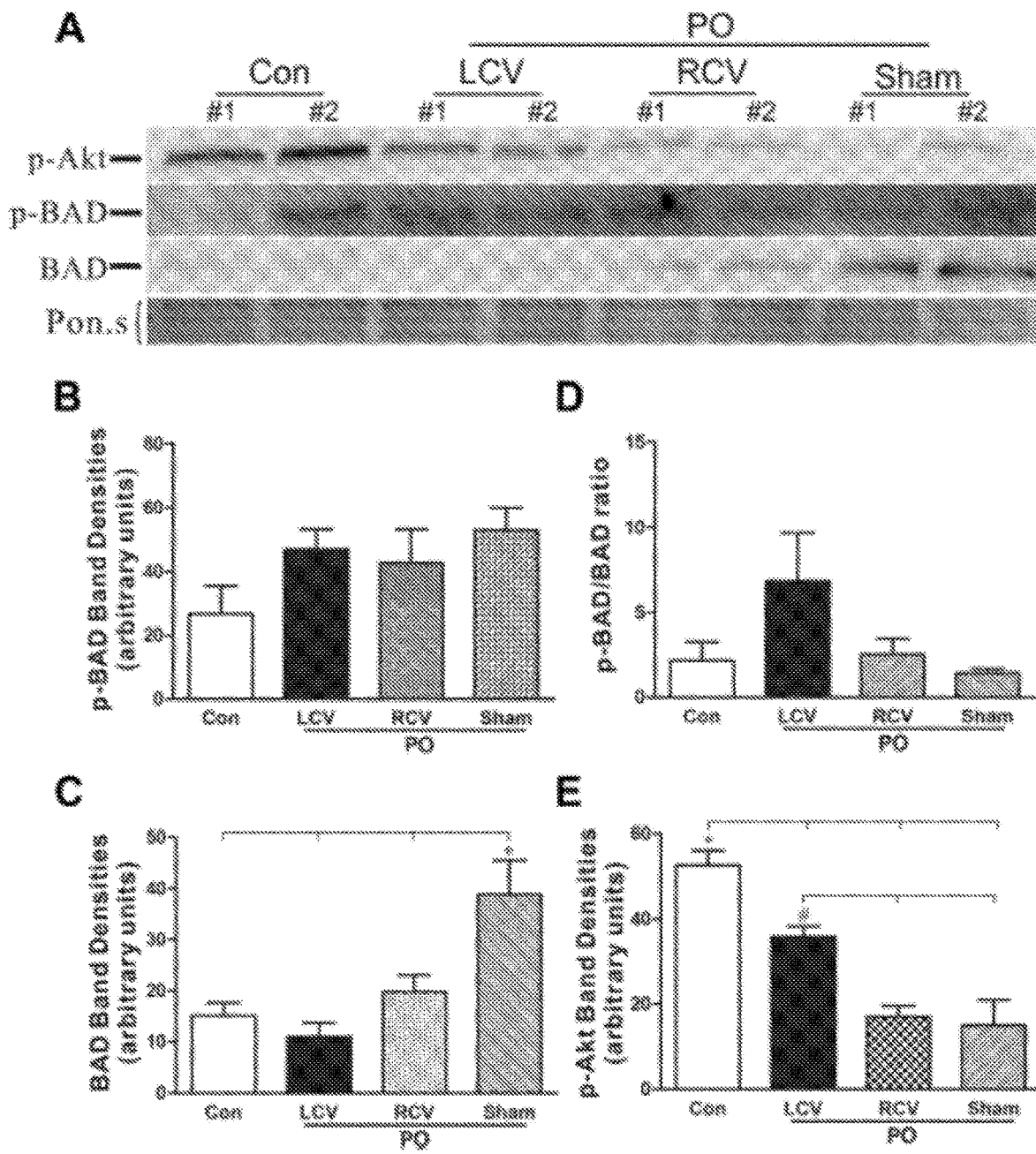
FIG. 26 depicts results from example experiments, demonstrating phosphorylated Akt (pAkt, active form) was decreased and proapoptotic Bcl-2-associated death promoter (BAD) protein level was significantly elevated in the PO heart. LCV partially restored pAkt and BAD protein levels to control values.

Chronic PO alters cardiomyocyte structure and function (FIG. 20 and FIG. 21). One aspect of this remodeling can involve changes in energy utilization (Stanley W C et al., 2005, Physiol Rev, 85:1093-1129). GS protein levels were significantly depressed in PO tissue (FIG. 25). Moreover, the ratio of the inactive pGS to the unphosphorylated GS was increased with PO. These changes are consistent with greater mobilization/utilization of glucose in the PO tissue. The changes in GS expression, induced by PO, were significantly mitigated by LCV, but not by RCV.

Figure 27:
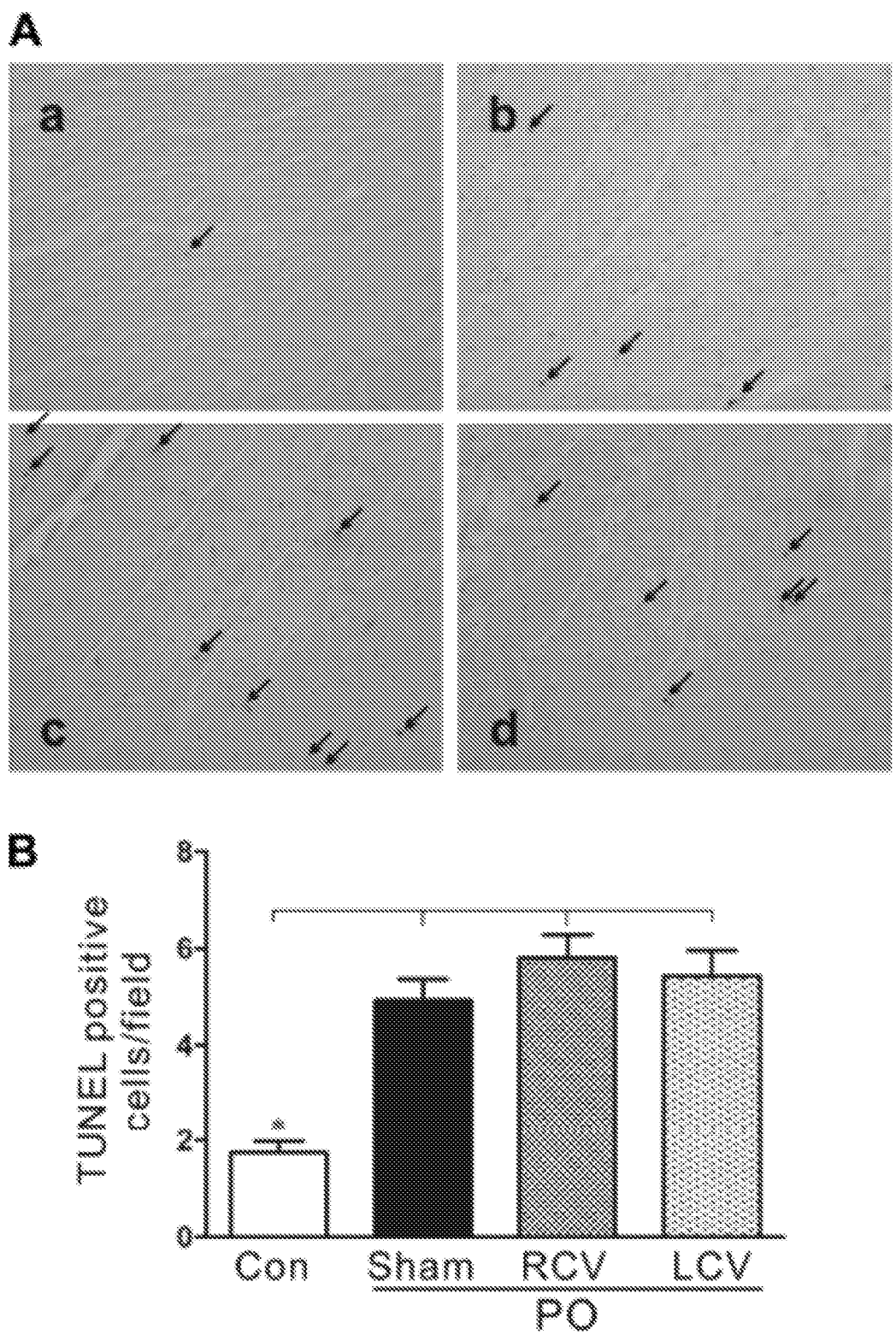
FIG. 27 depicts results from example experiments, demonstrating moderate increases in the number of apoptotic myocytes with PO are unaffected by RCV or LCV therapies.

Apoptosis contributes to the transition from hyperdynamic hypertrophied myocardium to chronic heart failure and the potential for sudden cardiac death (Fukuda K et al., 2015, Circ Res, 116:2005-2019; Houser S R et al., 2012, Circ Res, 111:131-150). The levels of pAkt, the active antiapoptotic form of the kinase, were significantly reduced in PO tissue (FIG. 26E). Chronic LCV significantly blunted this effect of PO on pAkt levels compared with PO-sham VNS. BAX and Bcl-xL levels did not change significantly among the experimental groups (not shown). BAD protein levels were elevated in PO tissue. BAD phosphorylation status did not significantly differ among the experimental groups (FIG. 26B). However, VNS led to significant reductions in gross BAD protein levels (FIG. 26C). While circumstantial, these findings suggest that VNS may exert antiapoptotic effects on the stressed myocardium. This led to the evaluation of the occurrence of apoptosis within the myocardium. Significantly more apoptotic nuclei were found in PO tissue than in control unstressed tissue (FIG. 27). However, VNS had no significant effect on the numbers of myocytes undergoing apoptosis in response to PO stress.

Summary

A critical benchmark for any interventional therapy applied in progressive cardiovascular pathology is ultimately its efficacy to preserve cardiac function, often in the presence of a sustained stressor. Aortic banding provides a model of chronic PO stress that remains throughout (Hardwick J C et al., 2009, Am J Physiol Regul Integr Comp Physiol, 297:R859-R866; Houser S R et al., 2012, Circ Res, 111:131-150). From an echocardiographic perspective, the time point that was evaluated here reflected a hyperdynamic state characterized by a 34% increase in cardiac output with a corresponding increase in systolic and diastolic LV volumes. From a histomorphometric perspective, myocyte cross-sectional area doubled with PO. From an autonomic perspective, withdrawal of central parasympathetic drive coupled with reflex-mediated sympathoexcitation and concurrent activation of angiotensin II contributed to the adverse remodeling (Dell'Italia L J., 2011, Circ Res, 109: 437-452; Hardwick J C et al., 2015, Am J Physiol Regul Integr Comp Physiol, 309:R179-R188; Hardwick J C et al., 2012, Am J Physiol Regul Integr Comp Physiol, 303:R950-R958; Houser S R et al., 2012, Circ Res, 111:131-150). This neurohumoral interplay represents an emerging target for therapeutics (Buckley U et al., 2015, Curr Heart Fail Rep, 12:284-293; Dell'Italia L J., 2011, Circ Res, 109:437-452; Florea V G et al., 2014, Circ Res, 114:1815-1826). This study demonstrated that chronic VNS therapy directly targets the ICNS when appropriately applied, such that LV functional deterioration during the evolution of chronic LV PO is mitigated. The data further indicate that mitigation of adverse PO-induced remodeling involves both myocyte- and neural-dependent mechanisms.

VNS and Cardioprotection

PO-induced heart failure is accompanied by changes in the ventricular metabolic profile, affecting, among other things, a shift to greater reliance on glucose that is associated with downregulation of fatty acid oxidation (Stanley W C et al., 2005, Physiol Rev, 85:1093-1129). An increase in the ratio of inactive pGS to unphosphorylated GS was found during the evolution of chronic PO. This is the first report of a change in GS expression and phosphorylation status by PO. These changes are consistent with greater mobilization/ utilization of glucose in the PO ventricle (Stanley W C et al., 2005, Physiol Rev, 85:1093-1129). Furthermore, changes in ventricular GS expression were mitigated by LCV, but not by RCV. Autonomic neural regulation of glucose and fatty acid metabolism is widely appreciated in liver and skeletal muscle (Nonogaki K., 2000, Diabetologia, 43:533-549) in the context of "rest and digest." For instance, VNS causes a large increase in the activity of liver GS (Shimazu T., 1996, Nutrition, 12:65-66). Direct neural sympathetic effects include stimulation of glycogenolysis in skeletal muscle and liver (Nonogaki K., 2000, Diabetologia, 43:533-549). It is thus surprising that an almost total dearth of information exists concerning autonomic effects on myocardial metabolism. The data indicate that direct neural control of heart metabolism may be profound and that VNS therapy holds the promise of exploiting metabolic regulation to effect better outcomes in intractable pathologies. While further investigation of this issue is warranted, findings concerning ventricular GS changes indicate a reordering of myocardial metabolism in response to VNS, such that the heart becomes more resistant to the pathological stress associated with PO.

Apoptosis and matrix reorganization contribute to the transition from hyperdynamic hypertrophied myocardium to heart failure (Dell'Italia L J., 2011, Circ Res, 109:437-452; Gladden J D et al., 2014, Pflügers Arch 466:1037-1053; Houser S R et al., 2012, Circ Res, 111:131-150). The efficacy of VNS to minimize the proapoptotic BAX in guinea pigs with chronic myocardial infarction was recently reported (Beaumont E et al., 2015, Am J Physiol Heart Circ Physiol, 309:H1198-H1206). By analogy, in the PO model reported here, the levels of pAkt, the active antiapoptotic form of the kinase, were significantly reduced. Importantly, chronic LCV significantly blunted this effect of PO on pAkt levels compared with PO-sham VNS. However, while chronic PO was associated with significantly more apoptotic than normal nuclei, VNS did not reduce this maladaptive response to PO stress. The difference in part may reflect differences mediated by an eccentric ventricular stressor (e.g., myocardial infarction) compared with the concentric stress imposed by PO (Gladden J D et al., 2014, Pflügers Arch 466:1037-1053; Houser S R et al., 2012, Circ Res, 111:131-150; Zucker I H et al., 2012, Heart Fail Clin, 8:87-99). It should be further recognized that many of the proteins evaluated subserve dual roles in both apoptotic and hypertrophic cardiac responses (Matsui T et al., 2003, Cell Cycle, 2:220-223). Taken together, these data suggest that modulation of cardiomyocyte proteins by VNS relates primarily to the hypertrophic response, rather than being dependent on programmed cell death.

VNS and the Autonomic Neuraxis-Cardiac Interface

Neural control of regional cardiac function is dependent on the dynamic interplay between peripheral and central reflexes (Armour J A., 2008, Exp Physiol, 93:165-176; Armour J A, Ardell J L. Basic and Clinical Neurocardiology. New York: Oxford University Press, 2004). The peripheral reflexes involve those contained within the ICNS and within extracardiac autonomic ganglia, including the mediastinal, middle cervical, and stellate ganglia (Armour J A., 2008, Exp Physiol, 93:165-176; Armour J A, Ardell J L. Basic and Clinical Neurocardiology. New York: Oxford University Press, 2004). Central reflex components of the cardiac nervous system include the spinal cord, brainstem, and higher centers (Andresen M C, Kunze D L, Mendelowitz D. Central nervous system regulation of the heart. In: Basic and Clinical Neurocardiology, edited by Armour J A, Ardell J L. New York: Oxford University Press, 2004, p. 187-219; Coote J H., 2013, J Physiol, 591:4073-4085; Harper R M et al., 2012, Anat Rec, 295:1385-1395). Each of these processing nodes contain afferent, efferent, and neural processing neurons, the later referred to as local circuit neurons (Armour J A., 2008, Exp Physiol, 93:165-176). Coordination within these networks allows for effective control of regional cardiac function and the distribution of blood flow throughout the body at baseline and in response to stress (Armour J A., 2008, Exp Physiol, 93:165-176; Kember G et al., 2013, J Theor Biol, 317:39-46; Kember G et al., 2011, J Theor Biol, 277:41-47). Stressors that lead to imbalances within these autonomic networks can lead to disruptions in autonomic outflows, which, in turn, can contribute to adverse remodeling of heart mechanical function and the potential for arrhythmias, including sudden cardiac death (Florea V G et al., 2014, Circ Res, 114:1815-1826; Fukuda K et al., 2015, Circ Res, 116:2005-2019; Kember G et al., 2013, Physiol Genomics, 45: 638-644). The autonomic imbalances, primarily afferent-driven, in turn, are associated with adverse neural remodeling in neural circuits from those on the heart up to and including higher centers up to the insular cortex (Ajijola O A et al., 2015, Heart Rhythm, 12:1027-1035; Hardwick J C et al., 2009, Am J Physiol Regul Integr Comp Physiol, 297:R859-R866; Hopkins D A et al., 2000, Anat Rec, 259:424-436; Kumar R et al., 2011, Eur J Heart Fail, 13: 651-655; Rajendran P S et al., 2016, J Physiol, 594:321-341). Autonomic regulation therapy, of which VNS is one modality, is predicated on targeting specific processing centers to stabilize excessive reflex responses and, thereby, moderate efferent outputs (Ardell J L et al., 2009, Am J Physiol Regul Integr Comp Physiol, 297:R470-R477; Buckley U et al., 2015, Curr Heart Fail Rep, 12:284-293; Foreman R D et al., 2000, Cardiovasc Res, 47:367-375; Vaseghi M et al., 2014, Heart Rhythm, 11:360-366).

The ICNS is the most proximal reflex processor of the cardiac nervous system (Armour J A., 2008, Exp Physiol, 93:165-176). It is primarily associated with short-loop coordination of regional cardiac electrical and mechanical function (Armour J A., 2008, Exp Physiol, 93:165-176). It consists of aggregates on ganglionated plexi that have specific spheres of influence (Ardell J L. Intrathoracic neuronal regulation of cardiac function In: Basic and Clinical Neurocardiology, edited by Armour J A, Ardell J L. New York: Oxford University Press, 2004, p. 118-152; Cardinal R et al., 2009, Auton Neurosci, 145:55-62). The separate aggregates maintain a degree of coordination imposed by local circuit intra- and interganglionic projections, common shared afferent inputs, and descending efferent projections (Ardell J L. Intrathoracic neuronal regulation of cardiac function In: Basic and Clinical Neurocardiology, edited by Armour J A, Ardell J L. New York: Oxford University Press, 2004, p. 118-152; Armour J A, Kember G. Cardiac sensory neurons. In: Basic and Clinical Neurocardiology, edited by Armour J A, Ardell J L. New York: Oxford University Press, 2004, p. 79-117; Beaumont E et al., 2013, J Physiol, 591:4515-4533; Waldmann M et al., 2006, J Appl Physiol, 101:413-419). These efferent projections include sympathetic and parasympathetic efferent axons, with 1) direct connections to postganglionic somata and 2) multisynaptic inputs onto the local circuit (processing) neurons of the ICNS (Beaumont E et al., 2013, J Physiol, 591:4515-4533; Thompson G W et al., 2000, J Physiol, 528:561-571; Waldmann M et al., 2006, J Appl Physiol, 101:413-419). It is recognized that major interactions between sympathetic and parasympathetic efferent neuronal control are exerted at the level of the ICNS and at the end terminus of efferent projections to the heart (Furukawa Y et al., 1996, Am J Physiol Heart Circ Physiol, 271:H44-H50; Levy M N, Martin P J. Neural control of the heart. In: Handbook of Physiology. The Cardiovascular System. The Heart. Bethesda, Md.: Am. Physiol. Soc., 1979, sect. 2, vol. I, p. 581-620; McGuirt A S et al., 1997, Am J Physiol Heart Circ Physiol, 272:H2525-H2533; Randall D C et al., 2003, Am J Physiol Regul Integr Comp Physiol, 285:R1066-R1075). At least in larger animals, vagus projections to the ventricles are widespread and bilateral (Ardell J L et al., 1986, Am J Physiol Heart Circ Physiol, 251:H764-H773; Yamakawa K et al., 2014, Am J Physiol Heart Circ Physiol, 307:H722-H731). In contrast, the sympathetic projections tend to be more unilateral (Ajijola O A et al., 2013, Am J Physiol Heart Circ Physiol, 304: H579-H588; Ardell J L et al., 1988, Am J Physiol Heart Circ Physiol, 255:H1050-H1059). This difference in efferent distribution may explain in part the different efficacy of right vs. left VNS to impact the cardioneural remodeling induced by PO. Regardless, the antiadrenergic effects of VNS are likely a major contributor to the preservation of cardiac function in the setting of ischemic and nonischemic cardiac pathologies.

Cardiac pathologies remodel multiple levels of the neural hierarchy for cardiac control. With respect to heart failure, autonomic regulation is deranged, as usually reflected in sympathoexcitation with a corresponding decrease in central parasympathetic drive (Florea V G et al., 2014, Circ Res, 114:1815-1826; Zucker I H et al., 2012, Heart Fail Clin, 8:87-99). Alterations in neurotransmitter interactions at IC somata in conjunction with alterations in synaptic processing within the ICNS are a reflection of these adaptations (Bibevski S et al., 2011, Heart Fail Rev, 16:129-135; Hardwick J C et al., 2009, Am J Physiol Regul Integr Comp Physiol, 297:R859-R866; Hardwick J C et al., 2015, Am J Physiol Regul Integr Comp Physiol, 309:R179-R188; Hardwick J C et al., 2012, Am J Physiol Regul Integr Comp Physiol, 303:R950-R958). This results in changes in passive and active membrane properties that underlie overall network function. The restoration of synaptic efficacy of IC neurons to "normal" is a reflection of the restraining effects that VNS can exert in peripheral networks. Several potential ionic mechanisms could underlie these neuronal responses. Indeed, several muscarinic receptor-mediated changes in ion currents, including inhibition of the M current, regulation of the delayed rectifier potassium current, inhibition of calcium currents, and enhanced intracellular calcium release, have been described in IC neurons (Adams D J, Cuevas J. Electrophysiological properties of intrinsic cardiac neurons. In: Basic and Clinical Neurocardiology, edited by Armour J A, Ardell J L. New York: Oxford University Press, 2004, p. 1-60; Allen T G et al., 1990, J Physiol, 422:463-480; Beker F et al., 2003, J Neurophysiol, 90:1956-1964; Parsons R L. Mammalian cardiac ganglia as local integration centers: histochemical and electrophysiological evidence. In: Neural Mechanisms in Cardiovascular Regulation, edited by Dun N J, Machado B H, Pilowsky P M. Boston: Kluwer Academic, 2004, p. 335-356). The downward shift in the modulator effects on IC excitability exerted by muscarinic receptors may reflect some of these changes. The specific neuromediators and neuromodulators involved in cardiac disease-induced neural remodeling and, mechanistically, how these are impacted by autonomic regulation therapy remain largely undefined and represent a critical area for future studies.

It is also critical to note that the majority of axons in a cervical vagus are afferent in nature, projecting directly to neurons in the nucleus tractus solitarius of the medulla (Andresen M C, Kunze D L, Mendelowitz D. Central nervous system regulation of the heart. In: Basic and Clinical Neurocardiology, edited by Armour J A, Ardell J L. New York: Oxford University Press, 2004, p. 187-219; Bonaz B et al., 2013, Neurogastroenterol Motil, 25:208-221). By activating such afferent axons with VNS therapy, centrally mediated reflexes target both the sympathetic and parasympathetic efferent neurons controlling the heart (Ardell J L et al., 2015, Am J Physiol Heart Circ Physiol, 309:H1740-H1752; Yamakawa K et al., 2015, Am J Physiol Heart Circ Physiol, 309:H1579-H1590). Recent data indicate that low-level VNS can exert afferent-mediated withdrawal of centrally derived parasympathetic efferent activity (Yamakawa K et al., 2015, Am J Physiol Heart Circ Physiol, 309:H1579-H1590). Further increases in stimulus intensity recruit parasympathetic preganglionic axons with the expected suppression of regional cardiac electrical and mechanical indexes (Ardell J L et al., 2015, Am J Physiol Heart Circ Physiol, 309:H1740-H1752; Levy M N, Martin P J. Neural control of the heart. In: Handbook of Physiology. The Cardiovascular System. The Heart. Bethesda, Md.: Am. Physiol. Soc., 1979, sect. 2, vol. I, p. 581-620). Without wishing to be bound by any theory, it is proposed that the optimum therapeutic parameters for cervical VNS therapy are at the point at which afferent and efferent fibers are activated in a balanced manner, that is, when afferent-mediated decreases in central-mediated parasympathetic drive are counteracted by direct activation of the cardiac parasympathetic efferent projections to the ICNS and heart. At this point, the net result is a null HR response. This has been defined as the neural fulcrum (Ardell J L et al., 2015, Am J Physiol Heart Circ Physiol, 309:H1740-H1752), and the studies presented here utilized this concept to establish the adequacy of the VNS protocol.

Significance and Perspectives

VNS represents an emerging neuromodulation therapy for treating heart failure. Electrical stimulation of the cervical vagosympathetic truck activates ascending and descending axonal projections therein, thus having the potential to impact both central and peripheral aspects of the cardiac neuraxis to modulate cardiomyocytes. The results of this study indicate that, in animal models, the deleterious consequences of long-term PO on cardiac structure/function can be attenuated by chronic VNS therapy. This therapy acts, in part, by directly and reflexly targeting IC neurons to modify their autonomic outflow and, specifically, to counteract the sympathoexcitation induced by PO. VNS, via modulation of the neural-myocyte interface, likewise can render a state of cardioprotection in the stressed heart. This protection, in part, likely reflects induced changes in cardiomyocyte energy pathways.

Example 4: Thoracic Spinal Cord and Cervical Vagosympathetic Neuromodulation Obtund Nodose Sensory Transduction of Myocardial Ischemia Autonomic regulation therapy involving either vagus nerve stimulation (VNS) or spinal cord stimulation (SCS) represents emerging bioelectronic therapies for heart disease. The objective of this study was to determine if VNS and/or SCS modulate primary cardiac afferent sensory transduction of the ischemic myocardium. Using extracellular recordings in 19 anesthetized canines, of 88 neurons evaluated, 36 ventricular-related nodose ganglia sensory neurons were identified by their functional activity response to epicardial touch, chemical activation of their sensory neurites (epicardial veratridine) and great vessel occlusion. Neural responses to 1 min left anterior descending (LAD) coronary artery occlusion (CAO) were then evaluated. These interventions were then studied following either: i) SCS (T1-T3 spinal level; 50 Hz, 90% motor threshold) or ii) cervical VNS (15-20 Hz; 1.2× threshold). Nodose neuronal activity was also assessed at 2 Hz VNS with increasing intensities (1-8 mA). LAD occlusion activated 66% of identified nodose ventricular sensory neurons ($0.33\pm0.08$-$0.79\pm0.19$ Hz; baseline to CAO; $p<0.001$). Their ischemic response was suppressed by SCS ($0.85\pm0.3$-$0.11\pm0.4$ Hz; $p<0.03$) or VNS ($0.74\pm0.26$-$0.11\pm0.05$ Hz; $p<0.03$). Incrementing VNS current from 2 Hz first increased ($0.2\pm0.1$-$0.69\pm0.1$ Hz; $p<0.005$) (1-5 mA) and then decreased ($0.69\pm0.10$-$0.12\pm0.08$ Hz; $p<0.004$) nodose soma activity (5-8 mA). Both VNS and SCS obtund LV ischemia induced enhancement of afferent neuronal inputs to the medulla. The non-linear response of such afferent neurons to progressive VNS indicates that nodose ganglia are not simple sensory relay stations to the medulla; rather they display non-linear neural processing.

The materials and methods employed in these experiments are now described.

Animal Preparation

Mongrel dogs (n=19 of either sex), weighing 17.1-28.0 kg, were employed in this study. All experiments were performed in accordance with the guidelines for animal experimentation described in the "Guiding Principles for Research Involving Animal and Human Beings" (c.f., American Physiological Society's Guiding principles for research involving animals and human beings. Am. J. Physiol. Regulatory Integrative Comp. Physiol. 283: R281-R283, 2002).

Animals were pre-medicated with sodium thiopental (25 mg/kg, i.v.), intubated and maintained under artificial ventilation. Isoflurane (2%) was used as the anesthetic agent during surgery. Following surgery, the anesthesia was changed to α-chloralose (75 mg/kg i.v. bolus, with a constant infusion of 35 mg/kg per hour i.v.). Depth of anesthesia was determined by monitoring corneal reflex, jaw tone and hemodynamic parameters throughout the experiments and maintained by adjustments in anesthetic delivery rates. Body temperature was maintained via a circulating water heating pad (Gaymar T/Pump, Gaymar Industries Inc., Orchard Park, N.Y.). Arterial blood gases were assessed on an hourly basis and adjustments to tidal volume, respiratory rate or doses of sodium bicarbonate performed to maintain adequate oxygenation and homeostasis.

The left femoral artery and vein were catheterized to monitor blood pressure and deliver normal saline and anesthetic agents throughout these experiments. A Mikro-Tip Pressure Transducer catheter (Millar Instruments, Houston, Tex.) was inserted into the right femoral artery and advanced into the left ventricular (LV) chamber to monitor its pressure. Heart rate was monitored via a Lead II electrocardiogram. These indices, along with concurrently recorded afferent neuronal activity from soma contained with the nodose ganglia (see below), were digitalized (Power 1401, Cambridge Electronic Design, Cambridge, England), stored and analyzed offline by the Spike2 program (Cambridge Electronic Design, Cambridge, England).

Spinal Cord Stimulation (SCS)

In a subset of animals (n=6), a spinal cord stimulating electrode was deployed to the upper thoracic cord. Animals were first placed in the prone position and the spinal epidural space penetrated percutaneously with a Touhy needle through a small skin incision at the T6 spinal level. An eight-pole lead (Octrode, Advanced Neuromodulation Systems, Plano, Tex.) was advanced rostrally in the epidural space to the T1-T3 spinal cord level. The tip of the lead was positioned slightly to the left of midline under fluoroscopy. Consistent with current clinical practice (Augustinsson L E et al., 1995, Neurosurg Clin N Am, 6:157-165), the rostral pole was positioned at T1 and the caudal pole was positioned at T3 level. Proper electrode placement was determined by delivering electrical current to the spinal cord via the rostral (cathode) and caudal (anode) poles of the electrode using a PSIU6 constant current isolation unit (Grass Instruments, Quincy, Mass.) connected to a Grass S88 stimulator (Grass Instruments, Quincy, Mass.). Motor threshold (MT) intensity was determined as the lowest current that induced muscle contractions in the proximal forepaw and shoulder. Following SCS electrode implantation the animals were rotated to the supine position and the MT rechecked in that position. SCS was delivered for 20 min at 50 Hz, 200 µs duration and at a current intensity of 90% MT (range 0.25-2.8 mA, mean 0.98±0.19 mA). MT was checked periodically during the experiments. MT did not vary significantly from initial levels throughout each experiment.

Vagus Nerve Stimulation (VNS)

The animals were placed in the prone position and an incision was made in the ventral neck to expose the left cervical vagus. A bipolar stimulating cuff lead (Perennial-Flex model 304, Cyberonics Inc., Houston, Tex.), was wrapped around the left cervical vagosympathetic nerve trunk. Electrical current was delivered to that vagosympathetic nerve via the rostral (anode) and caudal (cathode) poles of the electrode using a PSIU6 constant current isolation unit (Grass Instruments, Quincy, Mass.) connected to a Grass S88 stimulator (Grass Instruments, Quincy, Mass.). Threshold intensity for VNS was determined at 10 Hz and 500 µs as the lowest current that induced a 10% bradycardia. VNS was delivered for 3 min at 15 Hz, 500 µs duration and at a current intensity of 1.2× threshold (range 1-3.5 mA, mean 2.65±0.27 mA). Cardiac threshold was checked periodically during the experiments and remained consistent. VNS was also applied at 2 Hz, 500 µs duration and at a current intensity ranging from 1 to 8 mA to evaluate nodose soma response to graded intensity levels of VNS.

Afferent Neuronal Activity Recording

The activity generated by neuronal soma in the nodose ganglia was studied in all 19 animals using in situ methods reported previously (Armour J A et al., 1994, Cardiovasc Res, 28:1218-1225; Thompson G W et al., 2002, Cardiovasc Res, 53:888-901). Briefly, with the animals in the prone position, and via the incision that was already made in the ventral neck for VNS electrode implant, the left nodose ganglion was visualized. The tissue surrounding the nodose was left intact to stabilize the ganglion during the prolonged recording sessions. A tungsten microelectrode (250 µm diameter and exposed tip of 1 µm; impedance of 9-11 Me), mounted on a micromanipulator, was advanced into the left nodose ganglion using a Microdrive. The electrical signals so derived from this electrode were input into a differential preamplifier (BMA-831, CWE Inc., Ardmore, Pa.) with a high impedance head stage (band width set at 300 Hz to 10 kHz). Signals were further amplified by a battery-driven pre-amplifier (5113 Pre-Amp, Signal Recovery, Oak Ridge, Tenn.) (band width 100 Hz to 2 kHz). Amplified neuronal signals, together with recorded cardiovascular indices, were digitized (Cambridge Electronics Design, power 1401 data acquisition system), stored and analyzed using the Spike 2 software package (Cambridge Electronics Design, Cambridge, England).

Neuronal activity was identified as action potentials with signal to noise ratios greater than 2:1. The activity generated by individual neuronal somata was identified using available spike sorting tools (principal component analysis and cluster on measurements techniques) in the Spike 2 software program. On average 1% of the recorded signals were blanked due to artifact removal using methods detailed elsewhere (Beaumont E et al., 2013, J Physiol, 591:4515-4533; Rajendran P S et al., 2016, J Physiol, 594:321-341). These artifacts included endogenous EKG signals and exogenous signals arising from electrical stimuli. Using these techniques and criteria, action potentials generated by individual somata and/or dendrites, rather than axons of passage, can be recorded for extended periods of time (Armour J A et al., 1994, Cardiovasc Res, 28:1218-1225; Thompson G W et al., 2002, Cardiovasc Res, 53:888-901).

Protocols Employed for Identifying Afferent Neuronal Transduction

Since the nodose ganglia process inputs from intrathoracic and visceral structures, it was first essential to identify those neurons which received ventricular inputs. To this end, loci in different regions of the ventral surface of the ventricle were gently touched for ~10 sec. After waiting 5 min, gauze squares (1 cm×1 cm) soaked with veratridine (100 µM) were applied to the sensory field identified by mechanical stimuli. After waiting 1 min, the chemical-soaked gauze was removed and the epicardium flushed with normal saline. Following 10 min recovery periods, the nodose response to 20s great vessel occlusion (descending aorta and inferior vena cava) was assessed individually. Following another 10 min recovery period, the left anterior descending (LAD) coronary artery was transiently occluded for 60 sec by means of a silk ligature snare placed around that vessel at the level of its first diagonal branch and with at least 20 min separating successive occlusions. From a given recording site within the nodose, if cardiac-related activity could not be evoked, the electrode was moved to another recording site and the stressor protocol detailed above repeated until such time as a cardiac-related sensory neuron was so identified.

Neuromodulation and Nodose Transduction of the Ischemic Myocardium

Two forms of bioelectronics neuromodulation were evaluated, VNS and SCS. The first (VNS) can be considered as "direct" since the cardiac afferent projections to the nodose traverse the neuromodulation site and the later (SCS) remote neuromodulation since the only likely impact would be manifest through SCS-mediated effects to render myocytes stress resistant (Southerland E M et al., 2007, Am J Physiol Heart Circ Physiol, 292:H311-317) and thereby alter the interstitial milieu that is sensed during transient ischemic episodes. To evaluate the effects of SCS on transduction of transient myocardial ischemia, LAD occlusions (60s duration) were done 1 min and 30 min following 20 min of SCS (50 Hz, 200 µs pulse width, 90% MT, n=6). Across all animals, the SCS current intensity at 90% MT was 0.98±0.19 mA and was stable throughout the experiment. In a subset of animals (n=14), a similar protocol was used, but with VNS applied for 3 min at 15 Hz, 500 µs pulse width and 1.2× cardiac threshold. Finally, to address the potential of graded intensity VNS to impact basal neural function, VNS frequency (2 Hz) and pulse width (500 µs) were held constant and intensity progressively increased from 1 to 8 mA. These current intensities cover the range of those used the most recent clinical trials for reduced ejection heart failure (Gold M R et al., 2016, J Am Coll Cardiol, 68:149-158; Premchand R K et al., 2014, J Card Fail, 20:808-816; Zannad F et al., 2015, Eur Heart J, 36:425-433).

Histology and Immunohistochemistry

The left nodose ganglion and either the left or right stellate ganglion were removed in some experiments after euthanizing the animal. This tissue was used to characterize the structure of the nodose ganglion (sensory) relative to that of the stellate ganglion (sympathetic). Tissues were washed in saline, transferred to 10% neutral buffered formalin, and stored for 7 days at 4° C. Extra-nervous tissue was removed from the samples prior to embebbing in paraffin. Samples were sectioned at 5 µm thickness using a Microm HM 310 microtome, and sections were collected on charged slides. Tissue sections were deparaffinized for 1 hr at 60° C. and rehydrated before staining. Representative sections were stained with hematoxylin & eosin (H&E) or immunostained for specific markers.

Slide-mounted sections were immunostained at room temperature using the ABC technique (Vector Laboratories, Burlingame, Calif., USA) as described previously (Downs A M et al., 2014, Neuroscience, 266:178-185; Fregoso S P et al., 2012, Neuroscience, 221:28-36). Prior to immunostaining, tissue sections were treated with Citra Plus antigen retrieval solution per instructions from the manufacturer (Biogenex, San Ramon, Calif., USA). Primary antibodies were used to label the synaptic marker, synaptophysin (goat anti-synaptophysin; 1:200; Cat. No. AF5555; R&D Systems, Inc., Minneapolis, Minn.) and the glial cell marker 51000 calcium binding protein (S100; rabbit anti-S100; 1:2000; Cat. No. Z0311; Dako, Glostrup, Denmark). Localization of the antigen was visualized using the ImmPACT VIP Peroxidase Substrate Kit (Vector). Stained sections were viewed using an Olympus BX4 fluorescence microscope, and digital images were obtained using an attached Olympus Q-Color 3 digital camera and Q-Cap Pro 7 software.

Statistical Analysis

To compare the activity rate generated by each functionally identified neuron before and during each of the interventions depicted, a statistical test based on the Skellam distribution was employed (Shin H C et al., 2010, IEEE Trans Biomed Eng, 57:754-760) and adapted for peripheral autonomic ganglia (Beaumont E et al., 2013, J Physiol, 591:4515-4533; Rajendran P S et al., 2016, J Physiol, 594:321-341). For epicardial mechanical stimuli, great vessel occlusion and coronary artery occlusions, nodose neuronal activity was compared one minute before the stimuli (baseline) vs. during the stimuli. After each stimulus, at least five minutes were allotted for neuronal activity and hemodynamics to return to baseline levels before proceeding. To evaluate the effects of neuromodulation to impact sensory transduction of the ischemic myocardium and to evaluate the effects of graded intensities of VNS on basal nodose activity, repeated measure ANOVA was utilized (SigmaStat, Systat Software, San Jose, Calif.). Conditional probability was then applied to determine whether a nodose neuron that responded to one stimulus also responded to another stimulus, as previously described (Beaumont E et al., 2013, J Physiol, 591:4515-4533). The potential for a functional relationship between stimulus X and Y was quantified within neurons identified in each animal as a conditional probability that a neuron that responded to stimulus Y also responded to stimulus X. The conditional probability (probability: response to Y| response to X) was estimated as the number of neurons that responded to both stimulus X and Y, divided by the number of neurons that responded to stimulus X.

The results of the experiments are now described.

Structure and Organization of Nodose Ganglia

Figure 28:
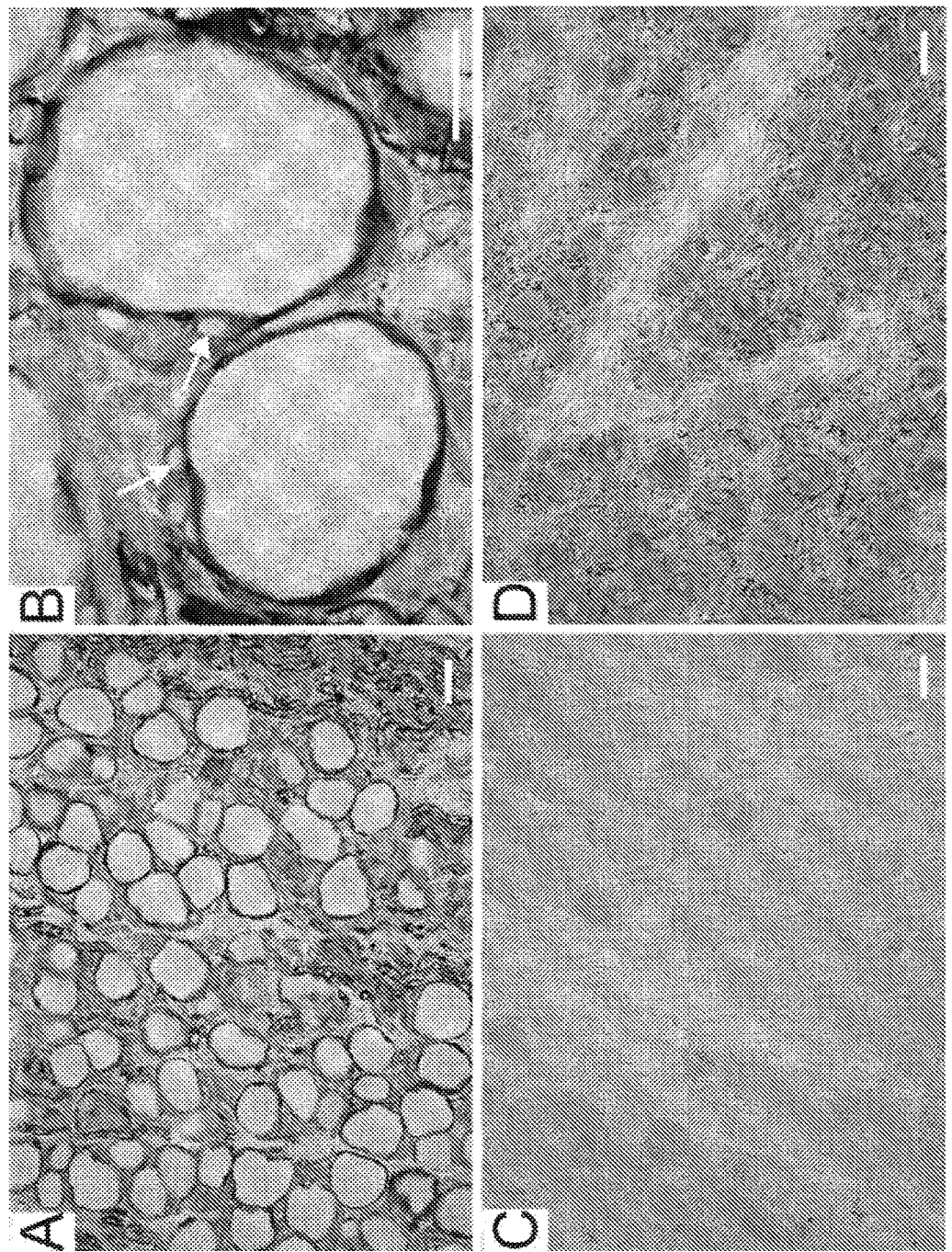
FIG. 28 depicts results from example experiments, demonstrating photomicrographs showing the presence of satellite glial cells surrounding neurons of the nodose ganglion and differential staining for synaptophysin in nodose versus stellate ganglion.

Neurons of the canine nodose ganglia vary in sized but tend to be larger than neurons in the stellate ganglia. Nodose neurons also have a smoother contour than the typical stellate neuron, likely reflecting the absence of dendrites (Hanani M., 2005, Brain Res Brain Res Rev, 48:457-476). Nodose ganglion neurons, like those of all peripheral ganglia, are enveloped by satellite glial cells that stain for S100 (FIG. 28A, FIG. 28B). Schwann cells associated with nerve processes in the nodose ganglia also exhibited S100 immunoreactivity. Staining for synaptophysin demonstrated that synapses are absent in the nodose ganglion (FIG. 28C), whereas synaptophysin-immunoreative varicosities were abundant throughout the stellate ganglion (FIG. 28D).

Nodose Ganglion Afferent Neuronal Activity

Figure 29:
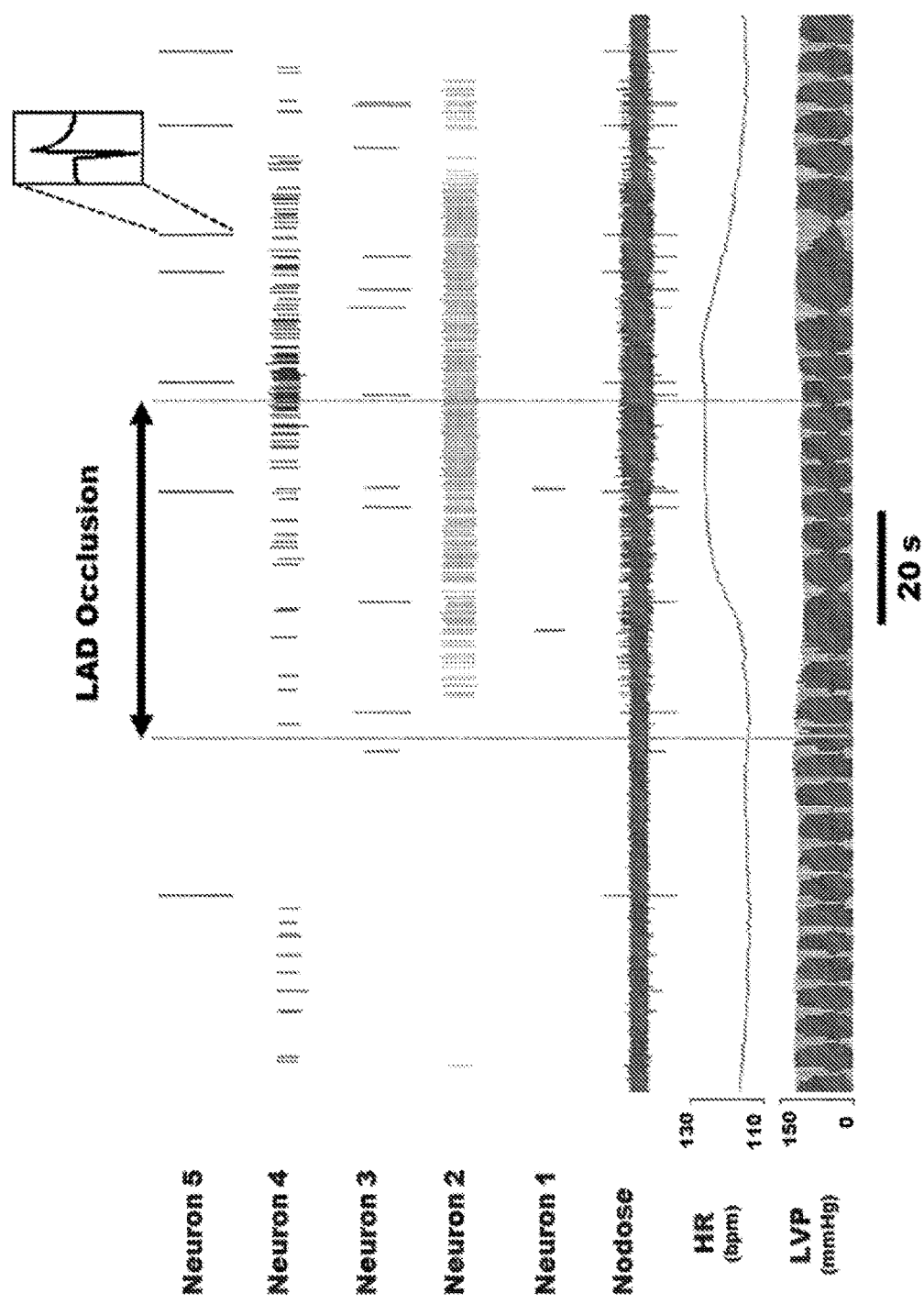
FIG. 29 depicts results from example experiments, demonstrating representative activities generated by 5 different neuronal somata in one nodose ganglion in responses to 1 min of left anterior descending coronary artery occlusion (LAD CAO) (horizontal line on top of record). The activities of these 5 afferent neurons were derived from the grouped activity displayed in the lowest line. Dashed vertical lines illustrate the onset and termination of the transient LAD CAO. The activity generated by 2 identified neurons (#2 & #4) increased in response to LAD CAO as determined by Skellam distribution (see methods). Such enhancement of activity persisted for a short time into the post-reperfusion phase.
Figure 30:
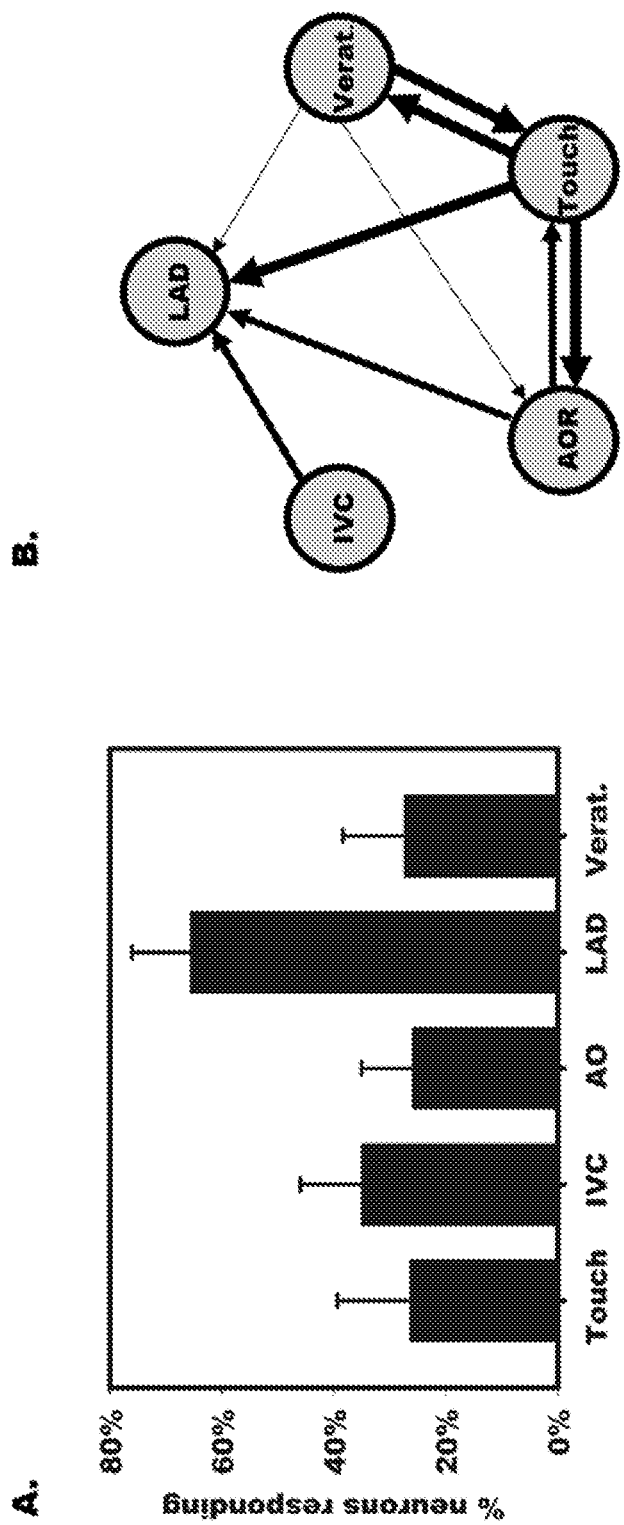
FIG. 30 depicts results from example experiments, demonstrating modality specificity profile for nodose ventricular afferents.

Eighty-eight (88) nodose ganglion afferent neurons (4.6±0.2 per animal) were identified. Thirty-six of the identified neurons (41%) responded with significant activity changes (p<0.05) to at least one of the cardiac stressors imposed (touch, great vessel or coronary occlusion). 52 of the identified nodose neurons (59%) did not respond to any of the stressor tested. FIG. 29 illustrates a typical example from one animal where activity was increased in multiple nodose neurons in response to transient myocardial ischemia. FIG. 30A shows the stratification of functional responses across the population of nodose cardiac-related neurons, with LAD occlusion showing the greatest influence. FIG. 30B shows the conditional probability, across stressors, for modality selectivity. Identification of sensory fields by epicardial touch was highly predictive of subsequent sensitivity to short-term veratradine ($Na^+$ channel activator) placed into that sensory field. Likewise, epicardial touch was predictive of a response to increased mechanical stress associated with the increases in afterload imposed by transient occlusion of the descending aorta. Overall, if a nodose neuron was characterized as cardiac related by mechano-sensitivity, it was likewise modified by LAD occlusion. However, 38% of the cardiac-related nodose neurons (14 of 36) only responded to LAD occlusion, likely reflective of they being nociceptive-related. There was no significant difference in basal activity of the multi-modal ventricular cardiac afferents (0.80±0.41 Hz) vs those that responded only to LAD occlusion (0.46±0.13 Hz). Overall, there were no significant differences in the nodose afferent response to repeat LAD occlusions, each being separated from the previous one by at least 10 min.

VNS and Effects on Nodose Transduction of Vascular Stressors

VNS therapy did not change basal neuronal activity within cardiac-related nodose neurons (0.25±0.15 to 0.2±0.07 Hz; NS). Aortic occlusion-induced changes in neuronal activity in cardiac-related nodose soma were not changed by VNS (0.09±0.03 to 0.19±0.07 Hz 0.09±0.03 vs 0.10±0.04 Hz). Neural response to transient inferior vena cava occlusion were likewise unaffected by VNS (0.18±0.07 to 0.13±0.04 Hz vs 0.16±0.06 to 0.09±0.03 Hz).

VNS and Effects on Nodose Transduction of Myocardial Ischemia

Figure 31:
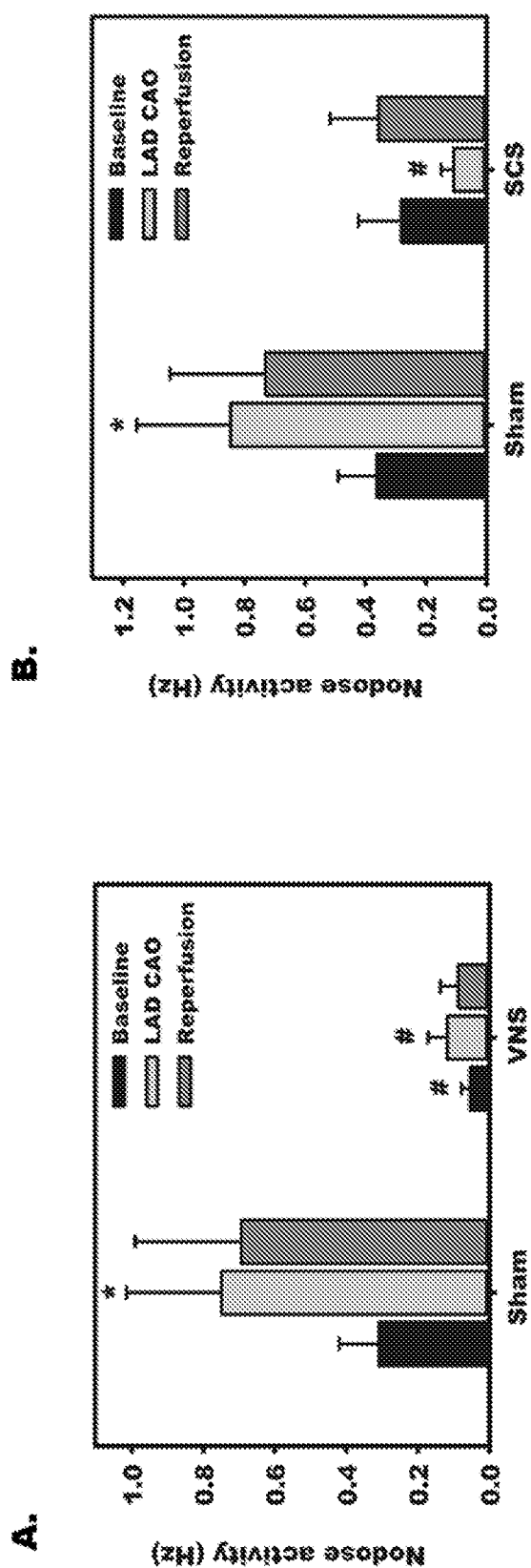
FIG. 31 depicts results from example experiments, demonstrating the effect of vagus nerve stimulation (VNS, FIG. 31A) or spinal cord stimulation (SCS, FIG. 31B) on the evoked response of Nodose cardiac sensory neurons to transient (1 min) left anterior descending (LAD) coronary artery occlusion (CAO). In untreated conditions, transient LAD occlusion activated cardiac afferent neurons. While neither VNS nor SCS impacted basal activity, the evoked neural response to transient myocardial ischemia was abolished by both forms of ART. * $p<0.05$ from baseline; # $p<0.05$ from sham.

Prior to VNS, LAD occlusion increased the activity generated by identified nodose ventricular sensory neurons (0.3±0.11 Hz-0.74±0.26 Hz; $p<0.02$) (FIG. 31A). Following pre-emptive VNS, LAD occlusion no longer increased the activity of identified nodose ganglion afferent neurons (0.05±0.02-0.11±0.05 Hz; $p<0.22$). In fact, VNS decreased the baseline activity generated by these afferent neurons from 0.30±0.74 to 0.05±0.02 Hz ($p<0.04$) (FIG. 31A) and significantly reduced the neural evoked response to transient LAD occlusion (0.74±0.26 vs. 0.11±0.05 Hz, $p<0.03$).

SCS and Effects on Nodose Transduction of Myocardial Ischemia

In the untreated state, transient LAD occlusion increased nodose activity 133% (0.36±0.12 to 0.84±0.3 Hz; $p<0.03$) (FIG. 31B). Following 20 min of preemptive SCS, nodose transduction of the LAD ischemic event was obtunded (0.84±0.3 to 0.10±0.04 Hz; $p<0.03$) (FIG. 31B).

Neuromodulation and Hemodynamic Response to Myocardial Ischemia

In the untreated condition, LAD occlusion increased heart rate and left ventricular (LV) end diastolic pressure (LVEDP) with corresponding decreases in LV end systolic pressure (LVSP) and the maximums (LV +dp/dt) and minimums (LV −dp/dt) in the first derivative of LV pressure change (FIG. 29 and FIG. 33). Neither VNS nor SCS altered the overall hemodynamic response to one min of LAD occlusion (FIG. 33).

VNS and Effects of Graded Intensity of Basal Activity

Figure 32:
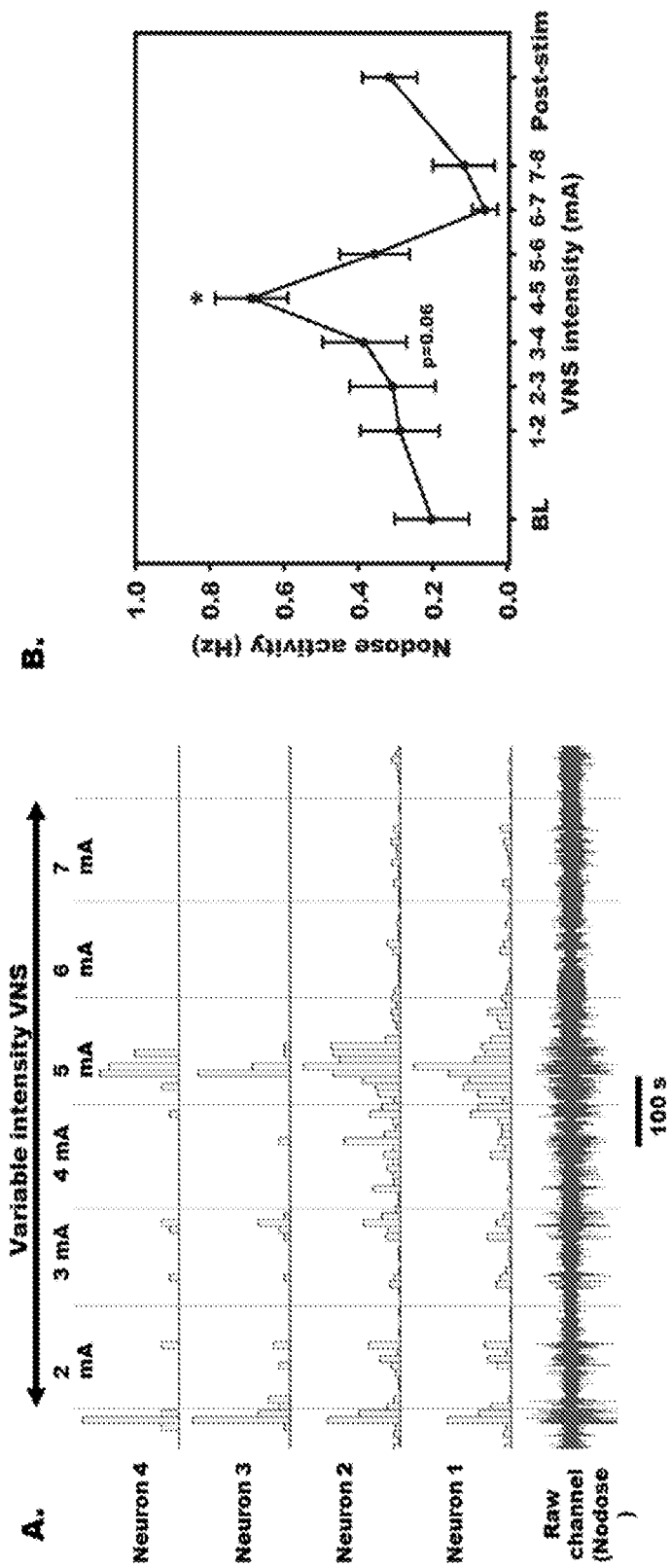
FIG. 32 depicts results from example experiments, demonstrating the effects of graded VNS intensity on Nodose soma activity.

FIG. 32 summarizes the intensity-neural activity relationship of nodose soma in response to cervical VNS stimulation at 2 Hz. While, the bradycardic threshold at 10 Hz was 2.65±0.27 mA, vagal afferents are likely engaged at intensity levels below that level (Ardell J L et al., 2015, Am J Physiol Heart Circ Physiol, 309:H1740-1752). Panel 6A is a representative animal and FIG. 32B summarizes the group data. At lower level VNS intensities (1-4 mA) nodose soma average activity ~doubled (0.2±0.1 to 0.38±0.11 Hz; $p<0.06$). As intensity increased to the 4-5 mA range, the activity generated by identified cardiac-related nodose neurons increased further such that average neuronal activity reached 0.69±0.10 Hz ($p<0.005$ compared to baseline). When VNS intensity was increased above 5 mA spontaneous activity decreased, approaching 0 Hz in the 6-7 mA range (FIG. 32B). With termination of VNS, basal activity returned, with recovery times ranging from 1 to 40 min.

Summary

The major findings of this study are that: 1) the transduction capabilities of nodose ganglion ventricular sensory neurons can be modified by ART such that 2) the ability of such ventricular sensory neurons to transduce the ischemic myocardium becomes obtunded by either SCS or VNS. Without wishing to be bound by any theory, it is proposed that the ability of either form of ART to do so resides in their ability to influence cardiac motor neuronal inputs to the ventricular milieu such that local sensory neurite transduction of that milieu would secondarily change, thereby altering the sensory activity patterns to ischemic stress.

This study also identified the fact that nodose ganglion ventricular afferent neurons respond in a non-linear manner to progressive enhancement of their afferent axonal inputs. The latter observation indicates that some nodose ganglion cardiac afferent neurons do not act solely as simple relay stations to medullary NTS neurons. Rather, these data indicate that some nodose ganglion cardiac sensory neurons display modulatory roles in the transduction of cardiac indices to the medulla.

Structural Organization of the Nodose Ganglia

Morphological observations in this study provide a structural and cellular basis to aid in understanding the function of the nodose ganglia, especially in the context of VNS. Sensory neurons of the canine nodose ganglia exhibit heterogeneity in size and are overall, larger than stellate ganglion neurons that provide efferent input to the heart. Previous work further showed that afferent neurons of the canine nodose ganglia exhibit diversity in expression of neurotransmitters and co-transmitters (Furukawa Y et al., 1996, Am J Physiol, 271:H44-50) and that only a small percentage of nodose ganglion neurons have projections localized to the heart (Furukawa Y et al., 1996, Am J Physiol, 271:H44-50; Gemes G et al., 2013, J Physiol, 591:1111-1131). Nevertheless, this study showed that all sensory neurons of the canine nodose ganglia are completely surrounded by satellite glial cells. This finding agrees with observations made in other species and provides visual evidence for a close interaction of satellite glial cells with the neurons that they surround (Hanani M., 2005, Brain Res Brain Res Rev, 48:457-476; Huang L Y et al., 2013, Glia, 61:1571-1581; Pannese E., 2010, Neuron Glia Biol, 6:3-10). In fact, there is strong evidence that satellite glial cells communicate with each other and have two-way communications with the sensory somata that they surround (Hanani M., 2005, Brain Res Brain Res Rev, 48:457-476; Huang L Y et al., 2013, Glia, 61:1571-1581; Pannese E., 2010, Neuron Glia Biol, 6:3-10). These interactions include satellite glial cells buffering ions in the small space between them and the adjacent sensory neuron and affecting neuronal activity. Lastly, the immunohistochemical staining for synaptophysin provides proof that nodose ganglion neurons lack synaptic inputs, which supports the general view that synaptic transmission does not occur at the somata of sensory neurons (Hanani M., 2005, Brain Res Brain Res Rev, 48:457-476; Huang L Y et al., 2013, Glia, 61:1571-1581).

Nodose Ganglion Sensory Transduction

Only a small proportion of cardiac afferent neurons in nodose ganglia (about 10%) appear to transduce the local mechanical milieu of the atria or ventricles to nucleus tractus solitarius neurons (Armour J A, and Kember G. Cardiac sensory neurons. In: Basic and Clinical Neurocardiology, edited by Armour J A, and Ardell J L. New York: Oxford University Press, 2004, p. 79-117). Many of the latter can also concomitantly transduce the chemical milieu when their associated sensory neurites are exposed to ischemic events, thereby displaying multimodal transduction capabilities (Huang H S et al., 1995, Am J Physiol, 269:H888-901; 49. Thompson G W et al., 2000, Am J Physiol Regul Integr Comp Physiol, 279:R433-439). The data summarized in FIG. 29 confirms these multi-modal capabilities. Local cardiac chemical stimuli induce an order of magnitude greater enhancement of their activity than do local cardiac mechanical stimuli (Armour J A, and Kember G. Cardiac sensory neurons. In: Basic and Clinical Neurocardiology, edited by Armour J A, and Ardell J L. New York: Oxford University Press, 2004, p. 79-117). Furthermore, their capacity to transduce enhancement of the chemical milieu— for instance in the presence of ischemia—persists for a time after removal of the chemical stimulus (Armour J A, and Kember G. Cardiac sensory neurons. In: Basic and Clinical Neurocardiology, edited by Armour J A, and Ardell J L. New York: Oxford University Press, 2004, p. 79-117); afferents are responsible in part for memory within the cardiac nervous system (Ardell J L et al., 2016, J Physiol, 594:3877-3909). There is also a subset of neurons that responded solely to the myocardial ischemia (14 of 36); these neurons may subserve primarily nociceptive function (Foreman R D., 1999, Annu Rev Physiol, 61:143-167).

VNS and Transduction of Ventricular Ischemia by Nodose Neurons

From a functional perspective, VNS mitigates multiple deleterious consequences elicited by transient myocardial ischemia (Calvillo L et al., 2011, J Cardiovasc Pharmacol, 58:500-507; Shinlapawittayatorn K et al., 2013, Heart Rhythm, 10:1700-1707). Mechanisms involved include VNS imposed anti-adrenergic effects, acting via both intrinsic cardiac and end-organ post-ganglionic neural interactions (Kawada T et al., 2006, Life Sci, 78:882-887; McGuirt A S et al., 1997, Am J Physiol, 272:H2525-2533). VNS likewise elicits anti-inflammatory effects (Calvillo L et al., 2011, J Cardiovasc Pharmacol, 58:500-507) and promotes ventricular anti apoptotic pathways, including the activation of Akt cascade, suppressing the cytochrome-c release and preventing caspase-3 activation (Katare R G et al., 2009, J Thorac Cardiovasc Surg, 137:223-231). Finally, VNS preserves myocardial function thereby impacting myocyte energetics (Shinlapawittayatorn K et al., 2014, Heart Rhythm, 11:2278-2287). The data presented herein indicates that while VNS does not disrupt normal sensory transduction of multi-modal sensory activation, it does mitigate the activation phase associated with transient myocardial ischemia. These data support the concept that pre-emptive VNS increases myocyte stress resistance and this translates to modifying nodose ganglion afferent neurons transduction of the ischemic myocardium.

SCS and Transduction of Ventricular Ischemia by Nodose Neurons

Neuromodulation therapies, in particular, SCS are known to suppress the symptomatology of myocardial ischemia (Mannheimer C et al., 2002, Eur Heart J, 23:355-370). These clinical benefits are likely multi-factorial involving neural and myocyte influences (Ardell J L., 2016, Nat Rev Cardiol, 13:127-128). SCS modulates the responsiveness of ischemia-sensitive neurons located within the spinal cord related to both pain perception (Qin C et al., 2008, J Pain, 9:71-78) and cardiovascular control (Ding X et al., 2008, Am J Physiol Regul Integr Comp Physiol, 294:R93-101; Ding X et al., 2008, Am J Physiol Regul Integr Comp Physiol, 295:R1519-1528). SCS likewise blunts ischemia-induced reflex activation of intrathoracic autonomic ganglia (Ardell J L et al., 2009, Am J Physiol Regul Integr Comp Physiol, 297:R470-477; Foreman R D et al., 2000, Cardiovasc Res, 47:367-375). Final, previous studies have demonstrated the involvement of several intracellular mechanisms involved in SCS, namely the $\alpha$1-PKC and $\beta$-PKA pathways which induce protection of myocytes against ischemic stress (Southerland E M et al., 2007, Am J Physiol Heart Circ Physiol, 292:H311-317; Yellon D M et al., 2003, Physiol Rev, 83:1113-1151). Taken together, these factors likely all contribute to the efficacy of SCS to mitigate excessive sympatho-excitation associated with myocardial ischemia (Ardell J L et al., 2016, J Physiol, 594:3877-3909; Ardell J L et al., 2009, Am J Physiol Regul Integr Comp Physiol, 297:R470-477).

Central reflex processing of myocardial ischemia is critically dependent on sensory feedback (Ardell J L et al., 2016, J Physiol, 594:3877-3909) with projections via the dorsal root and nodose ganglia being the two principal pathways (Ardell J L et al., 2016, Compr Physiol, 6:1635-1653). While it is expected that dorsal root ganglia are impacted by SCS (Ardell J L et al., 2016, J Physiol, 594:3877-3909), the results of this study demonstrate that the capacity of first order nodose ganglion cardiac afferent neurons to transduce the ischemic myocardium is also obtunded by SCS. The most likely mechanism for this blunting of nodose ischemia-induced activation is alterations in the myocyte-afferent neural interface, specifically if myocytes are rendered stress-resistant by SCS (Ardell J L., 2016, Nat Rev Cardiol, 13:127-128), the sensory milieu will be correspondingly less impacted by the transient ischemic insult. This is referred to as remote neuromodulation (SCS to nodose) in contradistinction to direct neuromodulation (SCS to DRG). It remains to be determined if VNS can exert the same impact on DRG afferents and their transduction of myocardial ischemia.

Nonlinear Cardiac Milieu Transduction by Nodose Ganglion Afferent Neurons

In this study, it was determined that VNS therapy exerts non-linear effects on nodose sensory neuronal transduction of the ventricular milieu. That is, the activities of the majority of nodose cardiac sensory neurons identified did not increase in a linear fashion with increasing intensity of stimulation. Over low to moderate stimulus intensities (1-5 mA), the activity generated by many identified nodose ganglion afferent neuronal somata increased (FIG. 32). When VNS intensities exceeded 5 mA, activity was reduced, being extinguished in many cases when intensities exceeded 6 mA. Since histological analysis showed the lack of synapses interposed on the nodose soma, yet with intimate associations with glia support cells, the local cell-cell interactions may function as a neural breaker during high level activity. This observation challenges the concept that all nodose ganglion somata act as a simple afferent relay stations to influence medullary nucleus tractus solitarius neurons.

Perspectives and Significance

Data derived from this study indicate that these forms of ART (SCS or VNS therapy) both influence the capacity of nodose ganglion sensory neurons to transduce transient myocardial ischemia such that the transduction of ventricular ischemia to NTS neurons becomes obtunded. Secondly, such ART does so primarily by altering the ventricular milieu rather than directly affecting afferent neuronal function. That occurs because ART affects efferent neuronal inputs that alter that milieu transduced to medullary neurons. Future studies should consider specifics of the sensory neurite-myocyte and interstitial interface in response to ART. What is evident is that primary afferent transduction is not impacted, but the response to transient myocardial ischemia is. Since apoptosis is correspondingly reduced (Shinlapawittayatorn K et al., 2013, Heart Rhythm, 10:1700-1707; Southerland E M et al., 2007, Am J Physiol Heart Circ Physiol, 292:H311-317), the diminished afferent signal is not "silent" ischemia, but instead a reflection that ART is cardioprotective.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of modulating cardiac function in a subject, comprising the steps of:
    contacting at least one neuron of the intrinsic cardiac nervous system of the subject with a recording electrode;
    measuring the electrical activity of the at least one neuron of the intrinsic cardiac nervous system via the recording electrode;
    contacting a nerve or ganglion of the parasympathetic autonomic nervous system of the subject with a stimulating electrode; and
    applying at least one electrical stimulation comprising kilohertz frequency alternating current (KHFAC) or charge balanced direct current (CBDC) to the nerve or ganglion of the parasympathetic autonomic nervous system via the stimulating electrode to modulate nerve or ganglion electrical function without blocking electrical activity.

2. The method of claim 1, wherein the nerve or ganglion of the cardiac nervous system is selected from the group consisting of the vagus nerve, spinal cord, and mediastinal nerve.

3. The method of claim 1, wherein the electrode is contacted to at least one of the group consisting of: cervical vagosympathetic nerve trunk, intrathoracic vagosympathetic nerve trunk, and auricular branch of vagus nerve.

4. The method of claim 1, wherein the method comprises contacting an electrode to the spinal cord, and applying at least one electrical signal to the spinal cord.

5. The method of claim 1, wherein the step of measuring electrical activity of the at least one neuron of the intrinsic cardiac nervous system comprises contacting the recording electrode to at least one selected from the group consisting of: atrial intrinsic cardiac ganglia and ventricular intrinsic cardiac ganglia.

6. The method of claim 1, wherein further comprising measuring of electrical activity of at least one neuron of a nodose ganglia.

7. The method of claim 1, wherein the step of measuring cardiac electrical activity comprises contacting the recording electrode to at least one selected from the group consisting of the atrial epicardial surface, atrial endocardial surface, ventricular epicardium, ventricular epicardium, and myocardium of the atrial or ventricular tissue.

8. The method of claim 1, wherein modulating the activity of a nerve or ganglion of the parasympathetic autonomic nervous system is controlled by detection of a signal measured from the at least one neuron of the intrinsic cardiac nervous system.

9. A system for modulating cardiac function comprising:
    one or more recording electrodes for measuring the activity of at least one neuron of the intrinsic cardiac nervous system; and
    one or more stimulating electrodes for applying an electrical stimulus to a nerve or ganglion of the parasympathetic autonomic nervous system,
    wherein the one or more stimulating electrode is configured to modulate a nerve or ganglion of the parasympathetic autonomic nervous system via kilohertz frequency alternating current (KHFAC) or charge balanced direct current (CBDC) without blocking electrical activity.

10. A method for treating or preventing a cardiac disorder in a subject, comprising the steps of:
    contacting a nerve or ganglion of the parasympathetic autonomic nervous system of the subject with a stimulating electrode; and
    applying at least one electrical stimulation comprising kilohertz frequency alternating current (KHFAC) or charge balanced direct current (CBDC) to the nerve or ganglion of the parasympathetic autonomic nervous system via the stimulating electrode to modulate the activity of at least one local circuit neuron (LCN) of the cardiac nervous system without blocking electrical activity.

11. The method of claim 10, wherein the method comprises electrical stimulation of the vagus nerve of the subject.

12. The method of claim 10, wherein the method further comprises measuring the electrical activity of at least one neuron of the intrinsic cardiac nervous system.

13. A method of monitoring multi-pole cardioneural function, comprising:
    measuring the electrical activity of at least one neuron of the intrinsic cardiac nervous system; and
    measuring the cardiac electrical activity of the heart.

14. The method of claim 13, wherein the method comprises contacting at least one electrode to a location selected from the group consisting of: atrial intrinsic cardiac ganglia and ventricular intrinsic cardiac ganglia.

15. The method of claim 13, wherein the method comprises contacting at least one electrode to the atrial epicardial surface or the atrial endocardial surface.

16. The method of claim 11, wherein the electrical stimulation of the vagus nerve is delivered in a continuously cyclic fashion comprising an on phase and an off phase.

17. The method of claim 16, wherein the on cycle is 14 seconds and the off cycle is 48 seconds.

18. The method of claim 11, wherein the electrical simulation is applied for a period of at least 40 days.

* * * * *